(12) United States Patent
Yoshida et al.

(10) Patent No.: US 9,604,972 B2
(45) Date of Patent: Mar. 28, 2017

(54) NITROGEN-CONTAINING HETEROAROMATIC RING COMPOUND

(75) Inventors: Kei Yoshida, Sodegaura (JP); Ryohei Hashimoto, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 818 days.

(21) Appl. No.: 13/606,379

(22) Filed: Sep. 7, 2012

(65) Prior Publication Data

US 2013/0062597 A1 Mar. 14, 2013

Related U.S. Application Data

(60) Provisional application No. 61/580,505, filed on Dec. 27, 2011.

(30) Foreign Application Priority Data

Sep. 9, 2011 (JP) .................................. 2011-197031
Dec. 27, 2011 (JP) .................................. 2011-285219

(51) Int. Cl.
*H01L 51/54* (2006.01)
*C09K 11/06* (2006.01)
(Continued)

(52) U.S. Cl.
CPC ............ *C07D 405/14* (2013.01); *C09K 11/06* (2013.01); *H01L 51/0065* (2013.01);
(Continued)

(58) Field of Classification Search
CPC .... H05B 33/10; C07D 209/00; C07D 209/80; C07D 209/82; C07D 209/86;
(Continued)

(56) References Cited

U.S. PATENT DOCUMENTS 6,229,012 B1 * 5/2001 Hu ........................ C07D 251/24
544/180
2006/0083943 A1 * 4/2006 Maxted ................ C07D 209/86
428/690
(Continued)

FOREIGN PATENT DOCUMENTS

JP 2009-21336 A 1/2009
JP 2009021336 A * 1/2009
(Continued)

OTHER PUBLICATIONS

Machine translation of JP2009-021336. Date of publication: Jan. 29, 2009.*

(Continued)

Primary Examiner — Andrew K Bohaty
(74) Attorney, Agent, or Firm — Oblon, McClelland, Maier & Neustadt, L.L.P.

(57) ABSTRACT

A nitrogen-containing heteroaromatic compound is represented by the following formula (A).

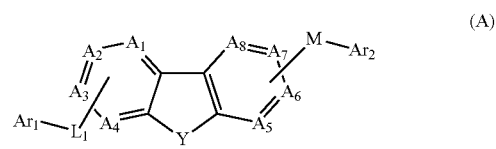

(A)

wherein Y is an oxygen atom or a sulfur atom, M is a substituted or unsubstituted nitrogen-containing heteroaromatic group, and $Ar_2$ is a substituted aromatic hydrocarbon group having 6 to 18 ring carbon atoms, a substituted or unsubstituted monocyclic heteroaromatic group having 5 or 6 ring atoms, a dibenzofuran ring group that may be substituted with a substituent (excluding a 3-carbazolyl group and an N-carbazolyl group), a dibenzothiophene ring group that may be substituted with a substituent (excluding a 3-carbazolyl group and an N-carbazolyl group), or a nitrogen-containing polycyclic group among nitrogen-containing polycyclic groups respectively represented by the following formulas (1) to (5).

(1)

(2)

(3)

(4)

(Continued)

-continued

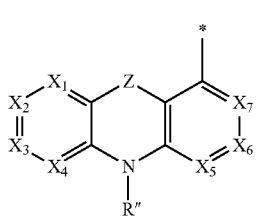

(5)

19 Claims, 1 Drawing Sheet

(51) Int. Cl.
*C07D 405/14* (2006.01)
*H01L 51/00* (2006.01)
*H05B 33/10* (2006.01)
*H01L 51/50* (2006.01)

(52) U.S. Cl.
CPC ...... *H01L 51/0072* (2013.01); *H01L 51/0073* (2013.01); *H05B 33/10* (2013.01); *C09K 2211/104* (2013.01); *C09K 2211/1007* (2013.01); *C09K 2211/1011* (2013.01); *C09K 2211/1029* (2013.01); *C09K 2211/1044* (2013.01); *C09K 2211/1059* (2013.01); *C09K 2211/1088* (2013.01); *C09K 2211/1092* (2013.01); *H01L 51/0059* (2013.01); *H01L 51/0085* (2013.01); *H01L 51/5016* (2013.01)

(58) Field of Classification Search
CPC .. C07D 209/88; C07D 307/00; C07D 307/91; C07D 333/00; C07D 333/76; C07D 405/00; C07D 405/02; C07D 405/04; C07D 405/14; C07D 409/00; C07D 409/02; C07D 409/04; C07D 409/14; C09K 11/06; C09K 2211/00; C09K 2211/10; C09K 2211/1007; C09K 2211/1003; C09K 2211/1011; C09K 2211/1018; C09K 2211/1029; C09K 2211/1088; C09K 2211/1044; C09K 2211/1059; C09K 2211/1092; C09K 2211/104; H01L 51/0032; H01L 51/005; H01L 51/0059; H01L 51/0062; H01L 51/0065; H01L 51/0067; H01L 51/0068; H01L 51/0071; H01L 51/0072; H01L 51/0073; H01L 51/0074; H01L 51/0085; H01L 51/0087; H01L 51/0088; H01L 51/50; H01L 51/5012; H01L 51/5016
See application file for complete search history.

(56) References Cited

U.S. PATENT DOCUMENTS

| | | | |
|---|---|---|---|
| 2009/0096360 A1* | 4/2009 | Tanaka et al. | 313/504 |
| 2009/0284138 A1 | 11/2009 | Yasukawa et al. | |
| 2009/0302745 A1* | 12/2009 | Otsu et al. | 313/504 |
| 2010/0084966 A1 | 4/2010 | Otsu et al. | |
| 2011/0006670 A1 | 1/2011 | Katakura et al. | |
| 2012/0007498 A1 | 1/2012 | Otsu et al. | |

FOREIGN PATENT DOCUMENTS

| | | | |
|---|---|---|---|
| JP | 2010-135467 A | | 6/2010 |
| JP | 2010135467 A | * | 6/2010 |
| JP | 2010238880 A | * | 10/2010 |
| JP | 2010-251675 A | | 11/2010 |
| JP | 2011-84531 A | | 4/2011 |
| WO | WO 2008/072596 A1 | | 6/2008 |
| WO | WO 2011/004639 A1 | | 1/2011 |
| WO | WO 2011/010840 A1 | | 1/2011 |
| WO | WO 2012/004765 A2 | | 1/2012 |
| WO | WO 2012/074195 A1 | | 6/2012 |
| WO | WO 2012/077520 A1 | | 6/2012 |
| WO | WO 2012/087007 A1 | | 6/2012 |

OTHER PUBLICATIONS

Machine translation of JP2010-135467. Date of publication: Jun. 17, 2010.*
Machine translation of JP2010-238880. Date of publication: Oct. 21, 2010.*
International Search Report issued Oct. 23, 2012 in PCT/JP2012/005453 (with English Translation of Categories of Cited Documents).

* cited by examiner

NITROGEN-CONTAINING HETEROAROMATIC RING COMPOUND

TECHNICAL FIELD

The invention relates to a nitrogen-containing heteroaromatic compound, a material for an organic electroluminescence device that includes the nitrogen-containing heteroaromatic compound, and an organic electroluminescence device.

BACKGROUND

An organic electroluminescence (EL) device may be a fluorescent organic EL device or a phosphorescent organic EL device, and an optimal device design for the emission mechanism of each type of organic EL device has been studied. It is known that a highly efficient phosphorescent organic EL device cannot be obtained by merely applying fluorescent device technology due to the emission characteristics. The reasons therefor are generally considered to be as follows.

Specifically, since phosphorescence utilizes triplet excitons, a compound used for forming the emitting layer must have a large energy gap. This is because the energy gap (hereinafter may be referred to as "singlet energy") of a compound is normally larger than the triplet energy (i.e., the difference in energy between the lowest excited triplet state and the ground state) of the compound.

Therefore, it is necessary to form the emitting layer using a host material having a triplet energy higher than that of a phosphorescent dopant material in order to efficiently confine the triplet energy of the phosphorescent dopant material in the emitting layer. It is also necessary to provide an electron-transporting layer and a hole-transporting layer adjacent to the emitting layer, and form the electron-transporting layer and the hole-transporting layer using a compound having a triplet energy higher than that of the phosphorescent dopant material.

Specifically, since a compound having a large energy gap as compared with a compound used for the fluorescent organic EL device is necessarily used for the phosphorescent organic EL device when designing the phosphorescent organic EL device based on a known organic EL device design concept, the driving voltage for the entire organic EL device increases.

Hydrocarbon compounds that exhibit high oxidation resistance and high reduction resistance and are useful for the fluorescent device have a small energy gap due to the large spatial extent of the π-electron cloud. Therefore, an organic compound that contains a heteroatom (e.g., oxygen or nitrogen) is selected for the phosphorescent organic EL device instead of such hydrocarbon compounds. As a result, the phosphorescent organic EL device has a short lifetime as compared with the fluorescent organic EL device.

The fact that the relaxation rate of triplet excitons of a phosphorescent dopant material is much higher than that of singlet excitons also significantly affects the device performance. Specifically, it is expected that efficient emission from singlet excitons can be obtained since diffusion of excitons into the layers (e.g., hole-transporting layer and electron-transporting layer) situated around the emitting layer rarely occurs due to the high relaxation rate that leads to emission. In contrast, since emission from triplet excitons is spin-forbidden (i.e., the relaxation rate is low), diffusion of excitons into the layers situated around the emitting layer easily occurs, and thermal energy inactivation occurs from a compound other than a specific phosphorescent compound. Specifically, it is important to control the electron-hole recombination region as compared with the fluorescent organic EL device.

It is thus necessary to select materials and a device design differing from those of the fluorescent organic EL device in order to obtain a highly efficient phosphorescent organic EL device.

In particular, when designing a phosphorescent organic EL device that emits blue light, it is necessary to use a compound having high triplet energy for forming the emitting layer and the layers situated around the emitting layer as compared with a phosphorescent organic EL device that emits green to red light. More specifically, the triplet energy of a host material used to form the emitting layer generally must be 3.0 eV or more in order to obtain blue phosphorescence without causing efficiency loss. In order to obtain a compound that has such a high triplet energy and meets the requirements for an organic EL material, it is necessary to employ a new molecular design concept that takes account of the electronic state of π-electrons instead of merely combining molecular parts (e.g., heterocyclic compound) having high triplet energy.

In view of the above situation, a compound having a structure obtained by bonding a plurality of heterocyclic rings has been studied as a material for a phosphorescent organic EL device that emits blue light. For example, JP-A-2009-021336 discloses a compound having a dibenzofuran ring and an azine ring as a material for forming an electron-transporting layer.

WO2008/072596 discloses a compound obtained by bonding two dibenzofurans and the like via a divalent linking group as a host material for forming a phosphorescent emitting layer.

JP-A-2011-084531 discloses a compound having an azadibenzofuran structure as a host material for forming a phosphorescent emitting layer and a material for forming an electron-transporting layer.

SUMMARY OF THE INVENTION

An object of the invention is to provide a novel material for an organic EL device.

The inventor of the invention found that the driving voltage of a phosphorescent organic EL device can be reduced by utilizing a compound having a structure obtained by bonding an azine ring (nitrogen-containing heteroaromatic ring) and a dibenzofuran ring, a dibenzothiophene ring, or a ring similar to a dibenzofuran ring or dibenzothiophene ring. This finding has led to the completion of the invention.

The invention provides the following nitrogen-containing heteroaromatic compound and the like.

1. A nitrogen-containing heteroaromatic compound represented by a formula (A),

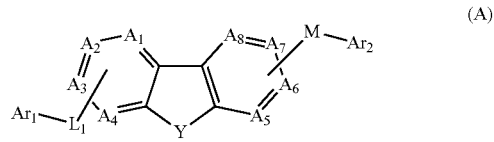

(A)

wherein $A_1$ to $A_8$ are independently $CR^1$, $R^1$ is independently a hydrogen atom, a substituted or unsubstituted alkyl group having 1 to 20 carbon atoms, a substituted or unsubstituted cycloalkyl group having 3 to 20 carbon atoms that form a ring (hereinafter referred to as "ring carbon atoms"), a substituted or unsubstituted alkoxy group having 1 to 20 carbon atoms, a substituted or unsubstituted cycloalkoxy group having 3 to 20 ring carbon atoms, a substituted or unsubstituted aromatic hydrocarbon group having 6 to 18 ring carbon atoms, a substituted or unsubstituted aryloxy group having 6 to 18 ring carbon atoms, a substituted or unsubstituted heteroaromatic group having 5 to 18 atoms that form a ring (hereinafter referred to as "ring atoms"), a substituted or unsubstituted amino group, a substituted or unsubstituted silyl group, a fluorine atom, a substituted or unsubstituted fluoroalkyl group, or a cyano group, Y is an oxygen atom or a sulfur atom, $Ar_1$ is a hydrogen atom, a substituted or unsubstituted aromatic hydrocarbon group having 6 to 18 ring carbon atoms, or a substituted or unsubstituted heteroaromatic group having 5 to 18 ring atoms, $L_1$ is a single bond, a substituted or unsubstituted aromatic hydrocarbon group having 6 to 18 ring carbon atoms, or a substituted or unsubstituted heteroaromatic group having 5 to 18 ring atoms, M is a substituted or unsubstituted nitrogen-containing heteroaromatic group, and $Ar_2$ is a substituted aromatic hydrocarbon group having 6 to 18 ring carbon atoms, a substituted or unsubstituted monocyclic heteroaromatic group having 5 or 6 ring atoms, a dibenzofuran ring group that may be substituted with a substituent (excluding a 3-carbazolyl group and an N-carbazolyl group), a dibenzothiophene ring group that may be substituted with a substituent (excluding a 3-carbazolyl group and an N-carbazolyl group), or a nitrogen-containing polycyclic group among nitrogen-containing polycyclic groups respectively represented by formulas (1) to (5), wherein $X_1$ to $X_8$ are independently CR' or a nitrogen atom, Z is a single bond, an oxygen atom, a sulfur atom, =S(=O), =S(=O)$_2$, =SiR$^2$R$^3$, =CR$^4$R$^5$, or =NR$^6$, R', R", and $R^2$ to $R^6$ are independently an atom or a group among the atoms and the groups mentioned for $R^1$, provided that a plurality of R' may be either identical or different when a plurality of R' are present, and * is a position bonded to M.

2. The nitrogen-containing heteroaromatic compound according to 1, wherein M is a substituted or unsubstituted monocyclic nitrogen-containing heteroaromatic group.

3. The nitrogen-containing heteroaromatic compound according to 1 or 2, wherein M is a substituted or unsubstituted 6-membered nitrogen-containing heteroaromatic group.

4. The nitrogen-containing heteroaromatic compound according to any one of 1 to 3, wherein $Ar_2$ is a substituted aromatic hydrocarbon group having 6 to 18 ring carbon atoms, a substituted or unsubstituted monocyclic heteroaromatic group having 5 or 6 ring atoms, a dibenzofuran ring group that may be substituted with a substituent (excluding a 3-carbazolyl group and an N-carbazolyl group), a dibenzothiophene ring group that may be substituted with a substituent (excluding a 3-carbazolyl group and an N-carbazolyl group), or a nitrogen-containing polycyclic group among nitrogen-containing polycyclic groups respectively represented by formulas (1a) to (5a), (1)
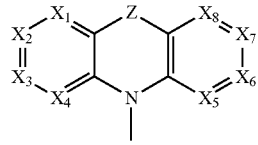

(2)
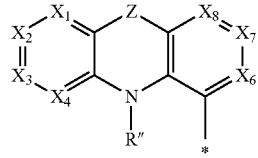

(3)
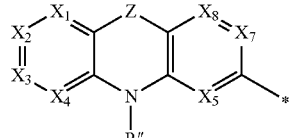

(4)
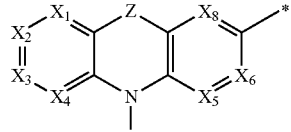

(5)
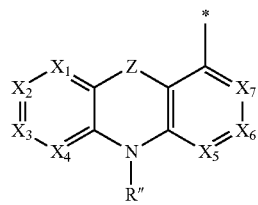

(1a)
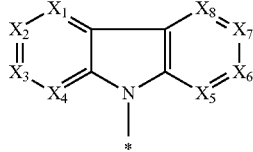

(2a)
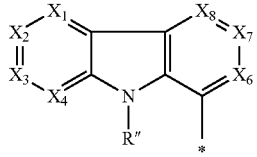

(3a)
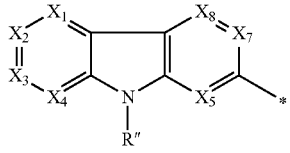

(4a)
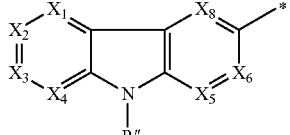

(5a)
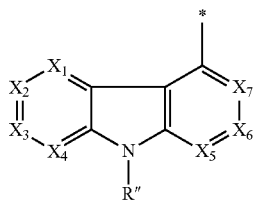

wherein $X_1$ to $X_8$, R", and * are the same as defined for the formulas (1) to (5).

5. The nitrogen-containing heteroaromatic compound according to any one of 1 to 3, wherein Ar₂ is a nitrogen-containing polycyclic group among the nitrogen-containing polycyclic groups respectively represented by the formulas (1) to (5).
6. The nitrogen-containing heteroaromatic compound according to 4, wherein Ar₂ is a nitrogen-containing polycyclic group among the nitrogen-containing polycyclic groups respectively represented by the formulas (1a) to (5a).
7. The nitrogen-containing heteroaromatic compound according to any one of 1 to 3 and 5, wherein Ar₂ is the nitrogen-containing polycyclic group represented by the formula (1).
8. The nitrogen-containing heteroaromatic compound according to 4 or 6, wherein Ar₂ is the nitrogen-containing polycyclic group represented by the formula (1a).
9. The nitrogen-containing heteroaromatic compound according to any one of 1 to 8, wherein L₁ is a single bond.
10. The nitrogen-containing heteroaromatic compound according to any one of 1 to 9, wherein Ar₁ is a substituted or unsubstituted carbazole ring group or a substituted or unsubstituted azacarbazole ring group.
11. The nitrogen-containing heteroaromatic compound according to any one of 1 to 10, wherein Ar₁ is a substituted or unsubstituted carbazole ring group that is bonded to L₁ at position 9.
12. A material for an organic electroluminescence device including the nitrogen-containing heteroaromatic compound according to any one of 1 to 11.
13. An organic electroluminescence device including a cathode, an anode, and one or more organic thin film layers that are provided between the cathode and the anode and include an emitting layer, at least one organic thin film layer among the one or more organic thin film layers including the material for an organic electroluminescence device according to 12.
14. The organic electroluminescence device according to 13, wherein the emitting layer includes the material for an organic electroluminescence device as a host material.
15. The organic electroluminescence device according to 13 or 14, wherein the emitting layer includes a phosphorescent emitting material, and the phosphorescent emitting material is an orthometalated complex of a metal atom selected from iridium (Ir), osmium (Os), and platinum (Pt).
16. The organic electroluminescence device according to any one of 13 to 15, including an organic thin film layer between the cathode and the emitting layer, wherein the organic thin film layer includes the material for an organic electroluminescence device.

The invention thus provides a novel material for an organic EL device.

DESCRIPTION OF EXEMPLARY EMBODIMENTS

Figure 1:
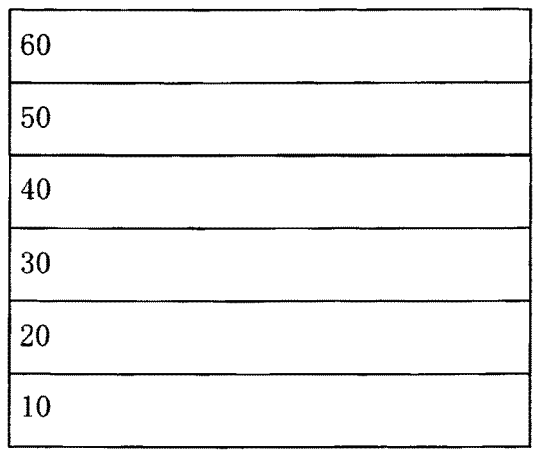
FIG. 1 is a view illustrating an organic EL device according to one embodiment of the invention.

The nitrogen-containing heteroaromatic compound according to the invention is represented by the following formula (A).

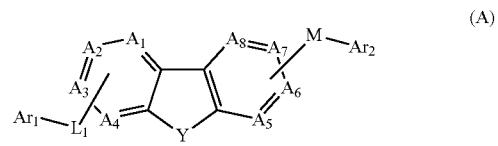

In the formula (A), $A_1$ to $A_8$ are independently $CR^1$.

$R^1$ is independently a hydrogen atom, a substituted or unsubstituted alkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted cycloalkoxy group having 3 to 20 ring carbon atoms, a substituted or unsubstituted aromatic hydrocarbon group (aryl group) having 6 to 18 ring carbon atoms, a substituted or unsubstituted aryloxy group having 6 to 18 ring carbon atoms, a substituted or unsubstituted heteroaromatic group (heteroaryl group) having 5 to 18 ring atoms, a substituted or unsubstituted amino group, a substituted or unsubstituted silyl group, a fluorine atom, a substituted or unsubstituted fluoroalkyl group, or a cyano group.

$L_1$ is bonded to one of $A_1$ to $A_4$ via the carbon atom. M is bonded to one of $A_5$ to $A_8$ via the carbon atom.

Y is an oxygen atom or a sulfur atom, and preferably an oxygen atom.

$Ar_1$ is a hydrogen atom, a substituted or unsubstituted aromatic hydrocarbon group having 6 to 18 ring carbon atoms, or a substituted or unsubstituted heteroaromatic group having 5 to 18 ring atoms, and preferably a substituted or unsubstituted carbazole ring group or a substituted or unsubstituted azacarbazole ring group. When $Ar_1$ is a substituted or unsubstituted carbazole ring group, it is more preferable that $Ar_1$ be bonded to $L_1$ at position 9 of the carbazole ring.

$L_1$ is a single bond, a substituted or unsubstituted aromatic hydrocarbon group having 6 to 18 ring carbon atoms, or a substituted or unsubstituted heteroaromatic group having 5 to 18 ring atoms, and preferably a single bond.

M is a substituted or unsubstituted nitrogen-containing heteroaromatic group, preferably a substituted or unsubstituted 5-membered or 6-membered monocyclic nitrogen-containing heteroaromatic group, and more preferably a substituted or unsubstituted pyridine ring group, a substituted or unsubstituted pyrimidine ring group, or a substituted or unsubstituted triazine ring group.

$Ar_2$ is a substituted aromatic hydrocarbon group having 6 to 18 ring carbon atoms, a substituted or unsubstituted monocyclic heteroaromatic group having 5 or 6 ring atoms, a dibenzofuran ring group that may be substituted with a substituent (excluding a 3-carbazolyl group and an N-carbazolyl group), a dibenzothiophene ring group that may be substituted with a substituent (excluding a 3-carbazolyl group and an N-carbazolyl group), or a nitrogen-containing polycyclic group among nitrogen-containing polycyclic groups respectively represented by the following formulas (1) to (5), preferably a nitrogen-containing polycyclic group among the nitrogen-containing polycyclic groups respectively represented by the formulas (1) to (5), and more preferably the nitrogen-containing polycyclic group represented by the formula (1).

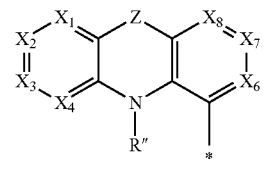

(1)

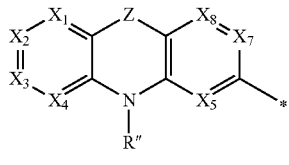

(2)

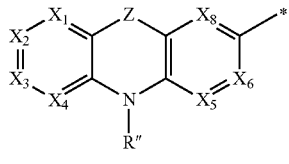

(3)

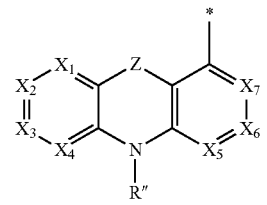

(4)

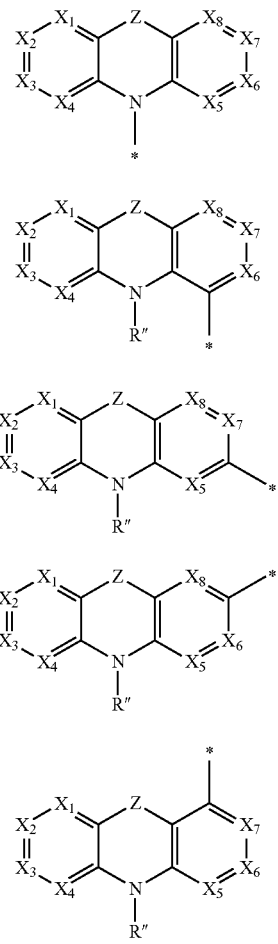

(5)

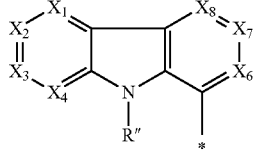

(2a)

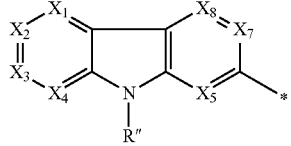

(3a)

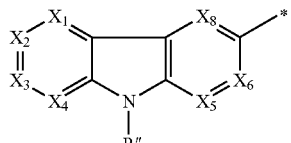

(4a)

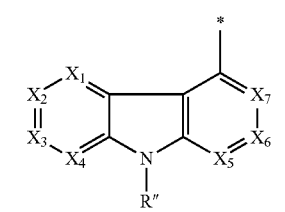

(5a)

In the formulas (1) to (5), $X_1$ to $X_8$ are independently CR' or a nitrogen atom.

Z is a single bond, an oxygen atom, a sulfur atom, =S(=O), =S(=O)$_2$, =SiR$^2$R$^3$, =CR$^4$R$^5$, or =NR$^6$.

R', R", and R$^2$ to R$^6$ are independently an atom or a group among the atoms and the groups mentioned for R$^1$. A plurality of R' may be either identical or different when a plurality of R' are present.

* is a position bonded to M.

The nitrogen-containing polycyclic group among the nitrogen-containing polycyclic groups respectively represented by the formulas (1) to (5) is preferably a nitrogen-containing polycyclic group among nitrogen-containing polycyclic groups respectively represented by the following formulas (1a) to (5a), and more preferably the nitrogen-containing polycyclic group represented by the formula (1a).

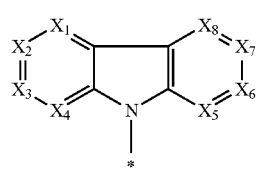

(1a)

In the formulas (1a) to (5a), $X_1$ to $X_8$, R", and * are the same as defined for the formulas (1) to (5).

When Ar$_2$ is a substituted aromatic hydrocarbon group having 6 to 18 ring carbon atoms, an aromatic hydrocarbon group having 6 to 18 ring carbon atoms or a heteroaromatic group having 5 to 18 ring atoms (e.g., phenyl group, carbazolyl group, and dibenzofuranyl group) is preferable as the substituent.

The compound represented by the formula (A) has a structure in which dibenzofuran, dibenzothiophene, or a ring similar to dibenzofuran or dibenzothiophene is bonded to a nitrogen-containing heteroaromatic ring. The spatial extent of the LUMO of the compound increases due to the above structure, so that the electron-transporting capability is improved. This makes it possible to implement a decrease in voltage of an organic EL device.

Examples of each group that may be included in the compound represented by the formula (A) are described below.

Examples of the alkyl group having 1 to 20 carbon atoms include linear or branched alkyl groups. Specific examples of the alkyl group having 1 to 20 carbon atoms include a methyl group, an ethyl group, a propyl group, an isopropyl group, an n-butyl group, an isobutyl group, a sec-butyl group, a tert-butyl group, an n-pentyl group, an n-hexyl group, an n-heptyl group, an n-octyl group, and the like. Among these, a methyl group, an ethyl group, a propyl group, an isopropyl group, an n-butyl group, an isobutyl group, a sec-butyl group, and a tert-butyl group are preferable, and a methyl group, an ethyl group, a propyl group, an isopropyl group, an n-butyl group, a sec-butyl group, and a tert-butyl group are more preferable.

Examples of the cycloalkyl group having 3 to 20 carbon atoms include a cyclopropyl group, a cyclobutyl group, a cyclopentyl group, a cyclohexyl group, a 1-adamantyl group, a 2-adamantyl group, a 1-norbornyl group, a 2-norbornyl group, and the like. Among these, a cyclopentyl group and a cyclohexyl group are preferable.

The alkoxy group having 1 to 20 carbon atoms is represented by —OY. Examples of Y include the above alkyl groups. Examples of the alkoxy group include a methoxy group and an ethoxy group. The alkoxy group may be substituted with a fluorine atom. In this case, a trifluoromethoxy group and the like are preferable.

The cycloalkoxy having 3 to 20 ring carbon atoms is represented by —OY. Examples of Y include the above cycloalkyl groups. Examples of the cycloalkoxy group include a cyclopentyloxy group and a cyclohexyloxy group.

The aromatic hydrocarbon group having 6 to 18 ring carbon atoms is preferably an aromatic hydrocarbon group having 6 to 12 ring carbon atoms. Note that the term "ring carbon atom" used herein refers to a carbon atom that forms a saturated ring, an unsaturated ring, or an aromatic ring.

Specific examples of a monovalent aromatic hydrocarbon group include a phenyl group, a naphthyl group, an anthryl group, a phenanthryl group, a naphthacenyl group, a pyrenyl group, a chrysenyl group, a benzo[c]phenanthryl group, a benzo[g]chrysenyl group, a triphenylenyl group, a fluorenyl group, a benzofluorenyl group, a dibenzofluorenyl group, a biphenylyl group, a terphenyl group, a quarterphenyl group, a fluoranthenyl group, and the like. Among these, a phenyl group, a biphenyl group, a terphenyl group, a tolyl group, a xylyl group, and a naphthyl group are preferable.

When the aromatic hydrocarbon ring is substituted with a substituent, the above alkyl groups are preferable as the substituent. Examples of the substituted aromatic hydrocarbon group include a 9,9-dimethylfluorenyl group and the like.

Examples of a divalent or higher valency aromatic hydrocarbon group include divalent or higher valency groups derived from the above groups.

The aryloxy group having 6 to 18 ring carbon atoms is represented by —OY. Examples of Y include the above aromatic hydrocarbon groups. Examples of the aryloxy group include a phenoxy group.

The heteroaromatic group having 5 to 18 ring atoms is preferably a heteroaromatic group having 5 to 10 ring atoms.

Specific examples of a monovalent heteroaromatic group include a pyrrolyl group, a pyrazinyl group, a pyridinyl group, a pyrimidinyl group, a triazinyl group, an indolyl group, an isoindolyl group, an imidazolyl group, a furyl group, a benzofuranyl group, an isobenzofuranyl group, a dibenzofuranyl group, a dibenzothiophenyl group, a quinolyl group, an isoquinolyl group, a quinoxalinyl group, a carbazolyl group, a phenanthridinyl group, an acridinyl group, a phenanthrolinyl group, a phenazinyl group, a phenothiazinyl group, a phenoxadinyl group, an oxazolyl group, an oxadiazolyl group, a furazanyl group, a thienyl group, a benzothiophenyl group, a dihydroacridinyl group, an azacarbazolyl group, a quinazolinyl group, and the like. Among these, a dibenzofuranyl group, a dibenzothiophenyl group, a carbazolyl group, and an azacarbazolyl group are preferable.

Examples of a divalent or higher valency heteroaromatic group include divalent or higher valency groups derived from the above groups.

Examples of the monocyclic heteroaromatic group having 5 or 6 ring atoms include the monocyclic heteroaromatic group having 5 or 6 ring atoms among the above heteroaromatic groups. Among these, a pyridine ring group, a pyrimidine ring group, and a triazine ring group are preferable.

Examples of the substituted or unsubstituted amino group include an amino group, alkylamino groups or dialkylamino groups having 1 to 10 (preferably 1 to 6) carbon atoms, arylamino groups or diarylamino groups having 6 to 30 (preferably 6 to 20, and more preferably 6 to 10) carbon atoms, and the like.

Among these, a diphenylamino group is preferable.

Examples of the substituted or unsubstituted silyl group include a silyl group, alkylsilyl groups having 1 to 10 (preferably 1 to 6) carbon atoms, arylsilyl groups having 6 to 30 (preferably 6 to 20, and more preferably 6 to 10) carbon atoms, and the like.

Specific examples of the alkylsilyl groups include a trimethylsilyl group, a triethylsilyl group, a t-butyldimethylsilyl group, a vinyldimethylsilyl group, a propyldimethylsilyl group, and the like.

Specific examples of the arylsilyl groups include a triphenylsilyl group, a phenyldimethylsilyl group, a t-butyldiphenylsilyl group, a tritolylsilyl group, a trixylylsilyl group, a trinaphthylsilyl group, and the like.

Examples of the fluoroalkyl group include groups obtained by substituting the above alkyl groups having 1 to 20 carbon atoms with one or more fluorine atoms. Specific examples of the fluoroalkyl group include a fluoromethyl group, a difluoromethyl group, a trifluoromethyl group, a fluoroethyl group, a trifluoromethylmethyl group, a pentafluoroethyl group, and the like. Among these, a trifluoromethyl group and a pentafluoroethyl group are preferable.

Examples of a substituent that may substitute each substituted or unsubstituted group include the above alkyl groups, the above substituted or unsubstituted amino groups, the above substituted or unsubstituted silyl groups, the above aromatic hydrocarbon groups, the above cycloalkyl groups, the above heteroaromatic groups, the above alkoxy groups, the above fluoroalkyl groups, halogen atoms (e.g., fluorine atom, chlorine atom, bromine atom, and iodine atom (preferably a fluorine atom), a hydroxyl group, a nitro group, a cyano group, a carboxyl group, an aryloxy group, diarylphosphino groups (e.g., diphenylphosphino group), diarylphosphine oxide groups (e.g., diphenylphosphine oxide group), diarylphosphinoaryl groups (e.g., diphenylphosphinophenyl group), and the like.

The term "hydrogen atom" used herein includes isotopes of hydrogen that differ in the number of neutrons (i.e., protium, deuterium, and tritium).

Specific examples of the compound represented by the formula (A) are shown below.

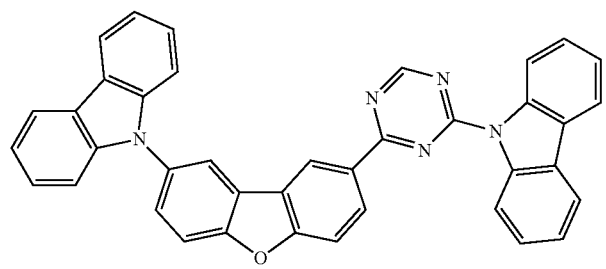
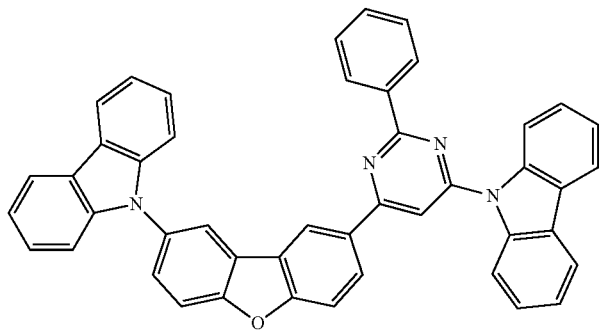

-continued
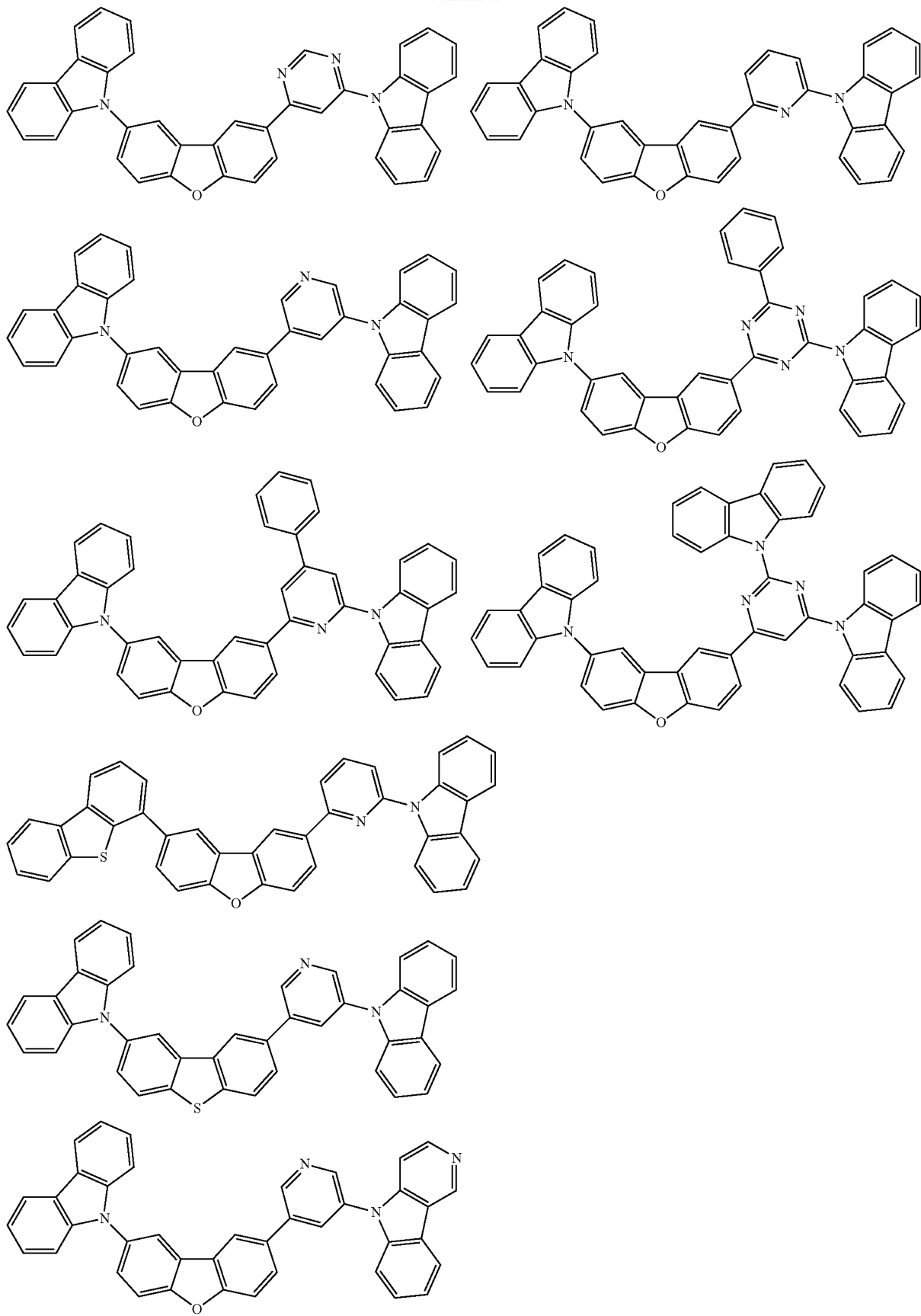

-continued
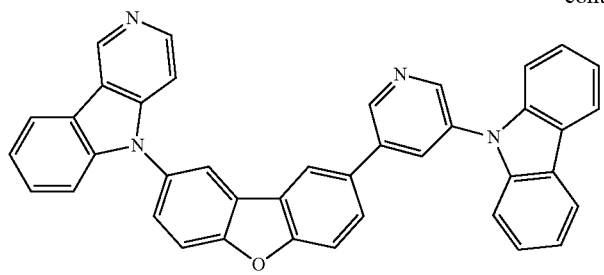
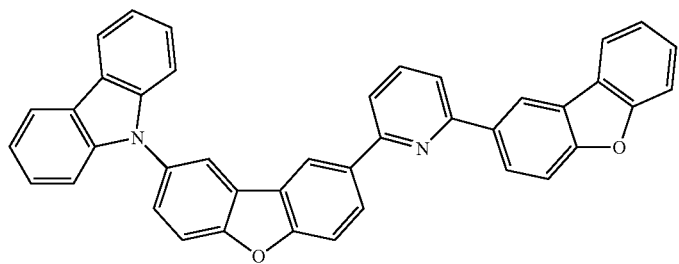
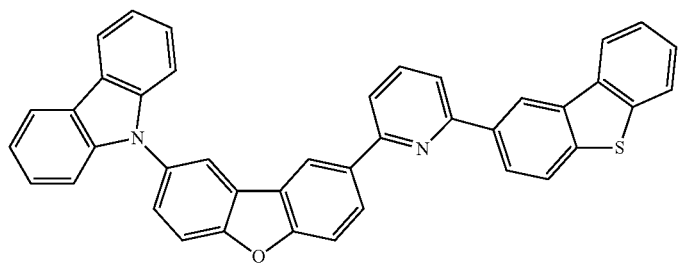
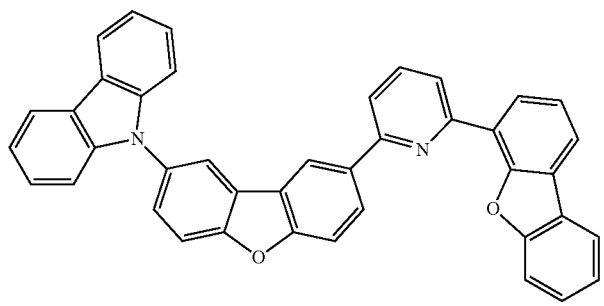
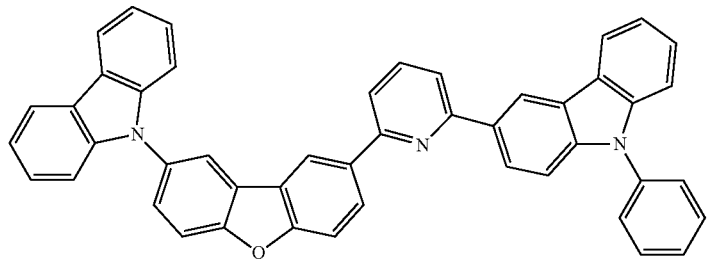
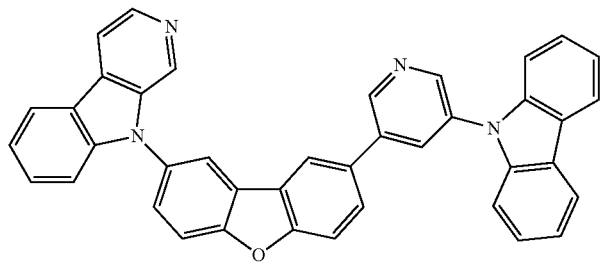

-continued
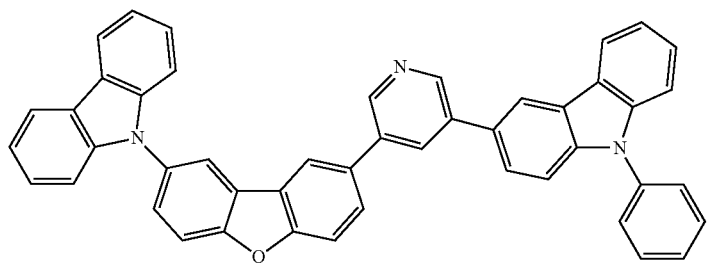
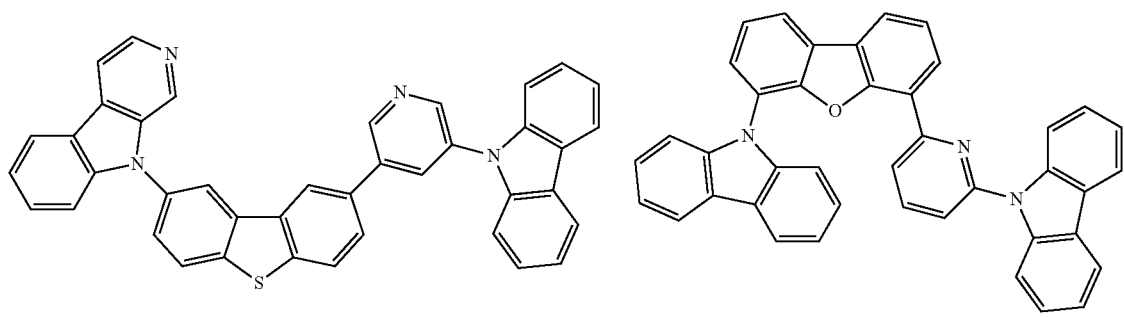
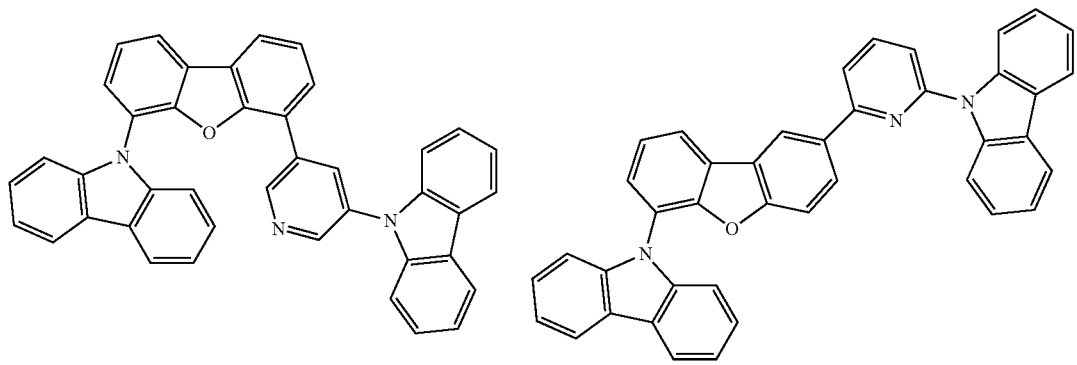
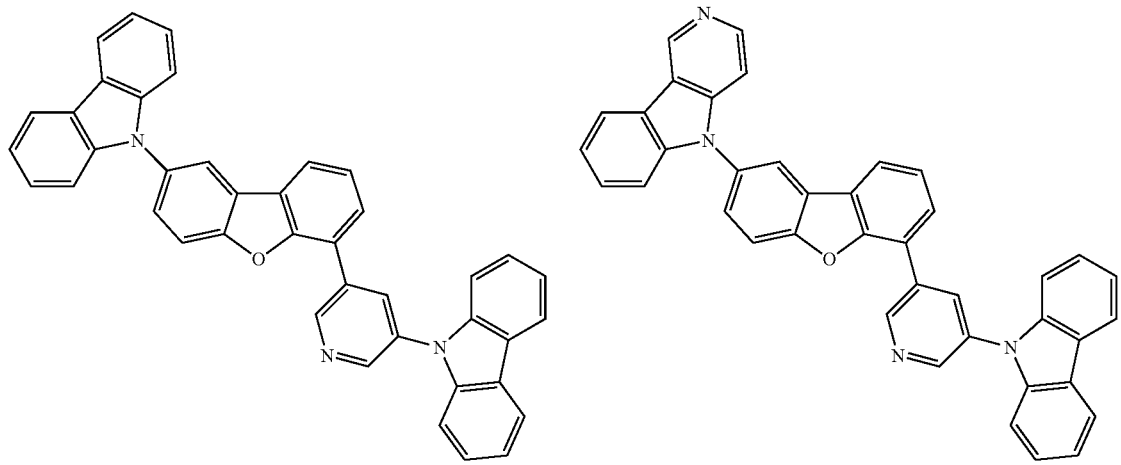

-continued
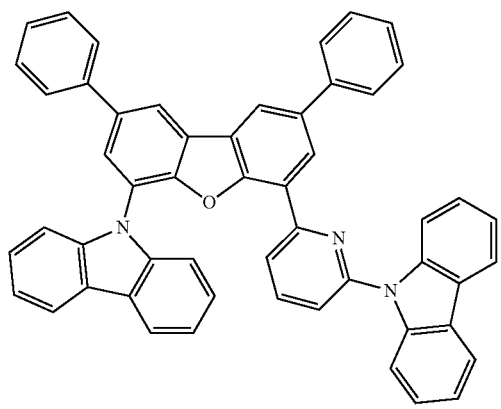
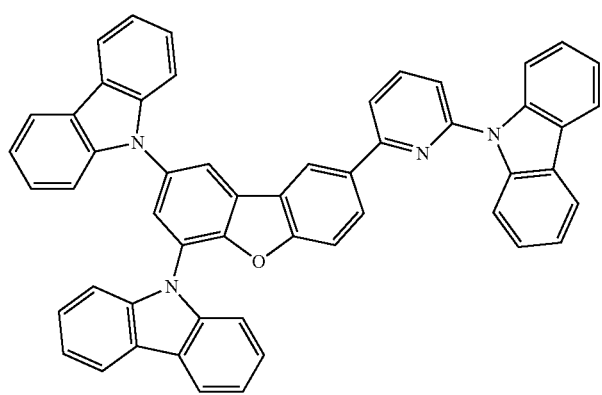
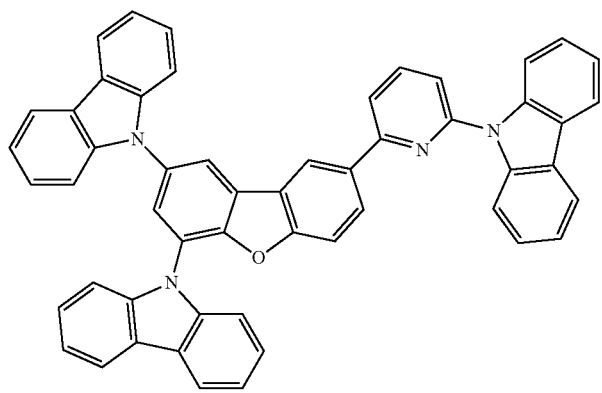
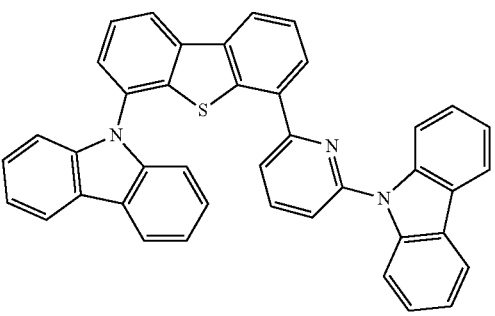
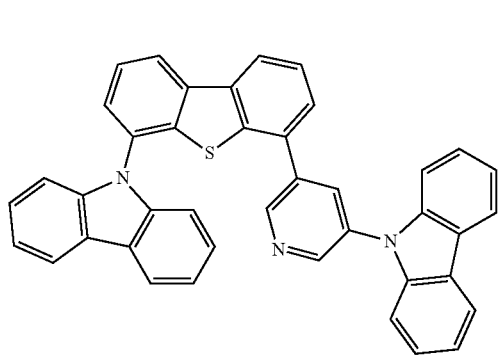
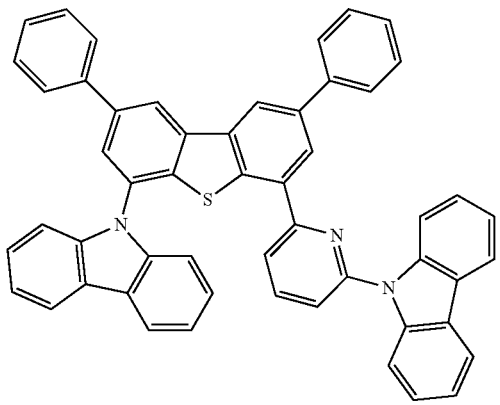
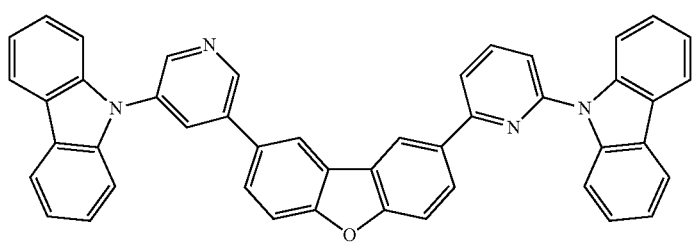
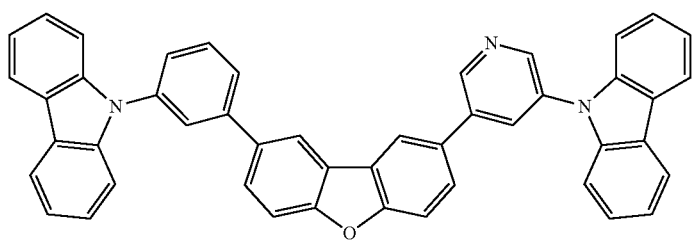

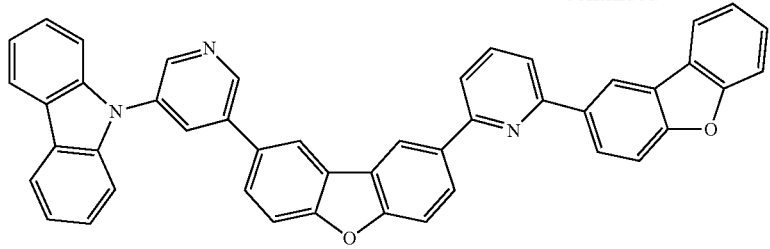
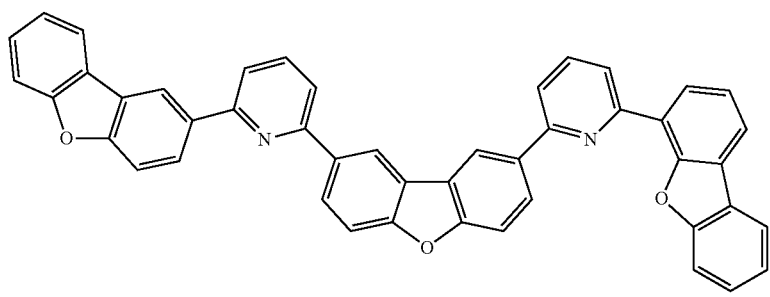
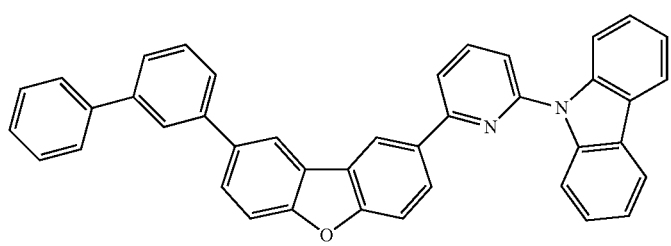
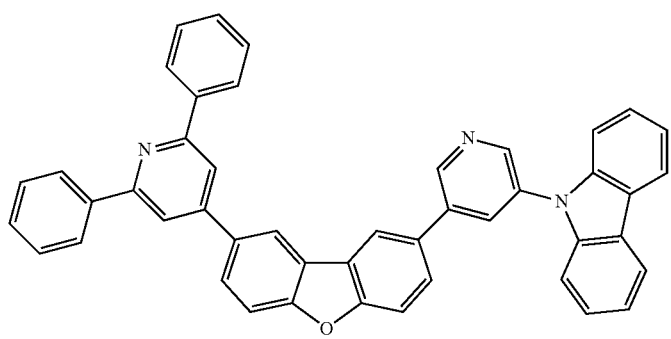
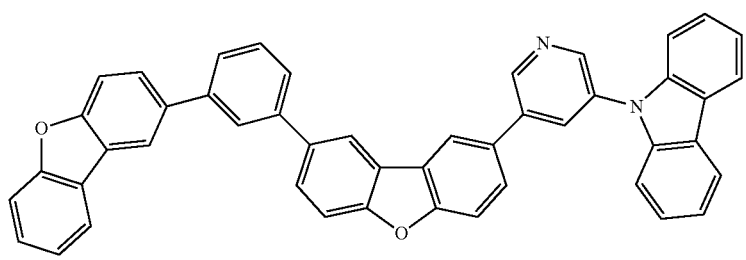

-continued
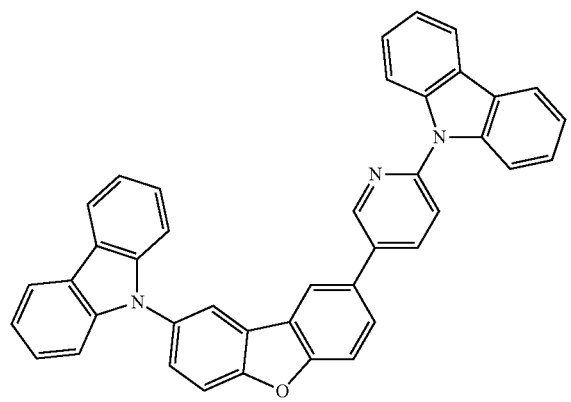
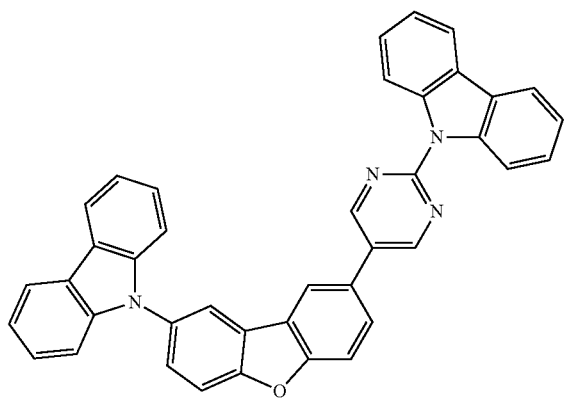
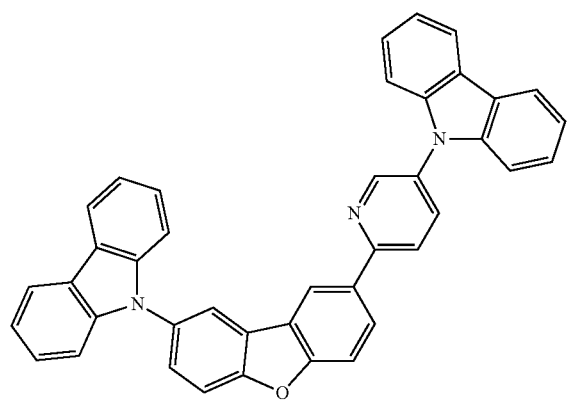
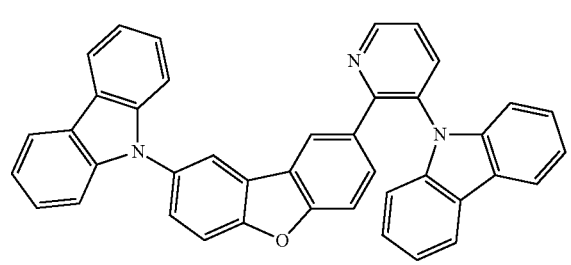
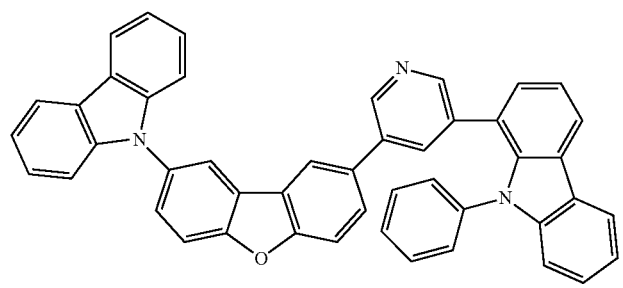
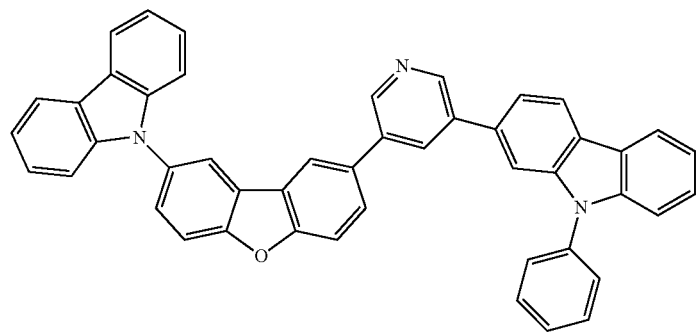

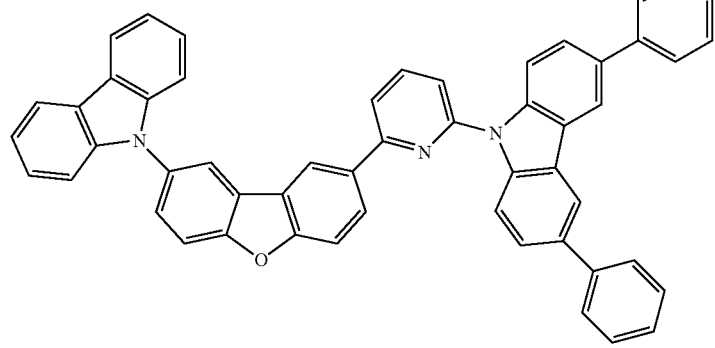
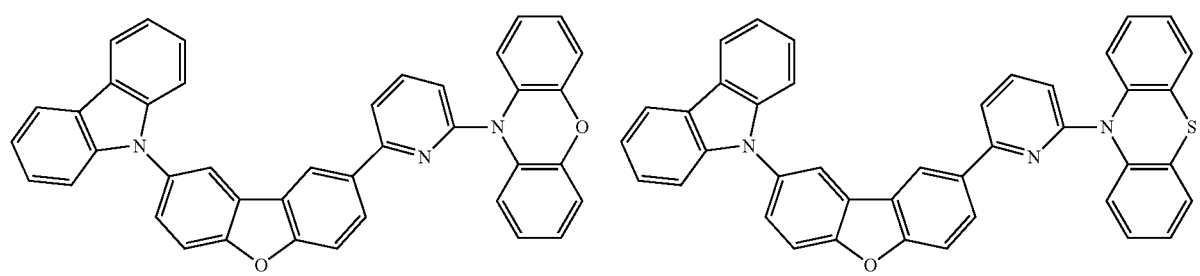
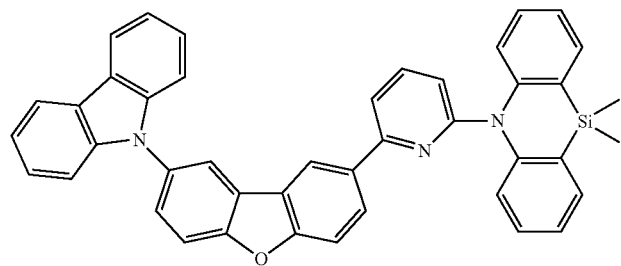
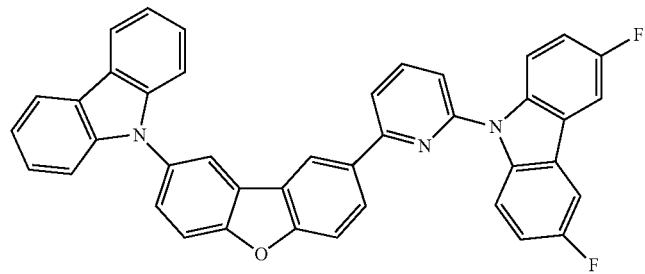
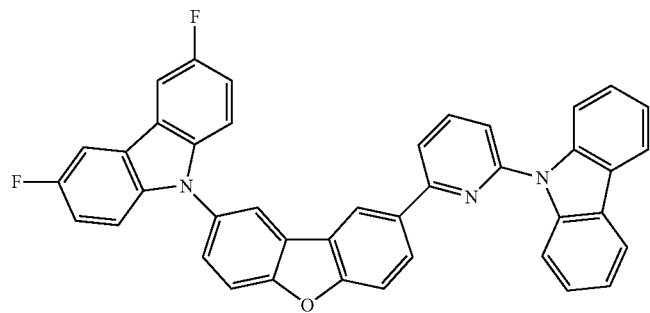

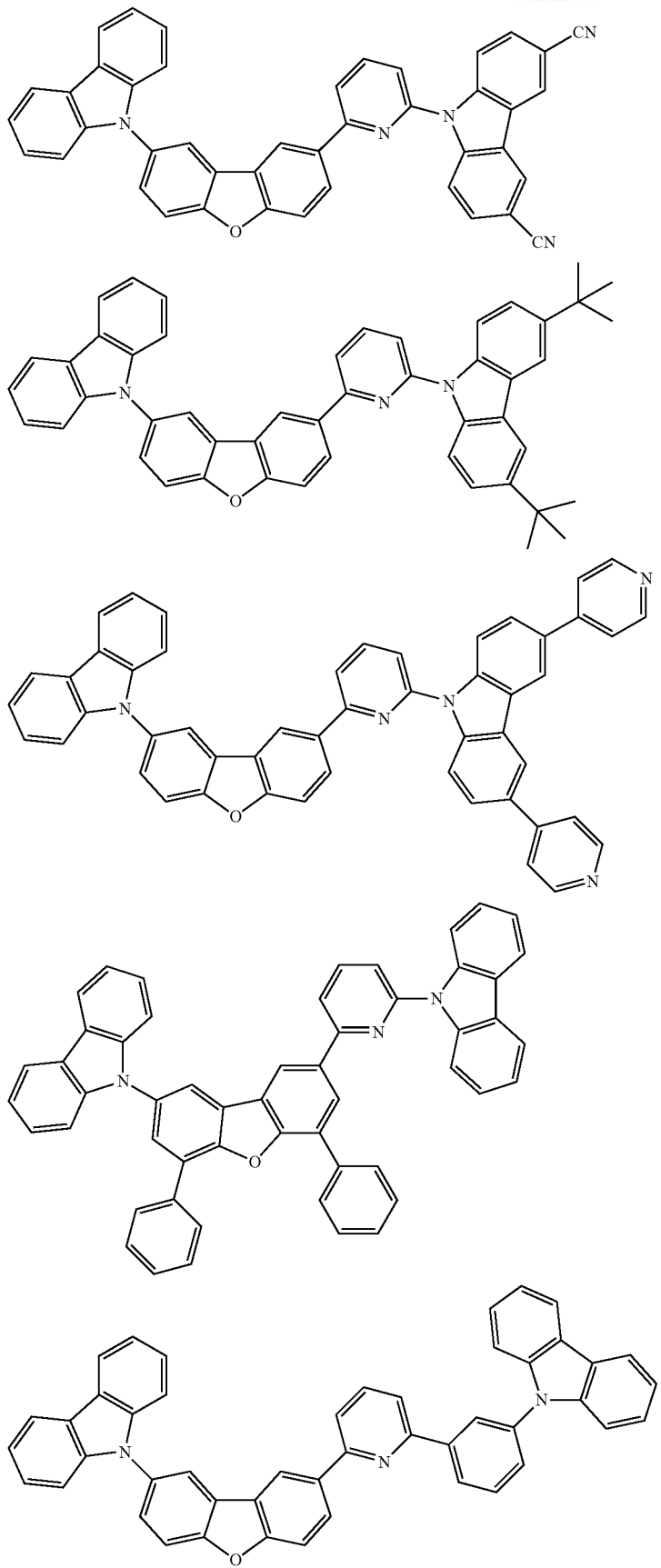

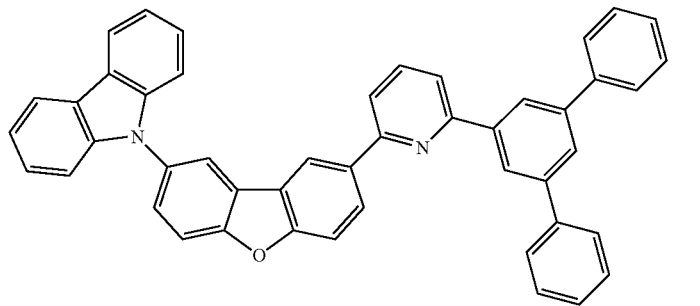
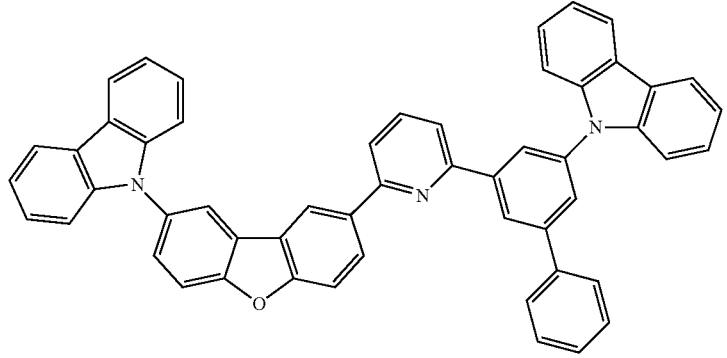
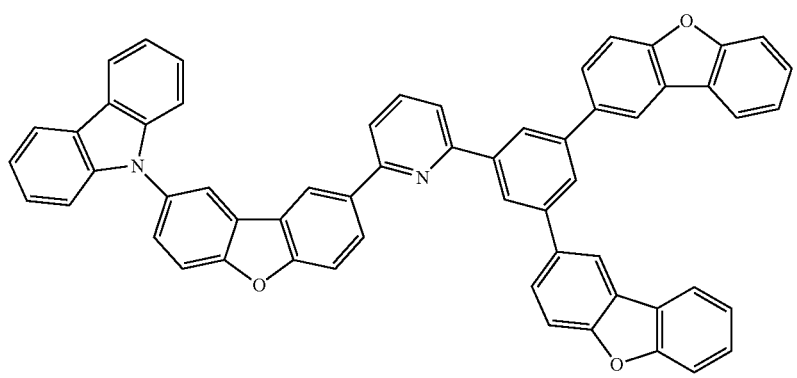
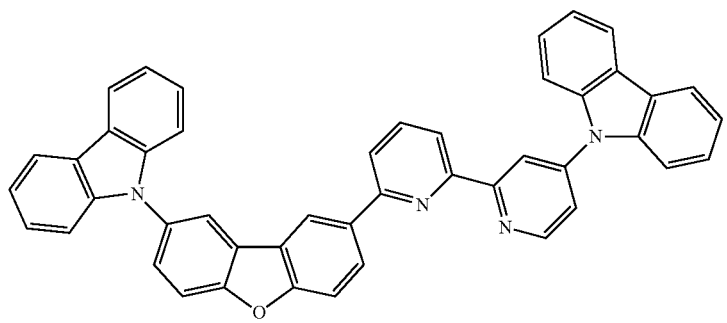
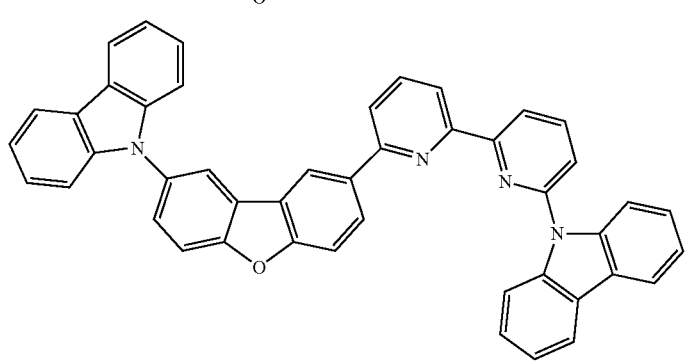

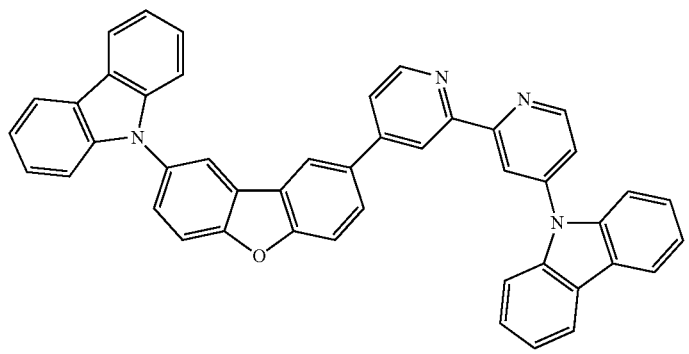
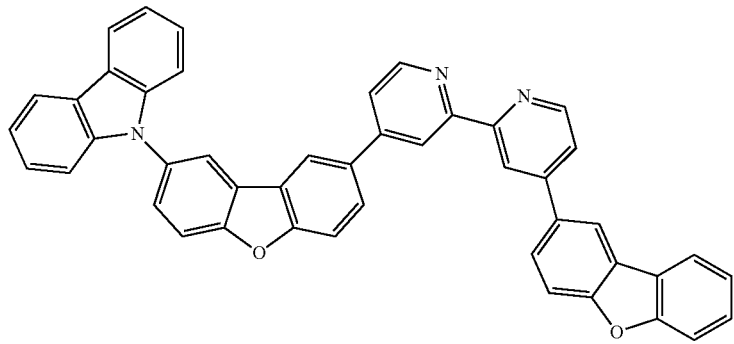
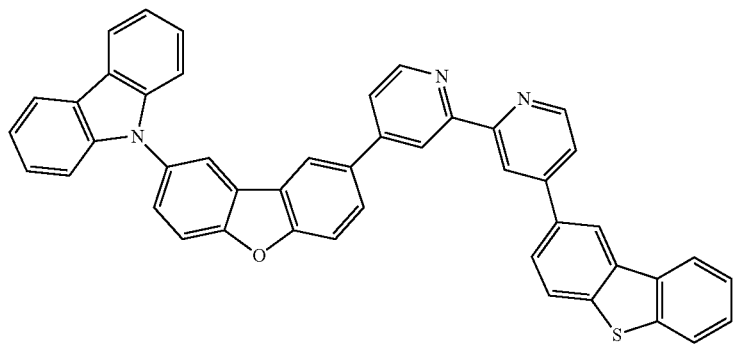
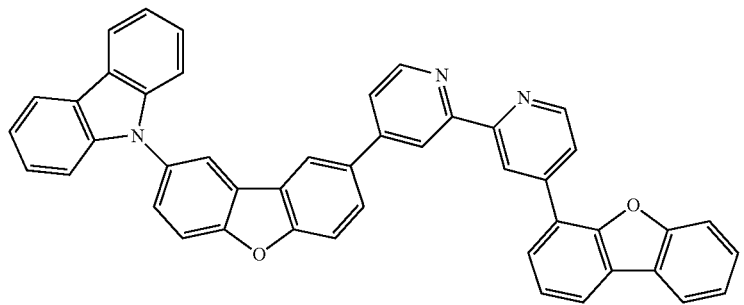
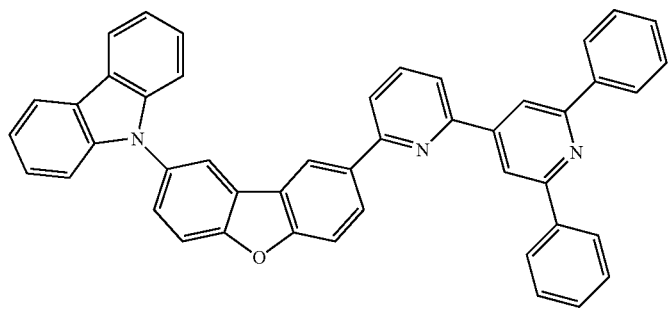

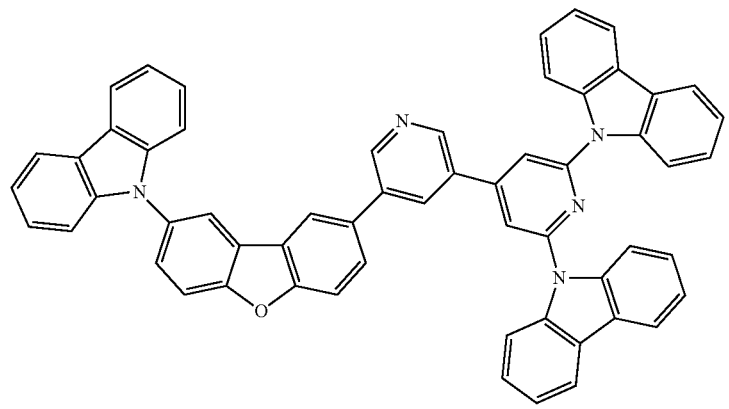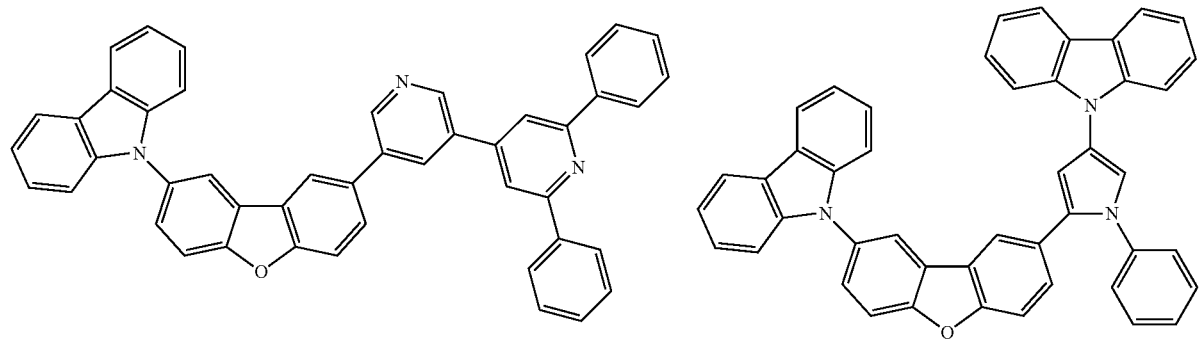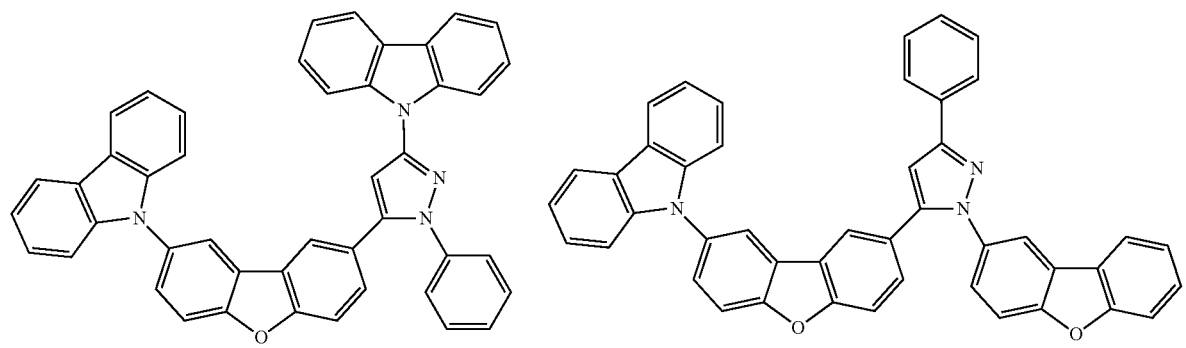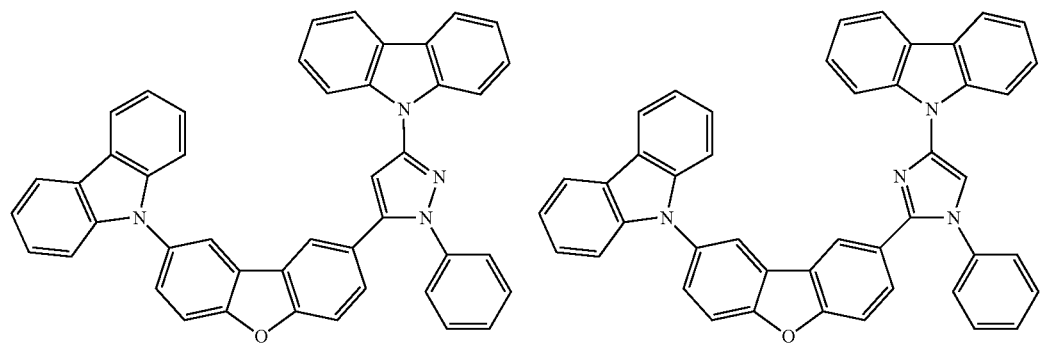

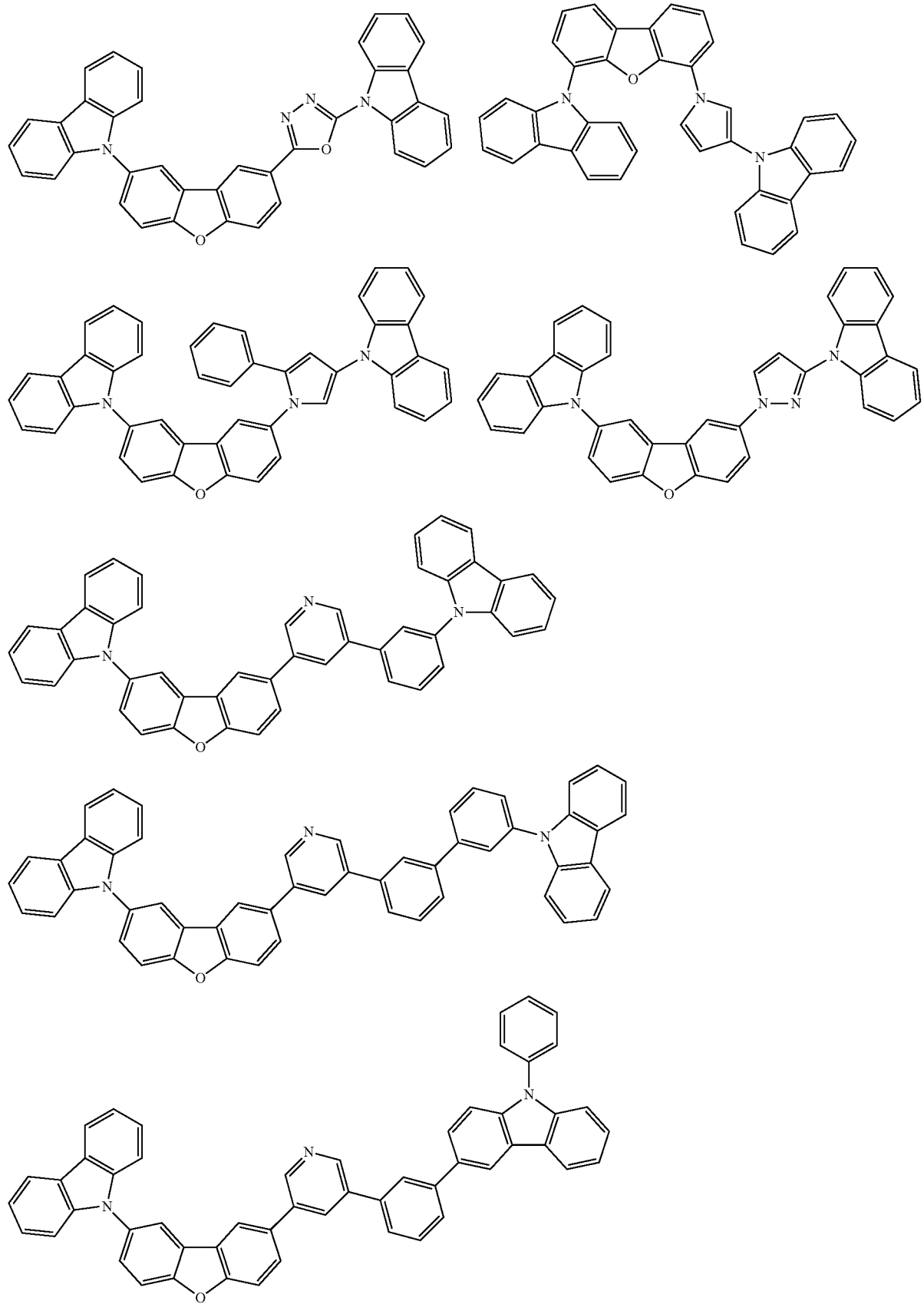

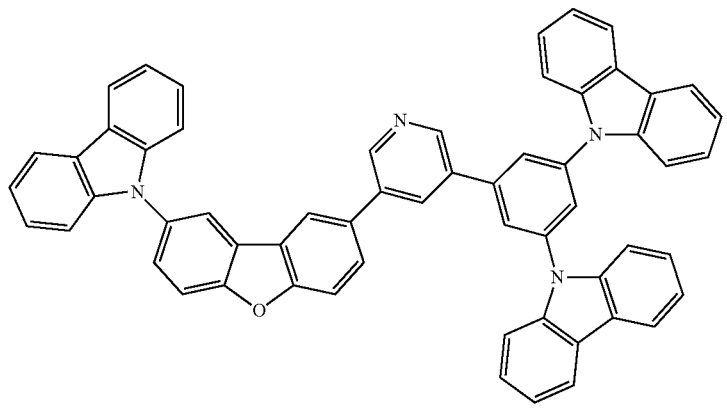
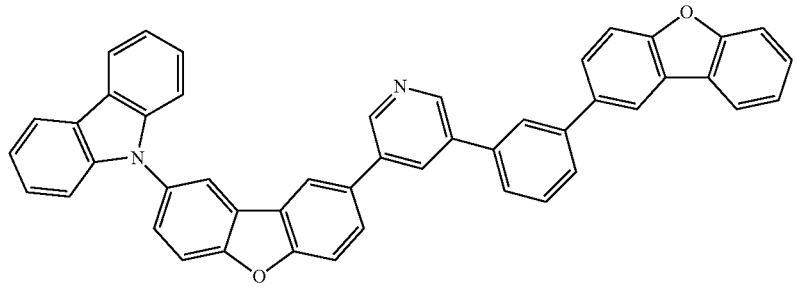
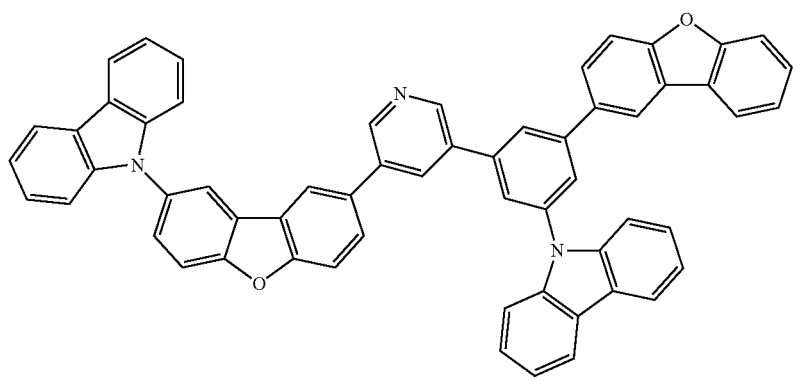
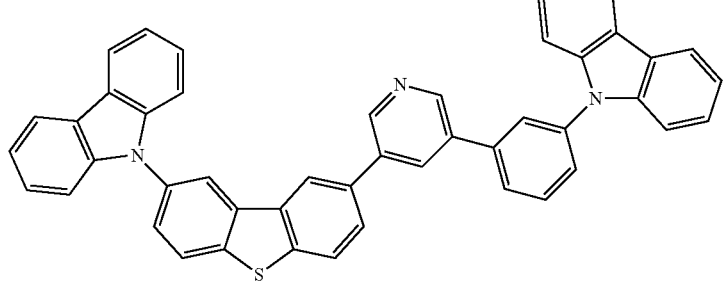
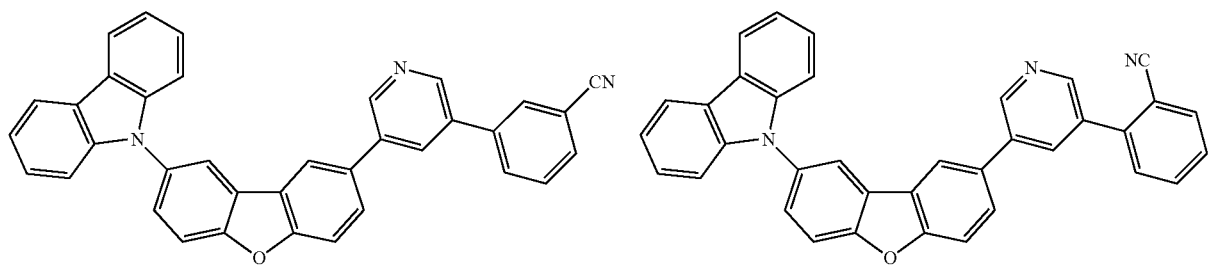

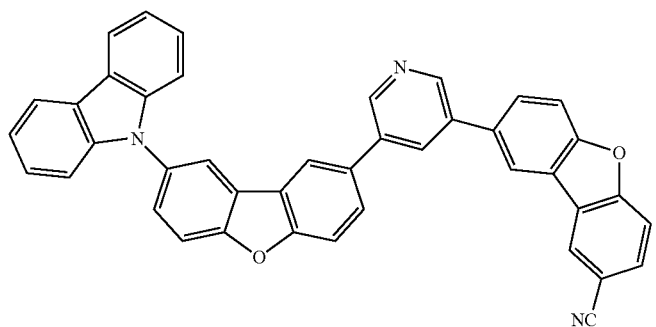
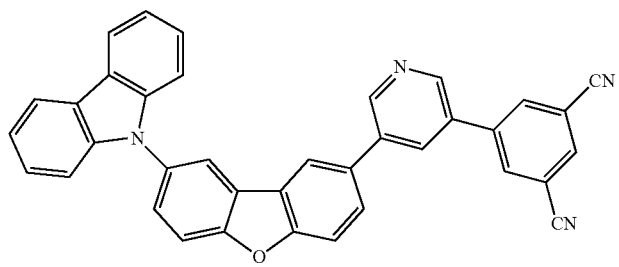
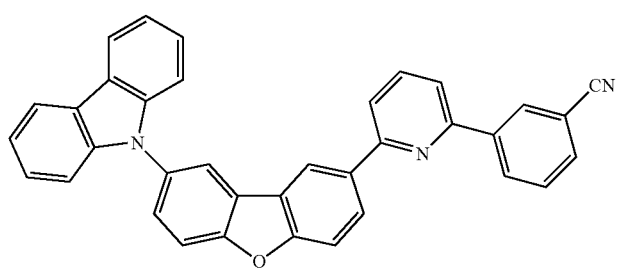
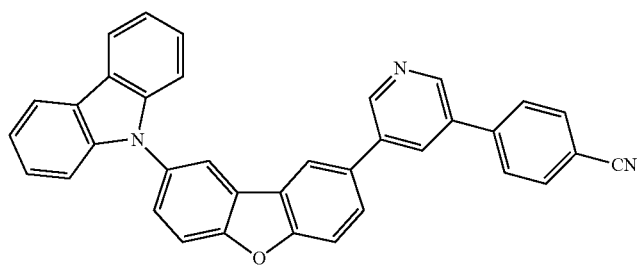
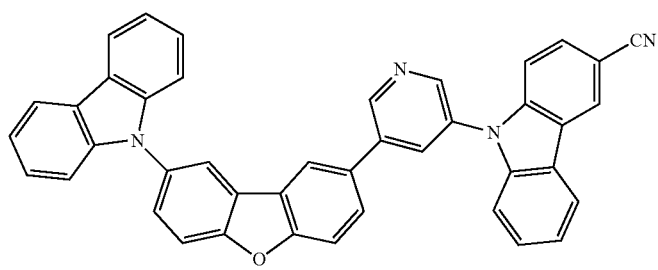
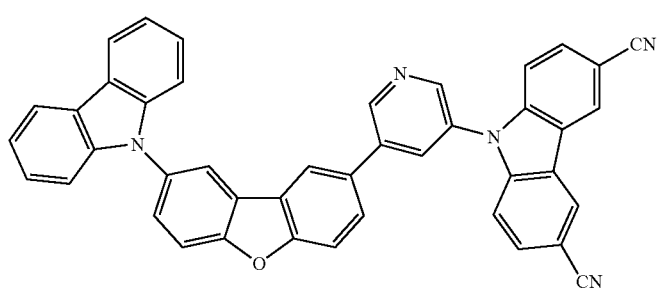

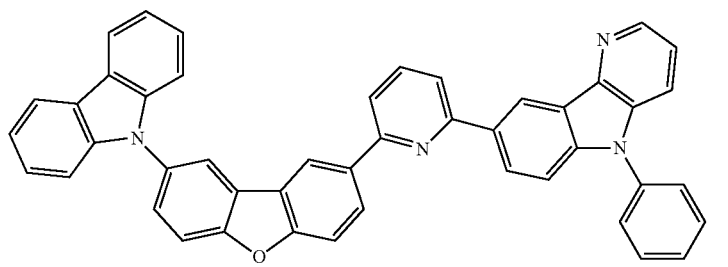
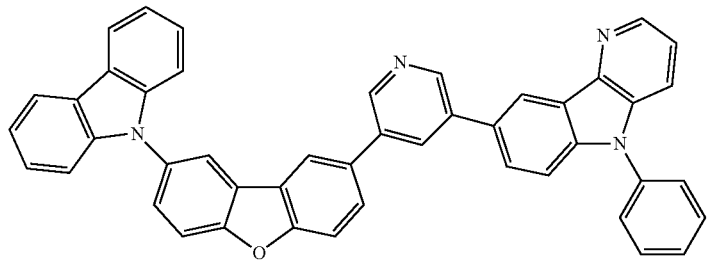
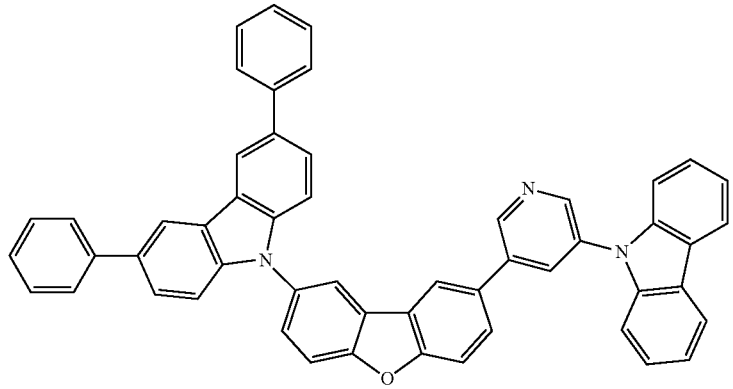
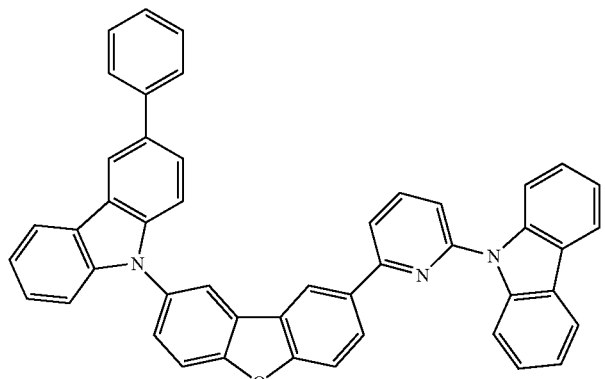
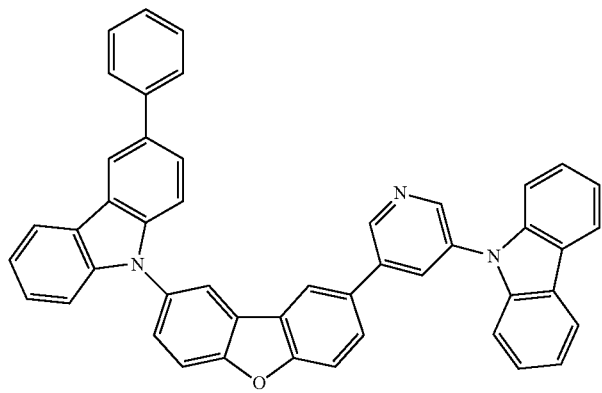

-continued
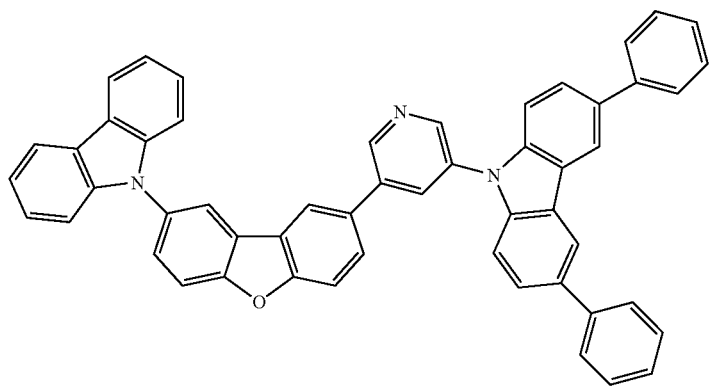
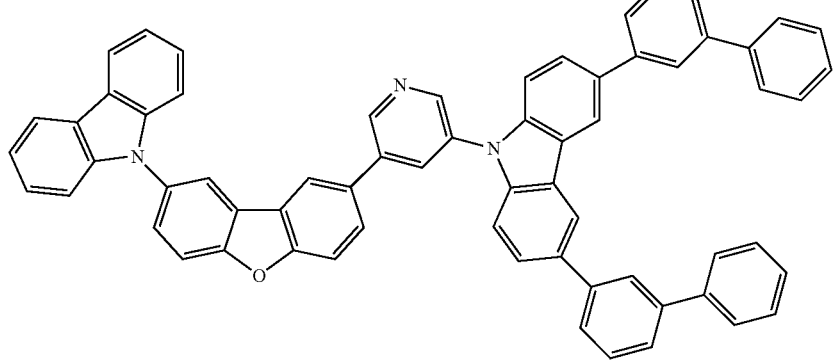
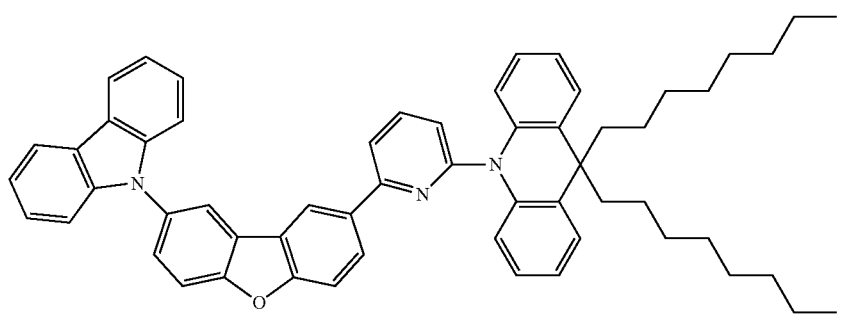
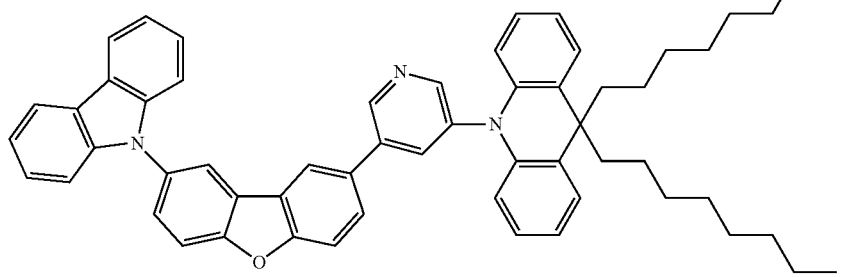
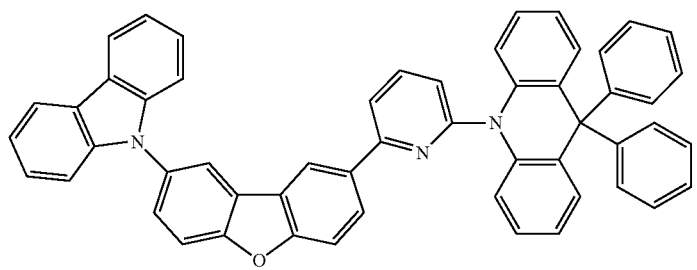

-continued
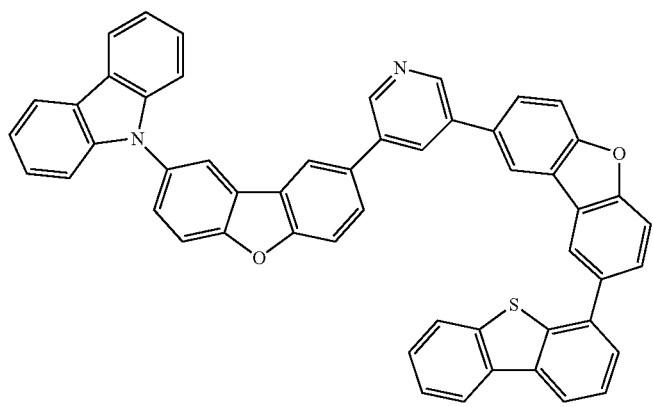
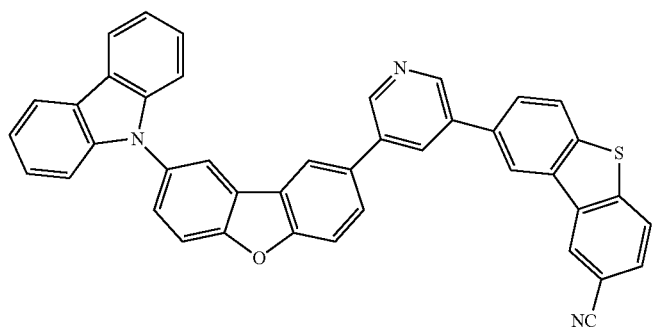
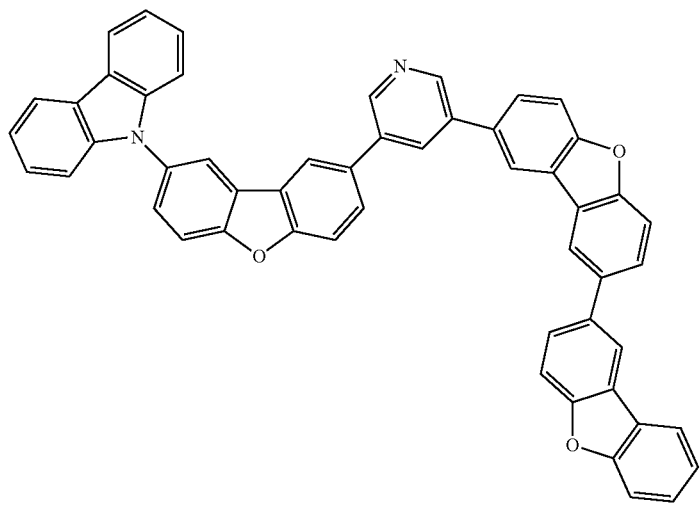
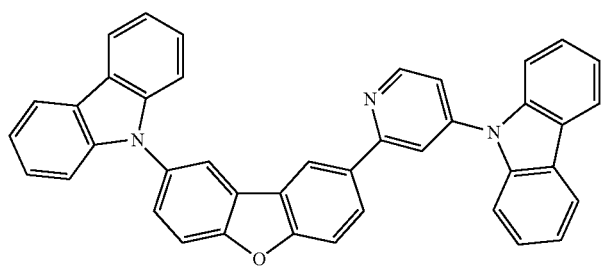

-continued
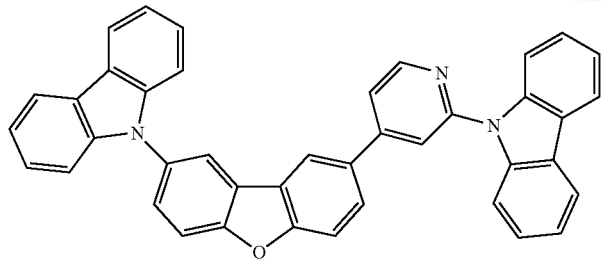
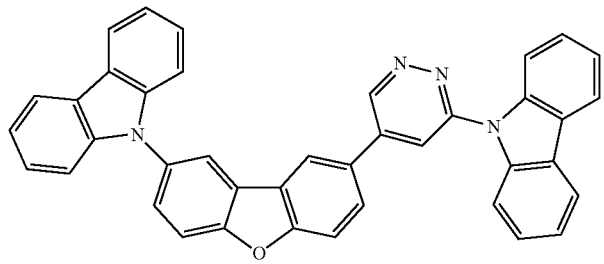
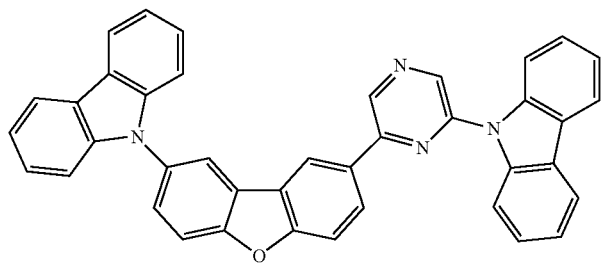
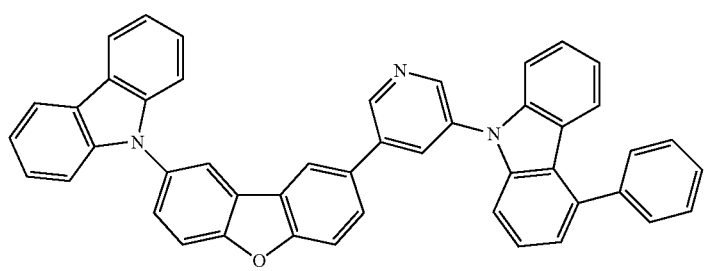
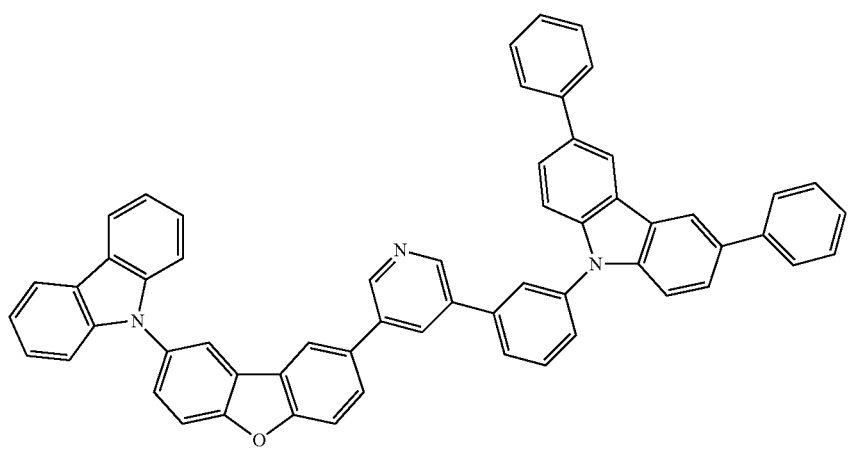

-continued
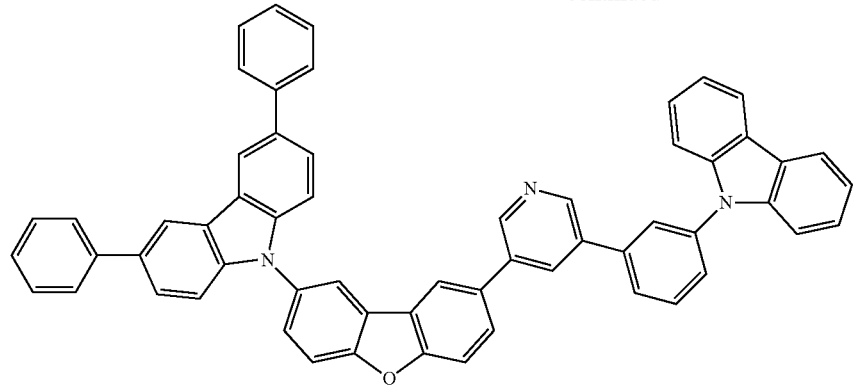
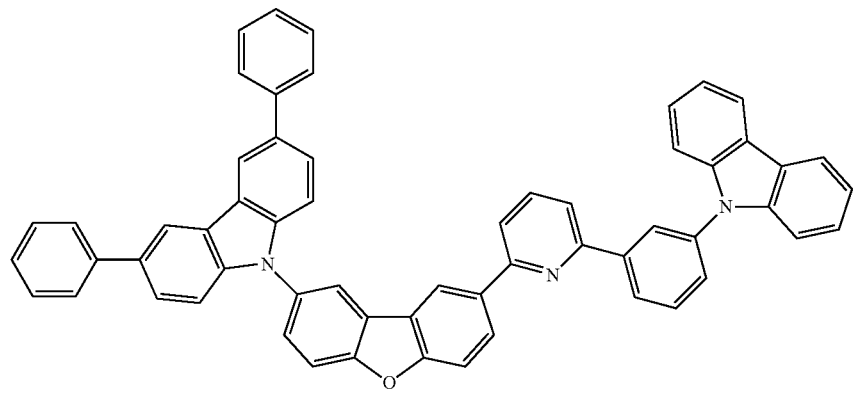
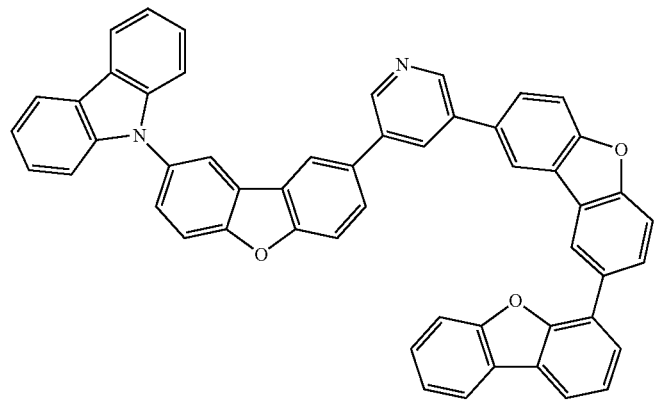
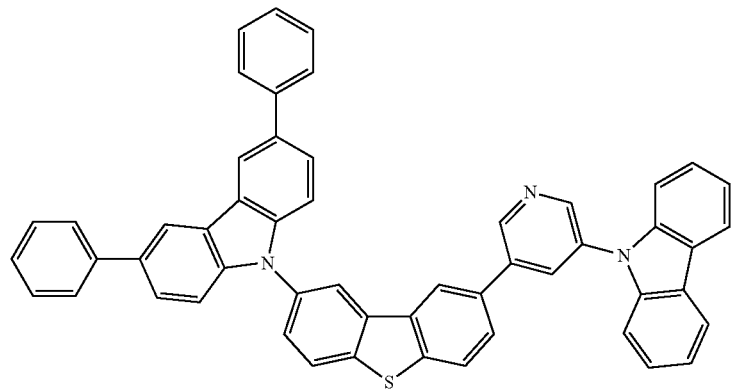

-continued

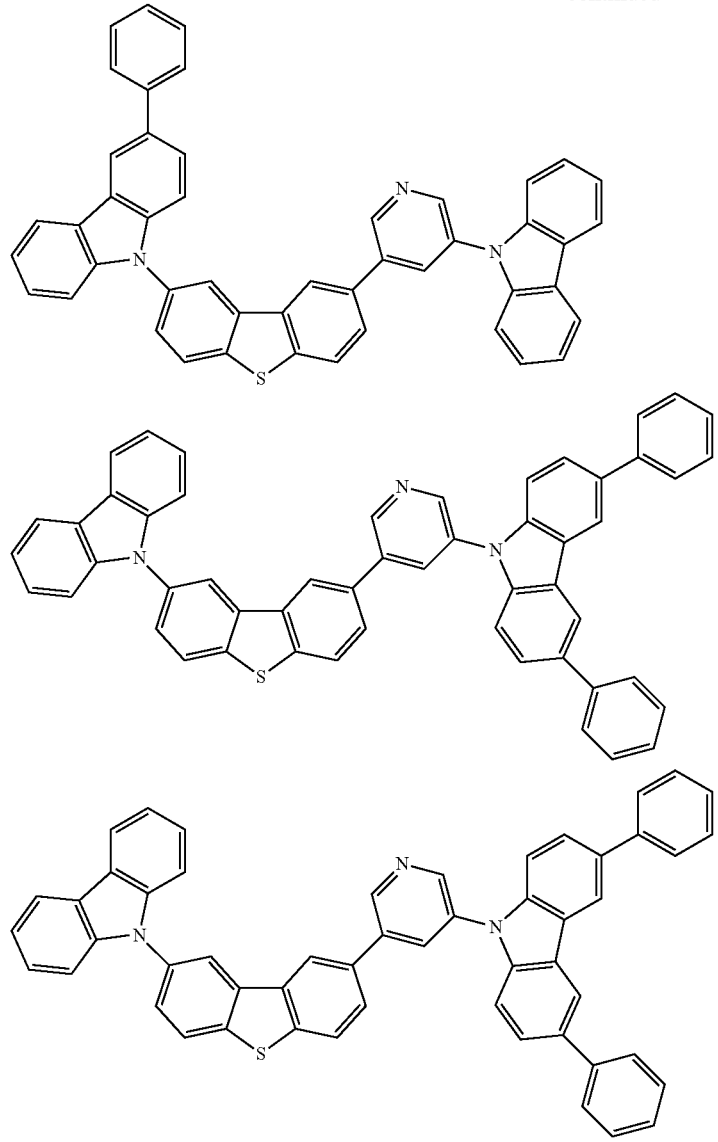

The nitrogen-containing heteroaromatic compound according to the invention may suitably be used as a material for forming an organic thin film layer that forms an organic EL device.

The material for an organic EL device according to the invention may preferably be used as a material for a phosphorescent organic EL device (particularly a blue phosphorescent device). The material for an organic EL device according to the invention is particularly preferable as a material for forming an emitting layer of a phosphorescent organic EL device, a layer (e.g., hole barrier layer or electron barrier layer) adjacent to the emitting layer, or the like.

The organic EL device according to the invention is described below.

The organic EL device according to the invention includes an anode, a cathode, and one or more organic thin film layers that are provided between the anode and the cathode and include an emitting layer. At least one organic thin film layer among the one or more organic thin film layers includes the material for an organic EL device according to the invention.

FIG. 1 is a schematic view illustrating the layer configuration of an organic EL device according to one embodiment of the invention.

An organic EL device 1 has a configuration in which an anode 20, a hole-transporting region 30, a phosphorescent emitting layer 40, an electron-transporting region 50, and a cathode 60 are sequentially stacked on a substrate 10. The hole-transporting region 30 refers to a hole-transporting layer, a hole-injecting layer, and the like. The electron-transporting region 50 refers to an electron-transporting layer, an electron-injecting layer, and the like. The hole-transporting layer and the like need not necessarily be formed, but it is preferable to form one or more hole-transporting layers and the like. In the organic EL device 1, each organic layer included in the hole-transporting region 30, the phosphorescent emitting layer 40, and each organic layer included in the electron-transporting region 50 are organic thin film layers. At least one organic thin film layer among these organic thin film layers includes the material for an organic EL device according to the invention. This makes it possible to reduce the driving voltage of the organic EL device.

The content of the material for an organic EL device according to the invention in the at least one organic thin film layer is preferably 1 to 100 wt %.

In the organic EL device according to the invention, it is preferable that the phosphorescent emitting layer 40 include the material for an organic EL device according to the invention. It is particularly preferable to use the material for an organic EL device according to the invention as a host material for the emitting layer. Since the material according to the invention has a sufficiently high triplet energy, the triplet energy of a phosphorescent dopant material can be efficiently confined in the emitting layer even when using a blue phosphorescent dopant material. Note that the material according to the invention may also be used for an emitting layer that emits light (e.g., green to red) having a wavelength longer than that of blue light.

The phosphorescent emitting layer includes a phosphorescent material (phosphorescent dopant). Examples of the phosphorescent dopant include metal complex compounds. It is preferable to use a compound that includes a metal atom selected from Ir, Pt, Os, Au, Cu, Re, and Ru, and a ligand. It is preferable that the ligand have an orthometal bond.

It is preferable that the phosphorescent dopant be a compound that includes a metal atom selected from Ir, Os, and Pt, more preferably a metal complex such as an iridium complex, an osmium complex, or a platinum complex, still more preferably an iridium complex or a platinum complex, and most preferably an orthometalated iridium complex, since the external quantum efficiency of the device can be improved due to high phosphorescence quantum yield. These dopants may be used either alone or in combination.

The concentration of the phosphorescent dopant in the phosphorescent emitting layer is not particularly limited, but is preferably 0.1 to 30 wt %, and still more preferably 0.1 to 20 wt %.

It is also preferable to use the material according to the invention for a layer adjacent to the phosphorescent emitting layer 40. For example, when a layer (anode-side layer adjacent to the phosphorescent emitting layer) that includes the material according to the invention is formed between the hole-transporting region 30 and the phosphorescent emitting layer 40 included in the device illustrated in FIG. 1, the layer that includes the material according to the invention functions as an electron barrier layer or an exciton blocking layer.

When a layer (cathode-side layer adjacent to the phosphorescent emitting layer) that includes the material according to the invention is formed between the phosphorescent emitting layer 40 and the electron-transporting region 50, the layer that includes the material according to the invention functions as a hole barrier layer or an exciton blocking layer.

Note that the term "barrier layer (blocking layer)" used herein refers to a layer that functions as a carrier migration barrier or an exciton diffusion barrier. An organic layer for preventing leakage of electrons from the emitting layer to the hole-transporting region may be referred to as "electron barrier layer", and an organic layer for preventing leakage of holes from the emitting layer to the electron-transporting region may be referred to as "hole barrier layer". An organic layer for preventing diffusion of triplet excitons generated in the emitting layer into a peripheral layer that has a triplet energy level lower than that of the emitting layer may be referred to as "exciton blocking layer (triplet barrier layer)".

The material according to the invention may also be used for a layer adjacent to the phosphorescent emitting layer 40 and another organic thin film layer that is bonded to the layer adjacent to the phosphorescent emitting layer 40.

When forming two or more emitting layers, the material according to the invention may suitably be used for forming a space layer that is formed between the emitting layers.

Figure 2:
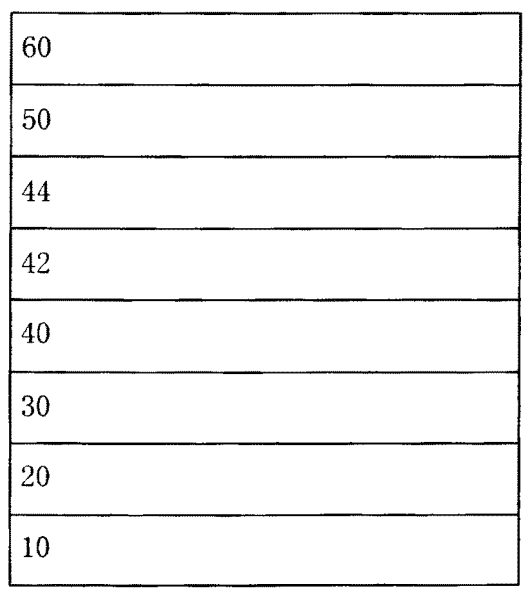
FIG. 2 is a view illustrating an organic EL device according to another embodiment of the invention.

FIG. 2 is a schematic view illustrating the layer configuration of an organic EL device according to another embodiment of the invention.

An organic EL device 2 illustrated in FIG. 2 is an example of a hybrid organic EL device in which a phosphorescent emitting layer and a fluorescent emitting layer are stacked.

The organic EL device 2 is configured in the same manner as the organic EL device 1, except that a space layer 42 and a fluorescent emitting layer 44 are formed between the phosphorescent emitting layer 40 and the electron-transporting region 50. When the phosphorescent emitting layer 40 and the fluorescent emitting layer 44 are stacked, the space layer 42 may be provided between the fluorescent emitting layer 44 and the phosphorescent emitting layer 40 so that excitons formed in the phosphorescent emitting layer 40 are not diffused into the fluorescent emitting layer 44. The material according to the invention can function as the space layer due to high triplet energy.

The organic EL device 2 emits white light when the phosphorescent emitting layer is a yellow emitting layer, and the fluorescent emitting layer is a blue emitting layer, for example. Although an example in which one phosphorescent emitting layer and one fluorescent emitting layer are formed has been described above, two or more phosphorescent emitting layers and/or two or more fluorescent emitting layers may be formed. The number of phosphorescent emitting layers and the number of fluorescent emitting layers may be appropriately set depending on the application (e.g., illumination (lighting) or display). For example, when forming a full-color emitting device by utilizing a white emitting device and a color filter, it may be preferable that the white emitting device include layers that differ in emission wavelength region (e.g., red, green, and blue (RGB), or red, green, blue, and yellow (RGBY)) from the viewpoint of color rendering properties.

Various known configurations may be employed for the organic EL device according to the invention in addition to (instead of) the above configurations. Light emitted from the emitting layer may be outcoupled through the anode and/or the cathode.

Electron Donor Dopant and Organic Metal Complex

It is preferable that the organic EL device according to the invention include at least one of an electron donor dopant and an organic metal complex in the interface region between the cathode and the organic thin film layer.

The above configuration makes it possible to improve the luminance and the lifetime of the organic EL device.

The electron donor dopant may be at least one metal or compound selected from alkali metals, alkali metal compounds, alkaline-earth metals, alkaline-earth metal compounds, rare-earth metals, rare-earth metal compounds, and the like.

The organic metal complex may be at least one organic metal complex selected from alkali metal-containing organic metal complexes, alkaline-earth metal-containing organic metal complexes, rare-earth metal-containing organic metal complexes, and the like.

Examples of the alkali metals include lithium (Li) (work function: 2.93 eV), sodium (Na) (work function: 2.36 eV), potassium (K) (work function: 2.28 eV), rubidium (Rb)

(work function: 2.16 eV), cesium (Cs) (work function: 1.95 eV), and the like. It is particularly preferable to use an alkali metal having a work function of 2.9 eV or less. Among these, K, Rb, and Cs are preferable, Rb and Cs are more preferable, and Cs is most preferable.

Examples of the alkaline-earth metals include calcium (Ca) (work function: 2.9 eV), strontium (Sr) (work function: 2.0 to 2.5 eV), barium (Ba) (work function: 2.52 eV), and the like. It is particularly preferable to use an alkaline-earth metal having a work function of 2.9 eV or less.

Examples of the rare-earth metals include scandium (Sc), yttrium (Y), cerium (Ce), terbium (Tb), ytterbium (Yb), and the like. It is particularly preferable to use a rare-earth metal having a work function of 2.9 eV or less.

Since the above preferable metals exhibit a particularly high reducing capability, the luminance and the lifetime of the organic EL device can be improved by adding a relatively small amount of such a metal to the electron-injecting region.

Examples of the alkali metal compounds include alkali metal oxides such as lithium oxide ($Li_2O$), cesium oxide ($Cs_2O$), and potassium oxide ($K_2O$), alkali metal halides such as lithium fluoride (LiF), sodium fluoride (NaF), cesium fluoride (CsF), and potassium fluoride (KF), and the like. Among these, lithium fluoride (LiF), lithium oxide ($Li_2O$), and sodium fluoride (NaF) are preferable.

Examples of the alkaline-earth metal compounds include barium oxide (BaO), strontium oxide (SrO), calcium oxide (CaO), mixtures thereof (e.g., ($Ba_xSr_{1-x}O$) (0<x<1) and ($Ba_xCa_{1-x}O$) (0<x<1)), and the like. Among these, BaO, SrO, and CaO are preferable.

Examples of the rare-earth metal compounds include ytterbium fluoride ($YbF_3$), scandium fluoride ($ScF_3$), scandium oxide ($ScO_3$), yttrium oxide ($Y_2O_3$), cerium oxide ($Ce_2O_3$), gadolinium fluoride ($GdF_3$), terbium fluoride ($TbF_3$), and the like. Among these, $YbF_3$, $ScF_3$, and $TbF_3$ are preferable.

The organic metal complex is not particularly limited as long as the organic metal complex includes at least one of an alkali metal ion, an alkaline-earth metal ion, and rare-earth metal ion as the metal ion. Examples of a preferable ligand include, but are not limited to, quinolinol, benzoquinolinol, acridinol, phenanthridinol, hydroxyphenyloxazole, hydroxyphenylthiazole, hydroxydiaryloxadiazoles, hydroxydiarylthiadiazoles, hydroxyphenylpyridine, hydroxyphenylbenzimidazole, hydroxybenzotriazole, hydroxyfurborane, bipyridyl, phenanthroline, phthalocyanine, porphyrin, cyclopentadiene, β-diketones, azomethines, derivatives thereof, and the like.

The electron donor dopant and the organic metal complex are preferably deposited (formed) in the interface region in the shape of a layer or islands. It is preferable to deposit an organic material (i.e., an emitting material or an electron-injecting material that forms the interface region) while depositing at least one of the electron donor dopant and the organic metal complex by resistance heating deposition so that at least one of the electron donor dopant and the organic metal complex is dispersed in the organic material. The dispersion concentration (i.e., the molar ratio of the organic substance to the electron donor dopant and/or the organic metal complex) is normally 100:1 to 1:100, and preferably 5:1 to 1:5.

When depositing (forming) at least one of the electron donor dopant and the organic metal complex in the shape of a layer, the emitting material or the electron-injecting material (i.e., the organic layer at the interface) is deposited (formed) in the shape of a layer, and at least one of the electron donor dopant and the organic metal complex is deposited by resistance heating deposition to a thickness of preferably 0.1 to 15 nm.

When depositing (forming) at least one of the electron donor dopant and the organic metal complex in the shape of islands, the emitting material or the electron-injecting material (i.e., the organic layer at the interface) is deposited (formed) in the shape of islands, and at least one of the electron donor dopant and the organic metal complex is deposited by resistance heating deposition to a thickness of preferably 0.05 to 1 nm.

The molar ratio of the main component to the electron donor dopant and/or the organic metal complex in the organic EL device according to the invention is preferably 5:1 to 1:5, and more preferably 2:1 to 1:2.

The configuration of the organic EL device according to the invention other than the layer formed using the material for an organic EL device according to the invention is not particularly limited. The layers other than the layer formed using the material for an organic EL device according to the invention may be formed using a known material and the like. The layers included in the organic EL device 1 according to the embodiment of the invention are briefly described below. Note that materials that may be used the organic EL device according to the invention are not limited to the following materials.

Substrate

A glass sheet, a polymer sheet, or the like may be used as the substrate.

Examples of a material for forming the glass sheet include soda lime glass, barium-strontium-containing glass, lead glass, aluminosilicate glass, borosilicate glass, barium borosilicate glass, quartz, and the like. Examples of a material for forming the polymer sheet include polycarbonate, acryl, polyethylene terephthalate, polyethersulfone, polysulfone, and the like.

Anode

The anode is formed of a conductive material, for example. It is preferable to use a conductive material having a work function of more than 4 eV.

Examples of the conductive material include carbon, aluminum, vanadium, iron, cobalt, nickel, tungsten, silver, gold, platinum, palladium, alloys thereof, metal oxides (e.g., tin oxide and indium oxide) used for an ITO substrate and an NESA substrate, organic conductive resins (e.g., polythiophene and polypyrrole), and the like.

The anode may optionally be formed by two or more layers.

Cathode

The cathode is formed of a conductive material, for example. It is preferable to use a conductive material having a work function of less than 4 eV.

Examples of the conductive material include, but are not limited to, magnesium, calcium, tin, lead, titanium, yttrium, lithium, ruthenium, manganese, aluminum, lithium fluoride, alloys thereof, and the like.

Examples of the alloys include, but are not limited to, a magnesium/silver alloy, a magnesium/indium alloy, a lithium/aluminum alloy, and the like. The alloy ratio is appropriately selected depending on the temperature of the deposition source, the atmosphere, the degree of vacuum, and the like.

The cathode may optionally be formed by two or more layers. The cathode may be formed by forming a thin film of the conductive material by deposition, sputtering, or the like.

When outcoupling light from the emitting layer through the cathode, it is preferable that the cathode have a light transmittance of more than 10%. The sheet resistance of the cathode is preferably several hundred Ω/square or less. The thickness of the cathode is normally 10 nm to 1 μm, and preferably 50 to 200 nm.

Emitting Layer

When forming the phosphorescent emitting layer using a material other than the material for an organic EL device according to the invention, a known material may be used as the material for forming the phosphorescent emitting layer. Japanese Patent Application No. 2005-517938 and the like disclose specific examples of the materials for forming the phosphorescent emitting layer.

The organic EL device according to the invention may include a fluorescent emitting layer (see FIG. 2). The fluorescent emitting layer may be formed using a known material.

The emitting layer may have a double-host (host-cohost) configuration. More specifically, the carrier balance within the emitting layer may be adjusted by incorporating an electron-transporting host and a hole-transporting host in the emitting layer.

The emitting layer may also have a double-dopant configuration. When the emitting layer includes two or more dopant materials having a high quantum yield, each dopant emits light. For example, a yellow emitting layer may be implemented by codepositing a host, a red dopant, and a green dopant.

The emitting layer may include only a single layer, or may have a stacked structure. When the emitting layer has a stacked structure, the recombination region can be concentrated at the interface between the stacked layers due to accumulation of electrons and holes. This makes it possible to improve the quantum efficiency.

Hole-Injecting Layer and Hole-Transporting Layer

The hole-injecting/transporting layer is a layer that assists injection of holes into the emitting layer, and transports holes to the emitting region. The hole-injecting/transporting layer exhibits a high hole mobility, and normally has a low ionization energy of 5.6 eV or less.

It is preferable to form the hole-injecting/transporting layer using a material that transports holes to the emitting layer at a low field intensity. It is more preferable to use a material having a hole mobility of at least $10^{-4}$ cm$^2$/V·s when an electric field of $10^4$ to $10^6$ V/cm is applied, for example.

Specific examples of the material for forming the hole-injecting/transporting layer include triazole derivatives (see U.S. Pat. No. 3,112,197, for example), oxadiazole derivatives (see U.S. Pat. No. 3,189,447, for example), imidazole derivatives (see JP-B-37-16096, for example), polyarylalkane derivatives (see U.S. Pat. No. 3,615,402, U.S. Pat. No. 3,820,989, U.S. Pat. No. 3,542,544, JP-B-45-555, JP-B-51-10983, JP-A-51-93224, JP-A-55-17105, JP-A-56-4148, JP-A-55-108667, JP-A-55-156953, and JP-A-56-36656, for example), pyrazoline derivatives and pyrazolone derivatives (U.S. Pat. No. 3,180,729, U.S. Pat. No. 4,278,746, JP-A-55-88064, JP-A-55-88065, JP-A-49-105537, JP-A-55-51086, JP-A-56-80051, JP-A-56-88141, JP-A-57-45545, JP-A-54-112637, and JP-A-55-74546, for example), phenylenediamine derivatives (U.S. Pat. No. 3,615,404, JP-B-51-10105, JP-B-46-3712, JP-B-47-25336, and JP-B-54-119925, for example), arylamine derivatives (U.S. Pat. No. 3,567,450, U.S. Pat. No. 3,240,597, U.S. Pat. No. 3,658,520, U.S. Pat. No. 4,232,103, U.S. Pat. No. 4,175,961, U.S. Pat. No. 4,012,376, JP-B-49-35702, JP-B-39-27577, JP-A-55-144250, JP-A-56-119132, JP-A-56-22437, and West German Patent No. 1,110,518, for example), amino-substituted chalcone derivatives (U.S. Pat. No. 3,526,501, for example), oxazole derivatives (see U.S. Pat. No. 3,257,203, for example), styrylanthracene derivatives (JP-A-56-46234, for example), fluorenone derivatives (JP-A-54-110837, for example), hydrazone derivatives (U.S. Pat. No. 3,717,462, JP-A-54-59143, JP-A-55-52063, JP-A-55-52064, JP-A-55-46760, JP-A-57-11350, JP-A-57-148749, and JP-A-2-311591, for example), stilbene derivatives (JP-A-61-210363, JP-A-61-228451, JP-A-61-14642, JP-A-61-72255, JP-A-62-47646, JP-A-62-36674, JP-A-62-10652, JP-A-62-30255, JP-A-60-93455, JP-A-60-94462, JP-A-60-174749, and JP-A-60-175052, for example), silazane derivatives (U.S. Pat. No. 4,950,950, for example), polysilane compounds (JP-A-2-204996, for example), aniline copolymers (JP-A-2-282263, for example), and the like.

An inorganic compound (e.g., p-type Si or p-type SiC) may also be used as the hole-injecting material.

A crosslinkable material may be used as the material for forming the hole-injecting/transporting layer. Examples of the crosslinkable hole-injecting/transporting layer include layers obtained by insolubilizing crosslinkable materials disclosed in Chem. Mater. 2008, 20, pp. 413-422, Chem. Mater. 2011, 23 (3), pp. 658-681, WO2008/108430, WO2009/102027, WO2009/123269, WO2010/016555, WO2010/018813, and the like by applying heat, light, and the like.

Electron-Injecting Layer and Electron-Transporting Layer

The electron injecting/transporting layer is a layer that assists injection of electrons into the emitting layer, and transports electrons to the emitting region. The electron injecting/transporting layer exhibits high electron mobility.

Since an organic EL device is designed so that emitted light is reflected by an electrode (e.g., cathode), light that is outcoupled directly through the anode interferes with light that is outcoupled after being reflected by the electrode. The thickness of the electron-injecting/transporting layer is appropriately selected within the range of several nanometers to several micrometers in order to efficiently utilize the above interference effect. In particular, when the electron-injecting/transporting layer has a large thickness, it is preferable that the electron mobility be at least $10^{-5}$ cm$^2$/Vs or more at an applied electric field of $10^4$ to $10^6$ V/cm in order to prevent an increase in voltage.

A heteroaromatic compound having one or more heteroatoms in the molecule is preferably used as an electron-transporting material used for forming the electron-injecting/transporting layer. It is particularly preferable to use a nitrogen-containing ring derivative. An aromatic compound having a nitrogen-containing 6-membered or 5-membered ring skeleton, or a fused aromatic compound having a nitrogen-containing 6-membered or 5-membered ring skeleton is preferable as the nitrogen-containing ring derivative. Examples of such compounds include compounds that include a pyridine ring, a pyrimidine ring, a triazine ring, a benzimidazole ring, a phenanthroline ring, a quinazoline ring, or the like in the skeleton.

An organic layer that exhibits semiconductivity may be formed by doping (n) with a donor material and doping (p) with an acceptor material. Typical examples of N-doping include doping an electron-transporting material with a metal such as Li or Cs, and typical examples of P-doping include doping a hole-transporting material with an acceptor material such as F4TCNQ (see Japanese Patent No. 3695714, for example).

Each layer of the organic EL device according to the invention may be formed by a known method, e.g., a dry film-forming method such as vacuum deposition, sputtering, a plasma method, or ion plating, or a wet film-forming method such as spin coating, dipping, or flow coating.

The thickness of each layer is not particularly limited as long as each layer has an appropriate thickness. If the thickness of each layer is too large, a high applied voltage may be required to obtain constant optical output, so that the efficiency may deteriorate. If the thickness of each layer is too small, pinholes or the like may occur, so that sufficient luminance may not be obtained even if an electric field is applied. The thickness of each layer is normally 5 nm to 10 μm, and preferably 10 nm to 0.2 μm.

EXAMPLES

Nitrogen-Containing Heteroaromatic Compound

Synthesis Example 1

Synthesis of Compound A (1) Synthesis of Intermediate A

An intermediate A was synthesized by the following procedure.

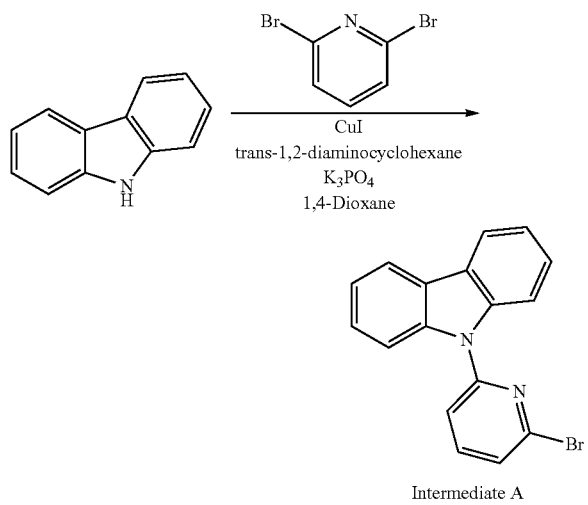

Intermediate A 16.7 g (100 mmol) of carbazole, 23.7 g (100 mmol) of 2,6-dibromopyridine, 19.0 g (100 mmol) of copper iodide, 11.4 g (100 mmol) of trans-1,2-cyclohexanediamine, and 42.4 g (200 mmol) of tripotassium phosphate were added to 200 ml of dehydrated 1,4-dioxane in an argon atmosphere, and the mixture was refluxed for 72 hours with heating and stirring. The reaction solution was concentrated under reduced pressure. After the addition of 500 ml of toluene to the residue, the mixture was heated to 120° C., and insoluble material was filtered off. The filtrate was concentrated under reduced pressure, and the residue was purified by silica gel column chromatography (hexane/toluene=4/1) to obtain 9.7 g (yield: 30%) of the intermediate A as a white solid.

(2) Synthesis of Intermediate C

An intermediate C was synthesized by the following procedure.

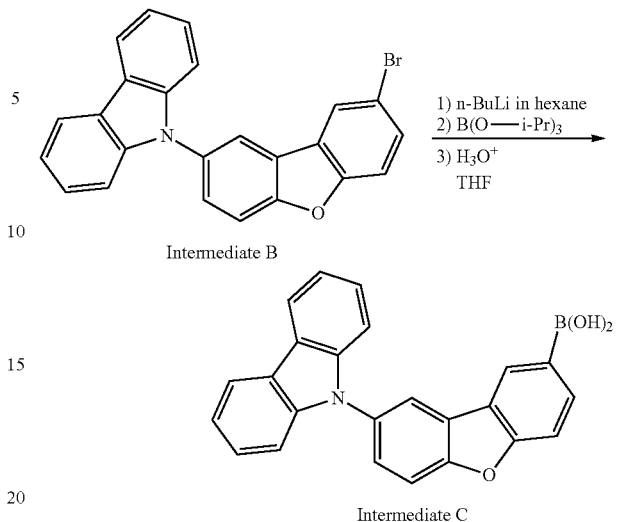

50 ml of dehydrated THF was added to 4.1 g (10 mmol) of an intermediate B (synthesized in accordance with the method described in WO2009/008100) in an argon atmosphere, and the mixture was stirred at −70° C. After the addition of 6.25 ml of a 1.6 M n-butyllithium solution (in n-hexane) dropwise to the mixture, the mixture was stirred at −70° C. for 1 hour. After the addition of 5.6 g (30 mmol) of triisopropyl borate, the mixture was stirred at −70° C. for 1 hour, and then stirred at room temperature for 5 hours. After concentrating the reaction mixture, 400 ml of dichloromethane and 50 ml of 1 N hydrochloric acid were added to the concentrate. The mixture was stirred and cooled in an ice water bath for 1 hour. The organic phase was isolated preparatively, and dried over anhydrous magnesium sulfate, and the filtrate was concentrated. The resulting solid was suspended in and washed with a mixture of hexane and toluene to obtain 2.3 g (yield: 60%) of the intermediate C as a white solid.

(3) Synthesis of Compound A

A compound A was synthesized by the following procedure.

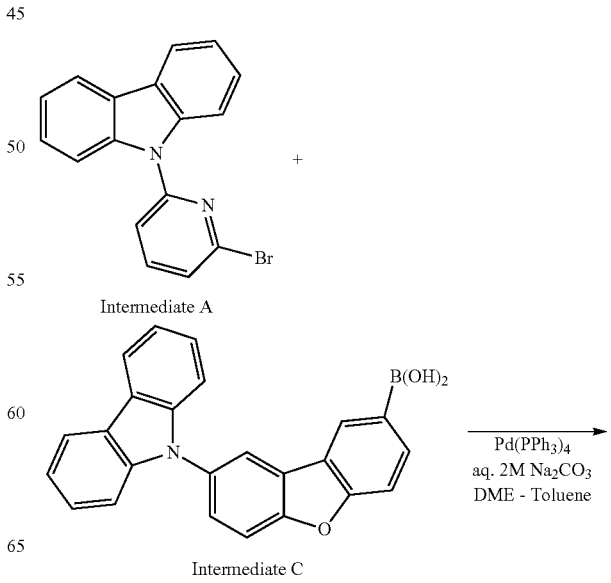

-continued

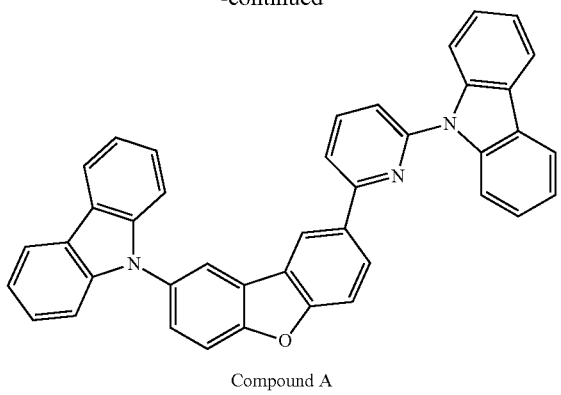

Compound A 3.2 g (10 mmol) of the intermediate A, 3.8 g (10 mmol) of the intermediate C, 10 ml of a 2 M sodium carbonate aqueous solution, 10 ml of 1,2-dimethoxyethane (DME), and 30 ml of toluene were mixed in an argon atmosphere. After the addition of 0.34 g (0.30 mmol) of tetrakis(triphenylphosphine)palladium, the mixture was refluxed for 8 hours with heating and stirring. The reaction solution was concentrated under reduced pressure. After the addition of 500 ml of toluene to the residue, the mixture was heated to 120° C., and insoluble material was filtered off. The filtrate was concentrated under reduced pressure, and the residue was purified by silica gel column chromatography (hexane/dichloromethane=3/1) to obtain 4.3 g (yield: 75%) of the compound A as a white solid.

It was found by FD-MS analysis that the molecular weight of the compound A was 575, and the value m/e was 575.

Synthesis Example 2

Synthesis of Compound B (1) Synthesis of Intermediate D

An intermediate D was synthesized by the following procedure.

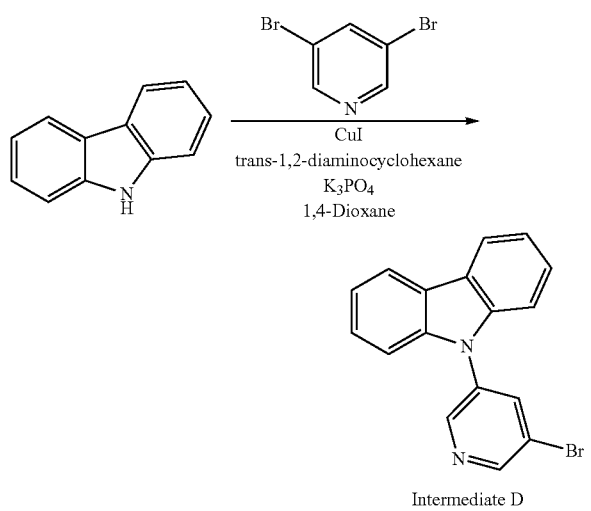

16.7 g (100 mmol) of carbazole, 23.7 g (100 mmol) of 3,5-dibromopyridine, 19.0 g (100 mmol) of copper iodide, 11.4 g (100 mmol) of trans-1,2-cyclohexanediamine, and 42.4 g (200 mmol) of tripotassium phosphate were added to 200 ml of dehydrated 1,4-dioxane in an argon atmosphere, and the mixture was refluxed for 96 hours with heating and stirring. The reaction solution was concentrated under reduced pressure. After the addition of 500 ml of toluene to the residue, the mixture was heated to 120° C., and insoluble material was filtered off. The filtrate was concentrated under reduced pressure, and the residue was purified by silica gel column chromatography (hexane/toluene=4/1) to obtain 6.8 g (yield: 21%) of the intermediate D as a white solid.

(2) Synthesis of Compound B

A compound B was synthesized by the following procedure.

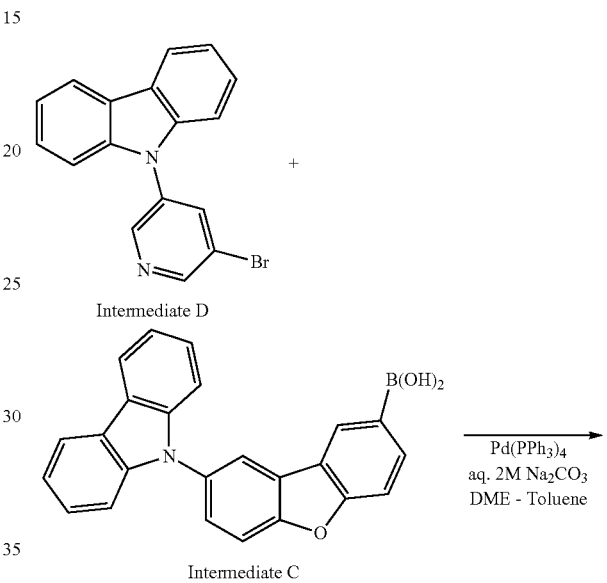

Compound B 3.2 g (10 mmol) of the intermediate D, 3.8 g (10 mmol) of the intermediate C (obtained in "(2) Synthesis of intermediate C" in Synthesis Example 1), 10 ml of a 2 M sodium carbonate aqueous solution, 10 ml of 1,2-dimethoxyethane (DME), and 30 ml of toluene were mixed in an argon atmosphere. After the addition of 0.34 g (0.30 mmol) of tetrakis(triphenylphosphine)palladium, the mixture was refluxed for 24 hours with heating and stirring. The reaction solution was concentrated under reduced pressure. After the addition of 500 ml of toluene to the residue, the mixture was heated to 120° C., and insoluble material was filtered off. The filtrate was concentrated under reduced pressure, and the residue was purified by silica gel column chromatography (hexane/dichloromethane=2/1) to obtain 3.2 g (yield: 55%) of the compound B as a white solid.

It was found by FD-MS analysis that the molecular weight of the compound B was 575, and the value m/e was 575.

The $^1$H-NMR measurement results are shown below.

$^1$H-NMR (400 MHz, CDCl$_3$) δ7.28-7.35 (4H, m), 7.37-7.46 (8H, m), 7.68 (1H, dd, J=2.0 Hz, 8.4 Hz), 7.78-7.84 (3H, m), 8.15-8.18 (6H, m), 8.21-8.22 (1H, m), 8.89 (1H, d, J=2.0 Hz), 9.03 (1H, d, J=2.0 Hz).

Synthesis Example 3

Synthesis of Compound C (1) Synthesis of Intermediate E

An intermediate E was synthesized by the following procedure.

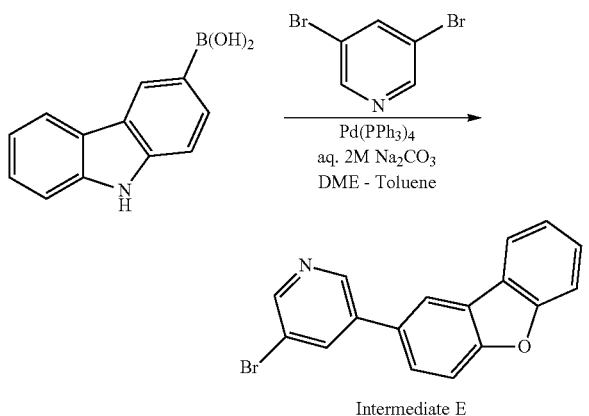

21.2 g (100 mmol) of dibenzofuran-2-boronic acid, 23.7 g (100 mmol) of 3,5-dibromopyridine, 100 ml of a 2 M sodium carbonate aqueous solution, 100 ml of 1,2-dimethoxyethane (DME), and 200 ml of toluene were mixed in an argon atmosphere. After the addition of 3.5 g (3 mmol) of tetrakis(triphenylphosphine)palladium, the mixture was refluxed for 48 hours with heating and stirring. The reaction solution was concentrated under reduced pressure. After the addition of 1000 ml of toluene to the residue, the mixture was heated to 120° C., and insoluble material was filtered off. The filtrate was concentrated under reduced pressure, and the residue was purified by silica gel column chromatography (hexane/dichloromethane=2/1) to obtain 13.9 g (yield: 43%) of the intermediate E as a white solid.

(2) Synthesis of Compound C

A compound C was synthesized by the following procedure.

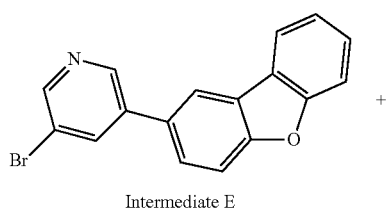

Intermediate E

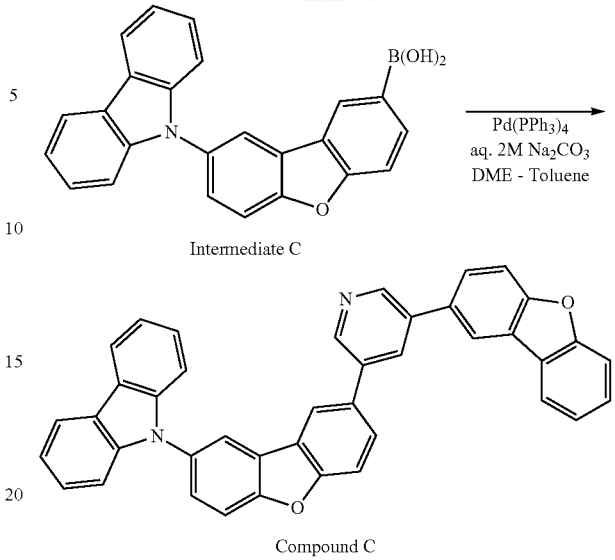

3.2 g (10 mmol) of the intermediate E, 3.8 g (10 mmol) of the intermediate C, 10 ml of a 2 M sodium carbonate aqueous solution, 10 ml of 1,2-dimethoxyethane (DME), and 30 ml of toluene were mixed in an argon atmosphere. After the addition of 0.34 g (0.30 mmol) of tetrakis(triphenylphosphine)palladium, the mixture was refluxed for 48 hours with heating and stirring. The reaction solution was concentrated under reduced pressure. After the addition of 500 ml of toluene to the residue, the mixture was heated to 120° C., and insoluble material was filtered off. The filtrate was concentrated under reduced pressure, and the residue was purified by silica gel column chromatography (hexane/dichloromethane=3/2) to obtain 2.6 g (yield: 45%) of the compound C as a white solid.

It was found by FD-MS analysis that the molecular weight of the compound C was 576, and the value m/e was 576.

Synthesis Example 4

Synthesis of Compound D (1) Synthesis of Intermediate F

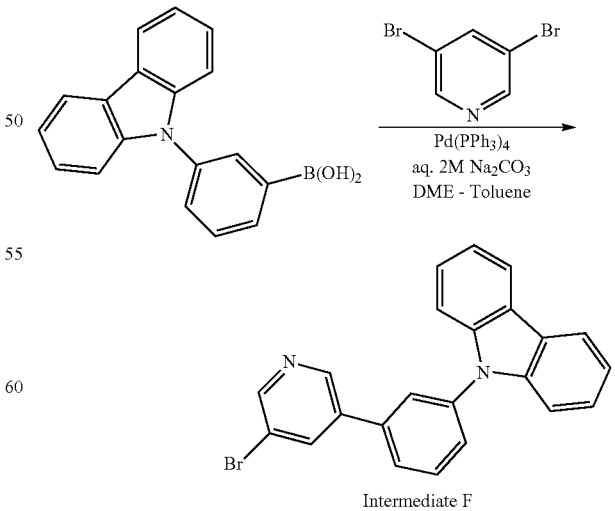

28.7 g (100 mmol) of 3-(N-carbazolyl)phenylboronic acid, 23.7 g (100 mmol) of 3,5-dibromopyridine, 100 ml of a 2 M sodium carbonate aqueous solution, 100 ml of 1,2-dimethoxyethane (DME), and 200 ml of toluene were mixed in an argon atmosphere. After the addition of 3.5 g (3 mmol) of tetrakis(triphenylphosphine)palladium, the mixture was refluxed for 36 hours with heating and stirring. The reaction solution was concentrated under reduced pressure. After the addition of 1000 ml of toluene to the residue, the mixture was heated to 120° C., and insoluble material was filtered off. The filtrate was concentrated under reduced pressure, and the residue was purified by silica gel column chromatography (hexane/ethyl acetate=4/1) to obtain 20.8 g (yield: 52%) of the intermediate F as a white solid.

(2) Synthesis of Compound D

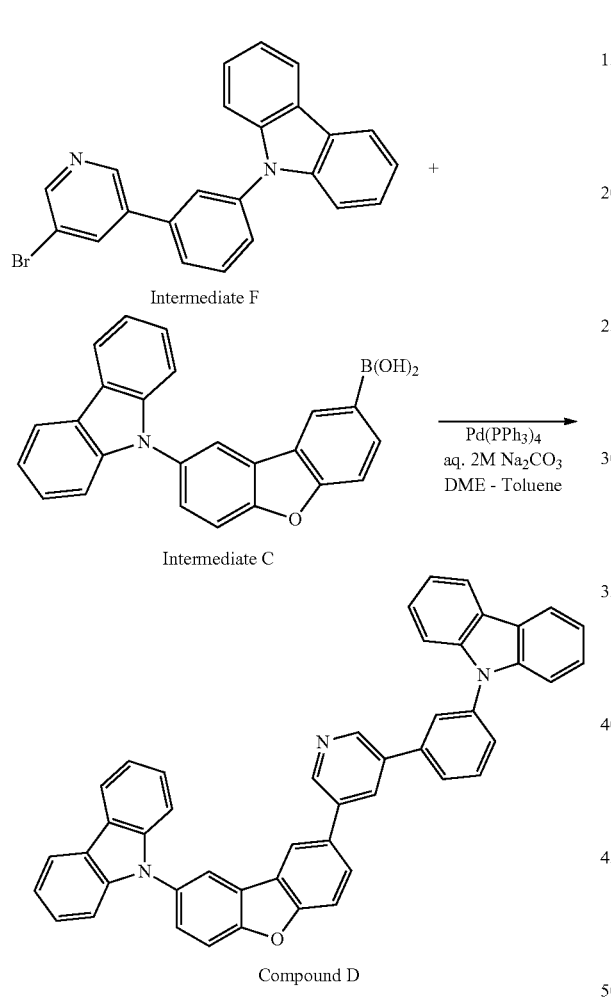

Intermediate F

Intermediate C

Compound D 3.9 g (10 mmol) of the intermediate F, 3.8 g (10 mmol) of the intermediate C, 10 ml of a 2 M sodium carbonate aqueous solution, 10 ml of 1,2-dimethoxyethane (DME), and 30 ml of toluene were mixed in an argon atmosphere. After the addition of 0.34 g (0.30 mmol) of tetrakis(triphenylphosphine)palladium, the mixture was refluxed for 24 hours with heating and stirring. The reaction solution was concentrated under reduced pressure. After the addition of 500 ml of toluene to the residue, the mixture was heated to 120° C., and insoluble material was filtered off. The filtrate was concentrated under reduced pressure, and the residue was purified by silica gel column chromatography (hexane/ethyl acetate=2/1) to obtain 4.6 g (yield: 71%) of the compound D as a white solid.

It was found by FD-MS analysis that the molecular weight of the compound D was 651, and the value m/e was 651.

The $^1$H-NMR measurement results are shown below.
$^1$H-NMR (400 MHz, CDCl$_3$) δ7.28-7.32 (4H, m), 7.36-7.47 (8H, m), 7.62-7.66 (2H, m), 7.71-7.82 (5H, m), 7.85-7.87 (1H, m), 8.12-8.17 (7H, m), 8.92 (2H, dd, J=2.0 Hz, 8.0 Hz).

Synthesis Example 5

Synthesis of Compound E (1) Synthesis of Intermediate G

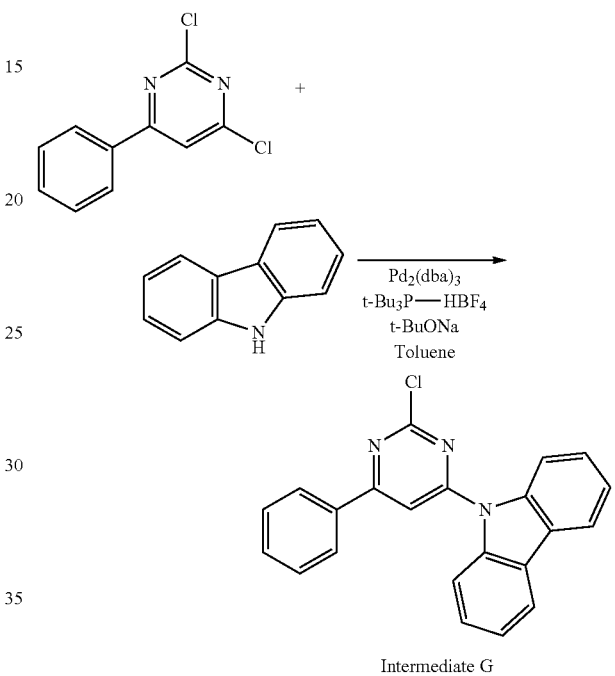

Intermediate G 9.0 g (40 mmol) of 2,4-dichloro-6-phenylpyrimidine (synthesized in accordance with the method described in J. Org. Chem., p. 7125, 2001), 6.7 g (40 mmol) of carbazole, 0.37 g (0.4 mmol) of tris(dibenzylideneacetone)dipalladium, 0.46 g (1.6 mmol) of tri-t-butylphosphonium tetrafluoroborate, 5.4 g (56 mmol) of sodium t-butoxide, and 100 ml of anhydrous toluene were sequentially mixed in an argon atmosphere, and the mixture was refluxed for 12 hours with heating and stirring. The reaction solution was concentrated under reduced pressure, and the residue was purified by silica gel column chromatography (hexane/dichloromethane=3/2) to obtain 5.0 g (yield: 35%) of an intermediate G as a white solid.

(2) Synthesis of Compound E

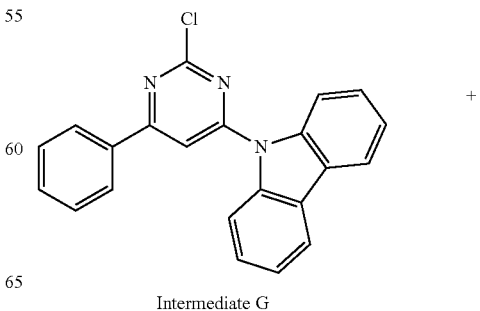

Intermediate G

-continued

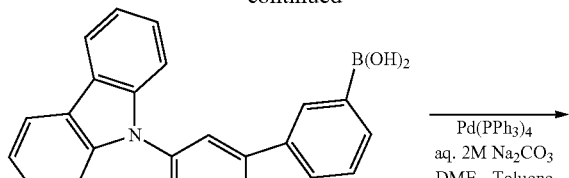

Intermediate C

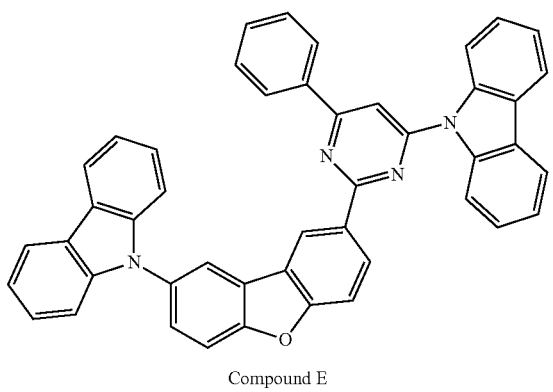

Compound E 3.6 g (10 mmol) of the intermediate G, 3.8 g (10 mmol) of the intermediate C, 10 ml of a 2 M sodium carbonate aqueous solution, 10 ml of 1,2-dimethoxyethane (DME), and 30 ml of toluene were mixed in an argon atmosphere. After the addition of 0.34 g (0.30 mmol) of tetrakis(triphenylphosphine)palladium, the mixture was refluxed for 24 hours with heating and stirring. The reaction solution was concentrated under reduced pressure. After the addition of 500 ml of toluene to the residue, the mixture was heated to 120° C., and insoluble material was filtered off. The filtrate was concentrated under reduced pressure, and the residue was purified by silica gel column chromatography (hexane/toluene=2/1), and recrystallized from toluene to obtain 1.6 g (yield: 25%) of the compound E as a white solid.

It was found by FD-MS analysis that the molecular weight of the compound E was 652, and the value m/e was 652.

Organic EL Device

Example 1

A glass substrate (25×75×1.1 mm, manufactured by Geomatec) provided with an ITO transparent electrode was subjected to ultrasonic cleaning for 5 minutes in isopropyl alcohol, and then subjected to ultraviolet (UV) ozone cleaning for 30 minutes.

The glass substrate thus cleaned was mounted on a substrate holder of a vacuum deposition system, and a compound I was deposited to a thickness of 20 nm on the surface of the glass substrate on which the transparent electrode line was formed so as to cover the transparent electrode to obtain a hole-injecting layer. A compound II was deposited on the resulting film to a thickness of 60 nm to obtain a hole-transporting layer.

The compound A obtained in Synthesis Example 1 (phosphorescent host material) and a compound D-1 (phosphorescent emitting material) were codeposited on the hole-transporting layer to a thickness of 50 nm to obtain a phosphorescent emitting layer. The concentration of the compound A in the phosphorescent emitting layer was 80 mass %, and the concentration of the compound D-1 in the phosphorescent emitting layer was 20 mass %.

A compound H-1 was deposited on the phosphorescent emitting layer to a thickness of 10 nm to obtain an electron-transporting layer. A compound III was deposited on the electron-transporting layer to a thickness of 10 nm to obtain an electron-transporting layer. LiF (thickness: 1 nm) and metal Al (thickness: 80 nm) were sequentially stacked on the electron-transporting layer to obtain a cathode. Note that the LiF electrode (electron-injecting electrode) was formed at a rate of 1 angstrom/min.

Compound I

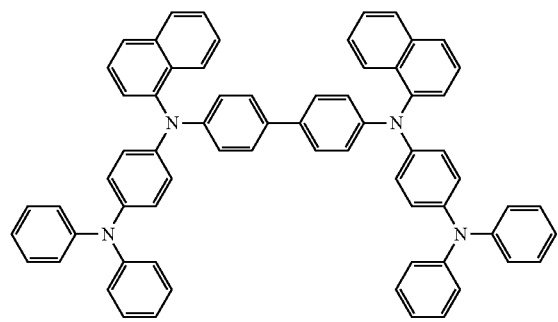

Compound II

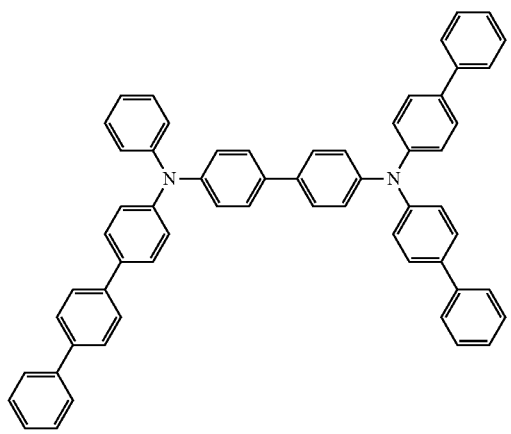

-continued

Compound D-1

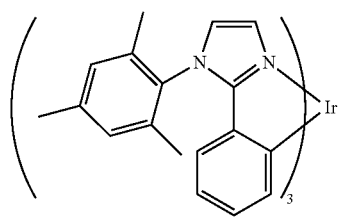

Compound III

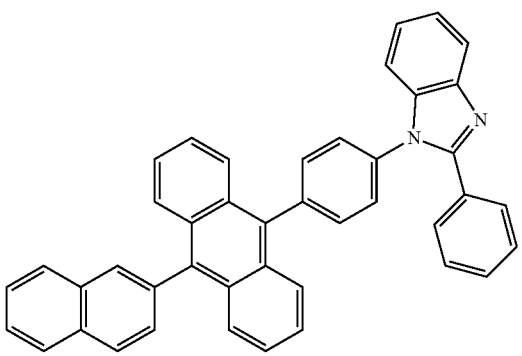

Compound H-1

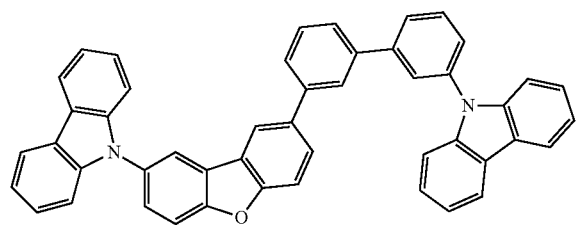

Compound H-2

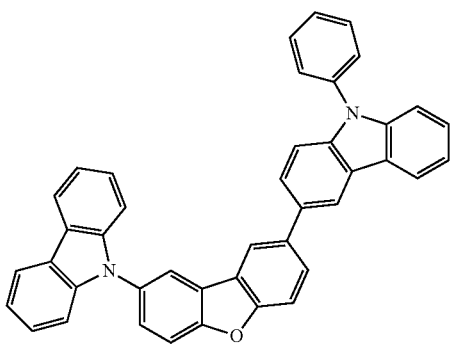

Compound H-3

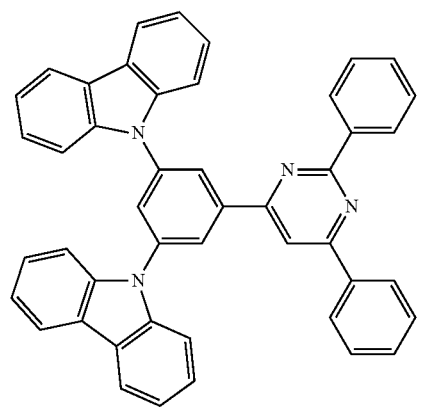

Compound H-4

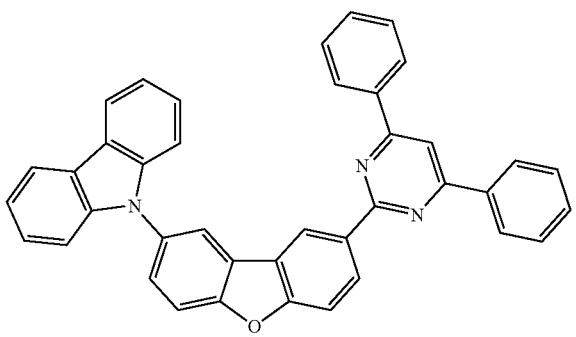

Compound H-5

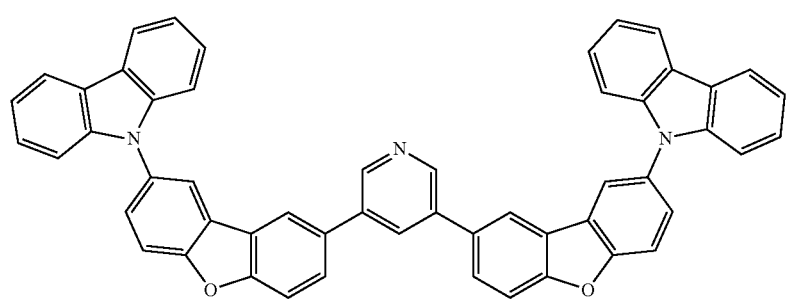

Evaluation of Emission Performance of Organic EL Device

The organic EL device was caused to emit light by DC drive to measure the luminance and the current density, and the voltage and the luminous efficiency (external quantum efficiency) at a current density of 1 mA/cm² were calculated. The luminance 70% decrease lifetime (i.e., the time required for the luminance to decrease to 70%) (initial luminance: 3000 cd/m²) was also calculated. The emission performance evaluation results are shown in Table 1.

Example 2

An organic EL device was fabricated and evaluated in the same method as in Example 1, except that the compound A was used to form the electron-transporting layer instead of the compound H-1. The results are shown in Table 1.

Example 3

An organic EL device was fabricated and evaluated in the same method as in Example 1, except that the compound B obtained in Synthesis Example 2 was used as the phosphorescent host material instead of the compound A. The results are shown in Table 1.

Example 4

An organic EL device was fabricated and evaluated in the same method as in Example 1, except that the compound B was used as the phosphorescent host material instead of the compound A, and the compound B was used to form the electron-transporting layer instead of the compound H-1. The results are shown in Table 1.

Example 5

An organic EL device was fabricated and evaluated in the same method as in Example 1, except that the compound H-1 was used as the phosphorescent host material instead of the compound A, and the compound A was used to form the electron-transporting layer instead of the compound H-1. The results are shown in Table 1.

Example 6

An organic EL device was fabricated and evaluated in the same method as in Example 1, except that the compound H-1 was used as the phosphorescent host material instead of the compound A, and the compound B was used to form the electron-transporting layer instead of the compound H-1. The results are shown in Table 1.

Example 7

An organic EL device was fabricated and evaluated in the same method as in Example 1, except that the compound H-1 was used as the phosphorescent host material instead of the compound A, and the compound D was used to form the electron-transporting layer instead of the compound H-1. The results are shown in Table 1.

Comparative Example 1

An organic EL device was fabricated and evaluated in the same method as in Example 1, except that a compound H-2 was used as the phosphorescent host material instead of the compound A. The results are shown in Table 1.

Comparative Example 2

An organic EL device was fabricated and evaluated in the same method as in Example 1, except that a compound H-3 was used as the phosphorescent host material instead of the compound A. However, a blue emission wavelength from the compound D-1 (phosphorescent emitting material) was not observed, and the comparison target voltage and external quantum efficiency could not be measured. It is conjectured that an exciplex with the dopant was formed in the organic EL device of Comparative Example 2.

Comparative Example 3

An organic EL device was fabricated and evaluated in the same method as in Example 1, except that a compound H-4 was used as the phosphorescent host material instead of the compound A. However, a blue emission wavelength from the compound D-1 (phosphorescent emitting material) was not observed, and the comparison target voltage and external quantum efficiency could not be measured. It is conjectured that an exciplex was formed in the organic EL device of Comparative Example 3.

Comparative Example 4

An organic EL device was fabricated and evaluated in the same method as in Example 1, except that a compound H-5 was used as the phosphorescent host material instead of the compound A. The results are shown in Table 1.

Comparative Example 5

An organic EL device was fabricated and evaluated in the same method as in Example 1, except that the compound H-1 was used as the phosphorescent host material instead of the compound A, and the compound H-4 was used to form the electron-transporting layer instead of the compound H-1. The results are shown in Table 1.

Comparative Example 6

An organic EL device was fabricated and evaluated in the same method as in Example 1, except that the compound H-1 was used as the phosphorescent host material instead of the compound A, and the compound H-5 was used to form the electron-transporting layer instead of the compound H-1. The results are shown in Table 1.

TABLE 1

| | Host material for emitting layer | Material for electron-transporting layer | Voltage (V) | External quantum efficiency (%) | Luminance 70% decrease lifetime (h) |
| --- | --- | --- | --- | --- | --- |
| Example 1 | Compound A | Compound H-1 | 6.0 | 16.0 | 240 |
| Example 2 | Compound A | Compound A | 5.8 | 14.9 | 200 |
| Example 3 | Compound B | Compound H-1 | 5.5 | 18.6 | 120 |
| Example 4 | Compound B | Compound B | 4.9 | 18.5 | 120 |
| Example 5 | Compound H-1 | Compound A | 5.2 | 16.1 | 206 |
| Example 6 | Compound H-1 | Compound B | 5.6 | 18.2 | 335 |

TABLE 1-continued

| | Host material for emitting layer | Material for electron-transporting layer | Voltage (V) | External quantum efficiency (%) | Luminance 70% decrease lifetime (h) |
|---|---|---|---|---|---|
| Example 7 | Compound H-1 | Compound D | 5.1 | 18.3 | 300 |
| Comparative Example 1 | Compound H-2 | Compound H-1 | 7.2 | 16.4 | 50 |
| Comparative Example 2 | Compound H-3 | Compound H-1 | — | — | — |
| Comparative Example 3 | Compound H-4 | Compound H-1 | — | — | — |
| Comparative Example 4 | Compound H-5 | Compound H-1 | 5.4 | 16.3 | 20 |
| Comparative Example 5 | Compound H-1 | Compound H-4 | 6.0 | 10.9 | 200 |
| Comparative Example 6 | Compound H-1 | Compound H-5 | 5.6 | 18.0 | 100 |

The organic EL devices of Examples 1 to 4 in which the compound according to the invention was used for the emitting layer exhibited a significant decrease in voltage and a significant increase in lifetime as compared with the organic EL device of Comparative Example 1 in which the compound H-2 that does not have an azine ring was used, since the carrier balance within the emitting layer was improved due to an improvement in capability to inject electrons into the emitting layer. The organic EL devices of Examples 1 to 4 exhibited a significant increase in lifetime as compared with the organic EL device of Comparative Example 4 in which the compound H-5 that has a small difference in the electron distribution of HOMO and LUMO due to its symmetrical shape, and shows a low carrier-injecting capability. Since an exciplex was formed in the organic EL device of Comparative Example 2 in which the compound H-3 was used, and the organic EL device of Comparative Example 3 in which the compound H-4 was used, it was found that the compounds H-3 and H-4 are host materials in which the substituent that substitutes the azine ring is not appropriate for blue phosphorescence.

The organic EL devices of Examples 5 to 7 in which the compound according to the invention was used for the electron-transporting layer, exhibited a decrease in voltage and an increase in lifetime due to an improvement in electron-injecting/transporting capability. Since the organic EL device of Comparative Example 5 utilized the compound H-4 that is considered to form an exciplex in Comparative Example 3, the triplet energy could not be confined at the interface, and the efficiency significantly decreased. Since the organic EL device of Comparative Example 6 utilized the compound H-5 that has a small difference in the electron distribution of HOMO and LUMO due to its symmetrical shape, and shows a low carrier-injecting capability, the carrier balance deteriorated, and the lifetime decreased.

It was thus confirmed that the compound according to the invention in which the spatial extent of the LUMO is increased by bonding an azine ring and a dibenzofuran ring, is useful for suppressing formation of an exciplex while maintaining an excellent electron-injecting/transporting capability to obtain the target blue phosphorescence.

The nitrogen-containing heteroaromatic compound according to the invention may be used as a material for an organic EL device.

The organic EL device according to the invention may be used as a planar emitting device (e.g., a flat panel display of a wall TV), a backlight of a copier, a printer, or a liquid crystal display, a light source of an instrument (meter), a signboard, a marker lamp (light), and the like.

Although only some exemplary embodiments and/or examples of this invention have been described in detail above, those skilled in the art will readily appreciate that many modifications are possible in the exemplary embodiments and/or examples without materially departing from the novel teachings and advantages of this invention. Accordingly, all such modifications are intended to be included within the scope of this invention.

The documents described in the specification and the specification of the Japanese application(s) on the basis of which the present application claims Paris convention priority are incorporated herein by reference in its entirety.

What is claimed is:
1. A nitrogen-containing heteroaromatic compound represented by formula (A),

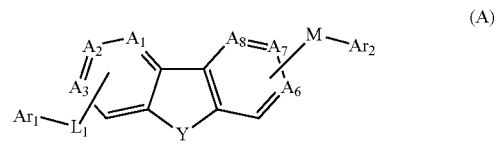

wherein:
each of $A_1$ to $A_3$ and $A_6$ to $A_8$ is independently $CR^1$;
each $R^1$ is independently a hydrogen atom, a substituted or unsubstituted alkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted cycloalkoxy group having 3 to 20 ring carbon atoms, a substituted or unsubstituted aromatic hydrocarbon group having 6 to 18 ring carbon atoms, a substituted or unsubstituted aryloxy group having 6 to 18 ring carbon atoms, a substituted or unsubstituted pyrrolyl group, a substituted or unsubstituted pyrazinyl group, a substituted or unsubstituted pyridinyl group, a substituted or unsubstituted pyrimidinyl group, a substituted or unsubstituted triazinyl group, a substituted or unsubstituted indolyl group, a substituted or unsubstituted isoindolyl group, a substituted or unsubstituted imidazolyl group, a substituted or unsubstituted furyl group, a substituted or unsubstituted benzofuranyl group, an substituted or unsubstituted isobenzofuranyl group, a substituted or unsubstituted dibenzofuranyl group, a substituted or unsubstituted quinolyl group, a substituted or unsubstituted isoquinolyl group, a substituted or unsubstituted quinoxalinyl group, a substituted or unsubstituted carbazolyl group, a substituted or unsubstituted phenanthridinyl group, a substituted or unsubstituted acridinyl group, a substituted or unsubstituted phenanthrolnyl group, a substituted or unsubstituted phenazinyl group, a substituted or unsubstituted phenothiazinyl group, a substituted or unsubstituted phenoxadinyi group, a substituted or unsubstituted oxazolyl group, a substituted or unsubstituted oxadiazolyl group, a substituted or unsubstituted furazanyl group, a substituted or unsubstituted thienyl group, a substituted or unsubstituted benzothiophenyl group, a substituted or unsubstituted dihydroacridinyl group, a substituted or unsubstituted azacarbazolyl group, a substituted or unsubstituted quinazolinyl group, a substituted or unsubstituted amino group, a substituted or unsubstituted silyl group, a fluorine atom, a substituted or unsubstituted fluoroalkyl group, or a cyan group;

Y is an oxygen atom;

$Ar_1$ is a hydrogen atom, a substituted or unsubstituted aromatic hydrocarbon group having 6 to 18 ring carbon atoms, a substituted or unsubstituted pyrrolyl group, a substituted or unsubstituted pyrazinyl group, a substituted or unsubstituted pyridinyl group, a substituted or unsubstituted pyrimidinyl group, a substituted or unsubstituted triazinyl group, a substituted or unsubstituted indolyl group, a substituted or unsubstituted isoindolyl group, a substituted or unsubstituted imidazolyl group, a substituted or unsubstituted furyl group, a substituted or unsubstituted benzofuranyl group, an substituted or unsubstituted isobenzofuranyl group, a substituted or unsubstituted dibenzofuranyl group, a substituted or unsubstituted quinolyl group, a substituted or unsubstituted isoquinolyl group, a substituted or unsubstituted quinoxalinyl group, a substituted or unsubstituted carbazolyl group, a substituted or unsubstituted phenanthridinyl group, a substituted or unsubstituted acridinyl group, a substituted or unsubstituted phenanthrolinyl group, a substituted or unsubstituted phenazinyl group, a substituted or unsubstituted phenothiazinyl group, a substituted or unsubstituted phenoxadinyl group, a substituted or unsubstituted oxazolyl group, a substituted or unsubstituted oxadiazolyl group, a substituted or unsubstituted furazanyl group, a substituted or unsubstituted thienyl group, a substituted or unsubstituted benzothiophenyl group, a substituted or unsubstituted dihydroacridinyl group, a substituted or unsubstituted azacarbazolyl group, or a substituted or unsubstituted quinazolinyl group;

$L_1$ is a single bond, a substituted or unsubstituted aromatic hydrocarbon group having 6 to 18 ring carbon atoms, or a divalent group derived from a substituted or unsubstituted pyrrolyl group, a substituted or unsubstituted pyrazinyl group, a substituted or unsubstituted pyridinyl group, a substituted or unsubstituted pyrimidinyl group, a substituted or unsubstituted triazinyl group, a substituted or unsubstituted indolyl group, a substituted or unsubstituted isoindolyl group, a substituted or unsubstituted imidazolyl group, a substituted or unsubstituted furyl group, a substituted or unsubstituted benzofuranyl group, an substituted or unsubstituted isobenzofuranyl group, a substituted or unsubstituted dibenzofuranyl group, a substituted or unsubstituted quinolyl group, a substituted or unsubstituted isoquinolyl group, a substituted or unsubstituted quinoxalinyl group, a substituted or unsubstituted carbazolyl group, a substituted or unsubstituted phenanthridinyl group, a substituted or unsubstituted acridinyl group, a substituted or unsubstituted phenanthrolinyl group, a substituted or unsubstituted phenazinyl group, a substituted or unsubstituted phenothiazinyl group, a substituted or unsubstituted phenoxadinyl group, a substituted or unsubstituted oxazolyl group, a substituted or unsubstituted oxadiazolyl group, a substituted or unsubstituted furazanyl group, a substituted or unsubstituted thienyl group, a substituted or unsubstituted benzothiophenyl group, a substituted or unsubstituted dihydroacridinyl group, a substituted or unsubstituted azacarbazolyl group, or a substituted or unsubstituted quinazolinyl group, and $L_1$ is bonded to one of $A_1$ to $A_3$;

M is a substituted or unsubstituted 6-membered nitrogen-containing heteroaromatic group, and M is bonded to one of $A_6$ to $A_8$;

$Ar_2$ is a substituted or unsubstituted monocyclic heteroaromatic group having 5 or 6 ring atoms or a nitrogen-containing polycyclic group selected from the group consisting of nitrogen-containing polycyclic groups represented by formulas (1) to (5),

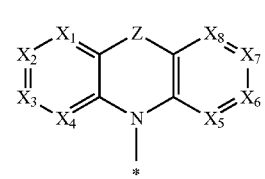

(1)

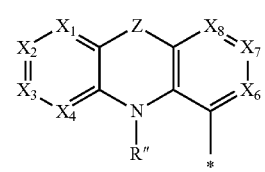

(2)

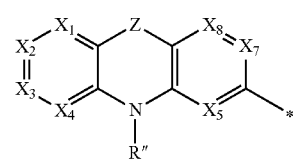

(3)

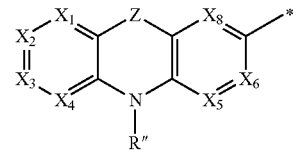

(4)

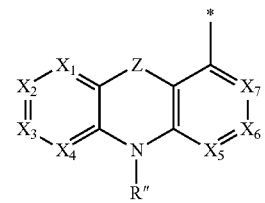

(5)

wherein:
each of $X_1$ to $X_8$ is independently CR' or a nitrogen atom;
Z is a single bond, an oxygen atom, a sulfur atom, =S(=O), =S(=O)$_2$, =SiR$^2$R$^3$, =CR$^4$R$^5$, or =NR$^6$;
each R' is independently a hydrogen atom, a substituted or unsubstituted alkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted cycloalkoxy group having 3 to 20 ring carbon atoms, a substituted or unsubstituted aryloxy group having 6 to 18 ring carbon atoms, a substituted or unsubstituted pyrrolyl group, a substituted or unsubstituted pyrazinyl group, a substituted or unsubstituted pyridinyl group, a substituted or unsubstituted pyrimidinyl group, a substituted or unsubstituted triazinyl group, a substituted or unsubstituted indolyl group, a substituted or unsubstituted isoindolyl group, a substituted or unsubstituted imidazolyl group, a substituted or unsubstituted furyl group, a substituted or unsubstituted benzofuranyl group, an substituted or unsubstituted isobenzofuranyl group, a substituted or unsubstituted dibenzofuranyl group, a substituted or unsubstituted quinolyl group, a substituted or unsubstituted isoquinolyl group, a substituted or unsubstituted quinoxalinyl group, a substituted or unsubstituted carbazolyl group, a substituted or unsubstituted phenanthridinyl group, a substituted or unsubstituted acridinyl group, a substituted or unsubstituted phenanthrolinyl group, a substituted or unsubstituted phenazinyl group, a substituted or unsubstituted phenothiazinyl group, a substituted or unsubstituted phenoxadinyl group, a substituted or unsubstituted oxazolyl group, a substituted or unsubstituted oxadiazolyl group, a substituted or unsubstituted furazanyl group, a substituted or unsubstituted thienyl group, a substituted or unsubstituted benzothiophenyl group, a substituted or unsubstituted dihydroacridinyl group, a substituted or unsubstituted azacarbazolyl group, a substituted or unsubstituted quinazolinyl group, a substituted or unsubstituted amino group, a substituted or unsubstituted silyl group, a fluorine atom, a substituted or unsubstituted fluoroalkyl group, or a cyano group;

each of R″ and $R^2$ to $R^6$ is independently an atom or a group among the atoms and the groups defined by $R^1$; and

* is a position bonded to M; and when $R^1$, $Ar_1$, $L_1$, M, $Ar_2$, R′, R″, $R^2$, $R^3R^4$, $R^5$, or $R^6$ as a substituent, the substituent is an alkyl group, an amino group, a silyl group, an aromatic hydrocarbon group, a cycloalkyl group, an alkoxy group, a fluoroalkyl group, a halogen atom, a hydroxyl group, a nitro group, a cyano group, a carboxyl group, an aryloxy group, a diarylphosphino group, a diarylphosphine oxide group, or a diarylphosphinoaryl group.

2. A material for an organic electroluminescence device comprising the nitrogen-containing heteroaromatic compound according to claim 1.

3. An organic electroluminescence device, comprising:
a cathode:
an anode; and
one or more organic thin film layers provided between the cathode and the anode;
wherein:
at least one of the organic thin film layers is an emitting layer;
at least one of the organic thin film layers comprises the material for an organic electroluminescence device according to claim 2.

4. The organic electroluminescence device according to claim 3, wherein the emitting layer comprises the material for an organic electroluminescence device as a host material.

5. The organic electroluminescence device according to claim 3, wherein the emitting layer comprises a phosphorescent emitting material, and the phosphorescent emitting material is an orthometalated complex of a metal atom selected from iridium (Ir), osmium (Os), and platinum (Pt).

6. The organic electroluminescence device according to claim 3, comprising an organic thin film layer between the cathode and the emitting layer, wherein the organic thin film layer comprises the material for an organic electroluminescence device.

7. The nitrogen-containing heteroaromatic compound according claim 1, wherein $Ar_2$ is a substituted or unsubstituted monocyclic heteroaromatic group having 5 or 6 ring atoms or a nitrogen-containing polycyclic group selected from the group consisting of nitrogen-containing polycyclic groups represented by formulas (1a) to (5a)

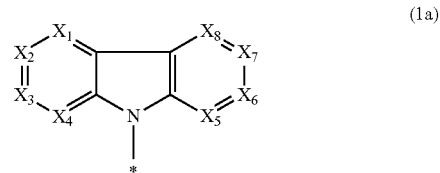

(1a)

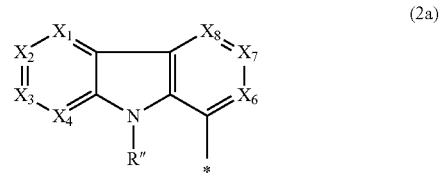

(2a)

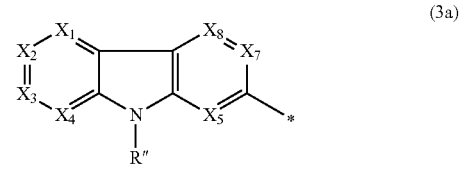

(3a)

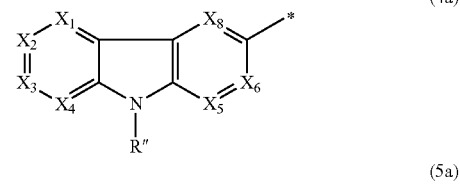

(4a)

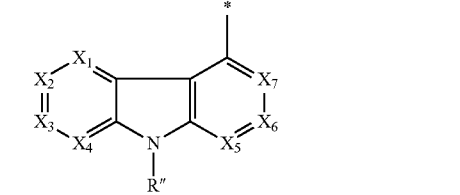

(5a)

wherein $X_1$ to $X_8$, R″, and * are as defined for the nitrogen-containing polycyclic groups represented by formulas (1)or (5).

8. The nitrogen-containing heteroaromatic compound according to claim 1 wherein $L_1$ is a single bond.

9. The nitrogen-containing heteroaromatic compound according to claim 1, wherein $Ar_1$ is a substituted or unsubstituted carbazolyl group or a substituted or unsubstituted azacarbazolyl group.

10. The nitrogen-containing heteroaromatic compound according to claim 1, wherein $Ar_2$ is a nitrogen-containing polycyclic group represented by the formula (1a).

11. The nitrogen-containing heteroaromatic compound according to claim 10, wherein Ar₁ is a substituted or unsubstituted carbazolyl group that is bonded to L₁ at position 9.

12. A nitrogen-containing heteroaromatic compound represented by formula (A),

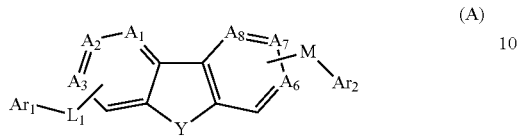

wherein:
  each of $A_1$ to $A_3$ and $A_6$ to $A_8$ is independently $CR^1$;
  each $R^1$ is independently a hydrogen atom, a substituted or unsubstituted alkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted cycloalkoxy group having 3 to 20 ring carbon atoms, a substituted or unsubstituted aromatic hydrocarbon group having 6 to 18 ring carbon atoms, a substituted or unsubstituted aryloxy group having 6 to 18 ring carbon atoms, a substituted or unsubstituted pyrrolyl group, a substituted or unsubstituted pyrazinyl group, a substituted or unsubstituted pyridinyl group, a substituted or unsubstituted pyrimidinyl group, a substituted or unsubstituted triazinyl group, a substituted or unsubstituted indolyl group, a substituted or unsubstituted isoindolyl group, a substituted or unsubstituted imidazolyl group, a substituted or unsubstituted furyl group, a substituted or unsubstituted benzofuranyl group, an substituted or unsubstituted isobenzofuranyl group, a substituted or unsubstituted dibenzofuranyl group, a substituted or unsubstituted quinolyl group, a substituted or unsubstituted isoquinolyl group, a substituted or unsubstituted quinoxalinyl group, a substituted or unsubstituted carbazolyl group, a substituted or unsubstituted phenanthridinyl group, a substituted or unsubstituted acridinyl group, a substituted or unsubstituted phenanthrolinyl group, a substituted or unsubstituted phenazinyl group, a substituted or unsubstituted phenothiazinyl group, a substituted or unsubstituted phenoxadinyl group, a substituted or unsubstituted oxazolyl group, a substituted or unsubstituted oxadiazolyl group, a substituted or unsubstituted furazanyl group, a substituted or unsubstituted thienyl group, a substituted or unsubstituted benzothiophenyl group, a substituted or unsubstituted dihydroacridinyl group, a substituted or unsubstituted azacarbazolyl group, a substituted or unsubstituted quinazolinyl group, a substituted or unsubstituted amino group, a substituted or unsubstituted silyl group, a fluorine atom, a substituted or unsubstituted fluoroalkyl group, or a cyano group;
  Y is an oxygen atom;
  Ar₁ is a hydrogen atom, a substituted or unsubstituted aromatic hydrocarbon group having 6 to 18carbon atoms, a substituted or unsubstituted pyrrolyl group, a substituted or unsubstituted pyrazinyl group, a substituted or unsubstituted pyridinyl group, a substituted or unsubstituted pyrimidinyl group, a substituted or unsubstituted triazinyl group, a substituted or unsubstituted indolyl group, a substituted or unsubstituted isoindolyl group, a substituted or unsubstituted imidazolyl group, a substituted or unsubstituted furyl group, a substituted or unsubstituted benzofuranyl group, substituted or unsubstituted isobenzofuranyl group, a substituted or unsubstituted dibenzofuranyl group, a substituted or unsubstituted quinolyl group, a substituted or unsubstituted isoquinolyl group, a substituted or unsubstituted quinoxalinyl group, a substituted or unsubstituted carbazolyl group, a substituted or unsubstituted phenanthridinyl group, a substituted or unsubstituted acridinyl group, a substituted or unsubstituted phenanthrolinyl group, a substituted or unsubstituted phenazinyl group, a substituted or unsubstituted phenothiazinyl group, a substituted or unsubstituted phenoxadinyl group, a substituted or unsubstituted oxazolyl group, a substituted or unsubstituted oxadiazolyl group, a substituted or unsubstituted furazanyl group, a substituted or unsubstituted thienyl group, a substituted or unsubstituted benzothiophenyl group, a substituted or unsubstituted dihydroacridinyl group, a substituted or unsubstituted azacarbazolyl group, or a substituted or unsubstituted quinazolinyl group;
  L₁ is a single bond, a substituted or unsubstituted aromatic hydrocarbon group having 6 to 18 ring carbon atoms, or a divalent group derived from a substituted or unsubstituted pyrrolyl group, a substituted or unsubstituted pyrazinyl group, a substituted or unsubstituted pyridinyl group, a substituted or unsubstituted pyrimidinyl group, a substituted or unsubstituted triazinyl group, a substituted or unsubstituted indolyl group, a substituted or unsubstituted isoindolyl group, a substituted or unsubstituted imidazolyl group, a substituted or unsubstituted furyl group, a substituted or unsubstituted benzofuranyl group, an substituted or unsubstituted isobenzofuranyl group, a substituted or unsubstituted dibenzofuranyl group, a substituted or unsubstituted quinolyl group, a substituted or unsubstituted isoquinolyl group, a substituted or unsubstituted quinoxalinyl group, a substituted or unsubstituted carbazotyl group, a substituted or unsubstituted phenanthridinyl group, a substituted or unsubstituted acridinyl group, a substituted or unsubstituted phenanthrolinyl group, a substituted or unsubstituted phenazinyl group, a substituted or unsubstituted phenothiazinyl group, a substituted or unsubstituted phenoxadinyl group, a substituted or unsubstituted oxazolyl group, a substituted or unsubstituted oxadiazolyl group, a substituted or unsubstituted furazanyl group, a substituted or unsubstituted thienyl group, a substituted or unsubstituted benzothiophenyl group, a substituted or unsubstituted dihydroacridinyl group, a substituted or unsubstituted azacarbazolyl group, or a substituted or unsubstituted quinazolinyl group, and L₁ is bonded to one of $A_1$ to $A_3$;
  M is a substituted or unsubstituted monocyclic nitrogen-containing heteroaromatic group, and M s bonded to one of $A_6$ to $A_8$;
  Ar₂ is a substituted or unsubstituted monocyclic heteroaromatic group having 5 or 6 ring atoms or a nitrogen-containing polycyclic group selected from the group consisting of nitrogen-containing polycyclic groups represented by formulas (1a) to (5a),

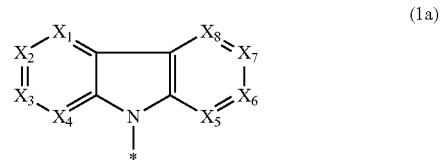

(1a)

-continued

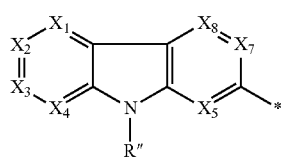 (2a)

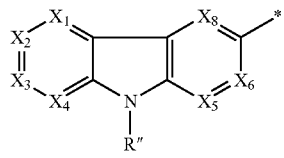 (3a)

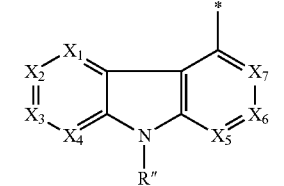 (4a)

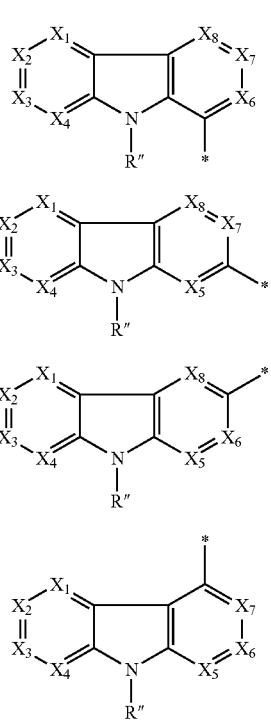 (5a)

wherein:
each of $X_1$ to $X_8$ is independently CR' or a nitrogen atom;
Z is a single bond, an oxygen atom, a sulfur atom, $=S(=O)$, $=S(=O)_2$, $=SiR^2R^3$, $=CR^4R^5$, or $=NR^6$;
each R' is independently a hydrogen atom, a substituted or unsubstituted alkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted cycloalkoxy group having 3 to 20 ring carbon atoms, a substituted or unsubstituted aryloxy group having 6 to 18 ring carbon atoms, a substituted or unsubstituted pyrrolyl group, a substituted or unsubstituted pyrazinyl group, a substituted or unsubstituted pyridinyl group, a substituted or unsubstituted pyrimidinyl group, a substituted or unsubstituted triazinyl group, a substituted or unsubstituted indolyl group, a substituted or unsubstituted isoindolyl group, a substituted or unsubstituted imidazolyl group, a substituted or unsubstituted furyl group, a substituted or unsubstituted benzofuranyl group, an substituted or unsubstituted isobenzofuranyl group, a substituted or unsubstituted dibenzofuranyl group, a substituted or unsubstitutedquinolyl group, a substituted or unsubstituted isoquinolyl group, a substituted or unsubstituted quinoxalinyl group, a substituted or unsubstituted carbazolyl group, a substituted or unsubstituted phenanthridinyl group, a substituted or unsubstituted acridinyl group, a substituted or unsubstituted phenanthrolinyl group, a substituted or unsubstituted phenazinyl group, a substituted or unsubstituted phenothiazinyl group, a substituted or unsubstituted phenoxadinyl group, a substituted or unsubstituted oxazolyl group, a substituted or unsubstituted oxadiazolyl group, a substituted or unsubstituted furazanyl group, a substituted or unsubstituted thienyl group, a substituted or unsubstituted benzothiophenyl group, a substituted or unsubstituted dihydroacridinyl group, a substituted or unsubstituted azacarbazolyl group, a substituted or unsubstituted quinazolinyl group, a substituted or unsubstituted amino group, a substituted or unsubstituted silyl group, a fluorine atom, a substituted or unsubstituted fluoroalkyl group, or a cyano group;
each of R" and $R^2$ to $R^6$ is independently an atom or a group among the atoms and the groups defined by $R^1$; and
* is a position bonded to M; and
when $R^1$, $Ar_1$, $L_1$, M, $Ar_2$, R', R" $R^2$, $R^3$, $R^4$, $R^5$, or $R^6$ has a substituent, the substituent is an alkyl group, an amino group, a silyl group, an aromatic hydrocarbon group, a cycloalkyl group, an alkoxy group, a fluoroalkyl group, a halogen atom, a hydroxyl group, a nitro group, a cyano group, a carboxyl group, an aryloxy group, a diarylphosphino group, a diarylphosphine oxide group, or a diarylphosphinoaryl group.

13. The nitrogen-containing heteroaromatic compound according to claim 12, wherein $Ar_2$ is a nitrogen-containing polycyclic group selected from the group consisting of nitrogen-containing polycyclic groups represented by formulas (1) to (5).

14. The nitrogen-containing heteroaromatic compound according to claim 12, wherein $Ar_2$ is a nitrogen-containing polycyclic group selected from the group consisting of nitrogen-containing polycyclic groups represented by formulas (1a) to (5a).

15. The nitrogen-containing heteroaromatic compound according to claim 12, wherein $Ar_2$ is a nitrogen-containing polycyclic group represented by formula (1).

16. The nitrogen-containing heteroaromatic compound according to claim 12, wherein $Ar_2$ is a nitrogen-containing polycyclic group represented by formula (1a).

17. A nitrogen-containing heteroaromatic compound represented by formula (A),

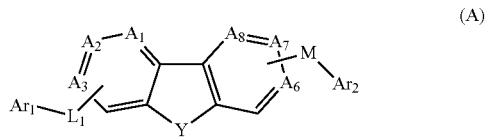 (A)

wherein:
each of $A_1$ to $A_3$ and $A_6$ to $A_8$ is independently $CR^1$;
each $R^1$ is independently a hydrogen atom, a substituted or unsubstituted alkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted cycloalkoxy group having 3 to 20 ring carbon atoms, a substituted or unsubstituted aromatic hydrocarbon group having 6 to 18 ring carbon atoms, a substituted or unsubstituted aryloxy group having 6 to 18 ring carbon atoms, a substituted or unsubstituted pyrrolyl group, a substituted or unsubstituted pyrazinyl group, a substituted or unsubstituted pyridinyl group, a substituted or unsubstituted pyrimidinyl group, a substituted or unsubstituted triazinyl group, a substituted or unsubstituted indolyl group, a substituted or unsubstituted isoindolyl group, a substituted or unsubstituted imidazolyl group, a substituted or unsubstituted furyl group, a substituted or unsubstituted benzofuranyl group, an substituted or unsubstituted isobenzofuranyl group, a substituted or unsubstituted dibenzofuranyl group, a substituted or unsubstituted quinolyl group, a substituted or unsubstituted isoquinolyl group, a substituted or unsubstituted quinoxalinyl group, a substituted or unsubstituted carbazolyl group, a substituted or unsubstituted phenanthridinyl group, a substituted or unsubstituted acridinyl group, a substituted or unsubstituted phenanthrolinyl group, a substituted or unsubstituted phenazinyl group, a substituted or unsubstituted phenothiazinyl group, a substituted or unsubstituted phenoxadinyl group, a substituted or unsubstituted oxazolyl group, a substituted or unsubstituted oxadiazolyl group, a substituted or unsubstituted furazanyl group, a substituted or unsubstituted thienyl group, a substituted or unsubstituted benzothiophenyl group, a substituted or unsubstituted dihydroacridinyl group, a substituted or unsubstituted azacarbazolyl group, a substituted or unsubstituted quinazolinyl group, a substituted or unsubstituted amino group, a substituted or unsubstituted silyl group, a fluorine atom a substituted or unsubstituted fluoroalkyl group, or a cyano group;

Y is an oxygen atom;

$Ar_1$ is a hydrogen atom, a substituted or unsubstituted aromatic hydrocarbon group having 6 to 18 ring carbon atoms, a substituted or unsubstituted pyrrolyl group, a substituted or unsubstituted pyrazinyl group, a substituted or unsubstituted pyridinyl group, a substituted or unsubstituted pyrimidinyl group, a substituted or unsubstituted triazinyl group, a substituted or unsubstituted indolyl group, a substituted or unsubstituted isoindolyl group, a substituted or unsubstituted imidazolyl group, a substituted or unsubstituted furyl group, a substituted or unsubstituted benzofuranyl group, an substituted or unsubstituted isobenzofuranyl group, a substituted or unsubstituted dibenzofuranyl group, a substituted or unsubstituted quinolyl group, a substituted or unsubstituted isoquinolyl group, a substituted or unsubstituted quinoxalinyl group, a substituted or unsubstituted carbazolyl group, a substituted or unsubstituted phenanthridinyl group, a substituted or unsubstituted acridinyl group, a substituted or unsubstituted phenanthrolinyl group, a substituted or unsubstituted phenazinyl group, a substituted or unsubstituted phenothiazinyl group, a substituted or unsubstituted phenoxadinyl group, a substituted or unsubstituted oxazolyl group, a substituted or unsubstituted oxadiazolyl group, a substituted or unsubstituted furazanyl group, a substituted or unsubstituted thienyl group, a substituted or unsubstituted benzothiophenyl group, a substituted or unsubstituted dihydroacridinyl group, a substituted or unsubstituted azacarbazolyl group, or a substituted or unsubstituted quinazolinyl group;

$L_1$ is a single bond, and $L_1$ is bonded to one of $A_1$ to $A_3$;

M is a substituted or unsubstituted monocyclic nitrogen-containing heteroaromatic group, and M s bonded to one of $A_6$ to $A_8$;

$Ar_2$ is a substituted or unsubstituted monocyclic heteroaromatic group having 5 or 6 ring atoms or a nitrogen-containing polycyclic group selected from the group consisting of nitrogen-containing polycyclic groups represented by formulas (1) to (5),

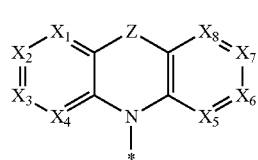
(1)

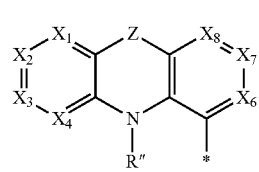
(2)

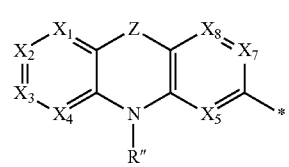
(3)

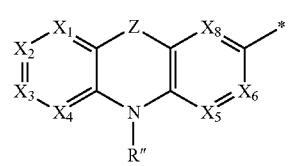
(4)

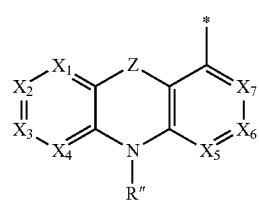
(5)

wherein:
each of $X_1$ to $X_8$ is independently CR' or a nitrogen atom;
Z is a single bond, an oxygen atom, a sulfur atom, $=S(=O)$, $=S(=O)_2$, $=SiR^2R^3$, $=CR^4R^5$, or $=NR^6$;
each R' is independently a hydrogen atom, a substituted or unsubstituted alkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted cycloalkoxy group having 3 to 20 ring carbon atoms, a substituted or unsubstituted aryloxy group having 6 to 18 ring carbon atoms, a substituted or unsubstituted pyrrolyl group, a substituted or unsubstituted pyrazinyl group, a substituted or unsubstituted pyridinyl group, a substituted or unsubstituted pyrimidinyl group, a substituted or unsubstituted triazinyl group, a substituted or unsubstituted indolyl group, a substituted or unsubstituted isoindolyl group, a substituted or unsubstituted imidazolyl group, a substituted or unsubstituted furyl group, a substituted or unsubstituted benzofuranyl group, an substituted or unsubstituted isobenzofuranyl group, a substituted or unsubstituted dibenzofuranyl group, a substituted or unsubstituted quinolyl group, a substituted or unsubstituted isoquinolyl group, a substituted or unsubstituted quinoxalinyl group, a substituted or unsubstituted carbazolyl group, a substituted or unsubstituted phenanthridinyl group, a substituted or unsubstituted acridinyl group, a substituted or unsubstituted phenanthrolinyl group, a substituted or unsubstituted phenazinyl group, a substituted or unsubstituted phenothiazinyl group, a substituted or unsubstituted phenoxadinyl group, a substituted or unsubstituted oxazolyl group, a substituted or unsubstituted oxadiazolyl group, a substituted or unsubstituted furazanyl group, a substituted or unsubstituted thienyl group, a substituted or unsubstituted dihydroacridinyl group, a substituted or unsubstituted azacarbazolyl group, a substituted or unsubstituted quinazolinyl group, a substituted or unsubstituted amino group, a substituted or unsubstituted silyl group, a fluorine atom, a substituted or unsubstituted fluoroalkyl group, or a cyano group;

each of R″ and $R^2$ to $R^6$ is independently an atom or a group among the atoms and the groups defined by $R^1$; and

* is a position bonded to M; and when $R^1$, $Ar_1$, $L_1$, M, $Ar_2$, R′, R″, $R^2$, $R^3$, $R^4$, $R^5$, or $R^6$ has a substituent, the substituent is an alkyl group, an amino group, a silyl group, an aromatic hydrocarbon group, a cycloalkyl group, an alkoxy group, a fluoroalkyl group, a halogen atom, a hydroxyl group, a nitro group, a cyano group, a carboxyl group, an aryloxy group, a diarylphosphino group, a diarylphosphine oxide group, or a diarylphosphinoaryl group.

18. A nitrogen-containing heteroaromatic compound represented by formula (A),

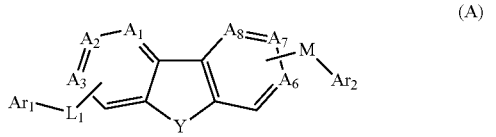

(A)

wherein:
each of $A_1$ to $A_3$ and $A_6$ to $A_8$ is independently $CR^1$;

each $R^1$ is independently a hydrogen atom, a substituted or unsubstituted alkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted cycloalkoxy group having 3 to 20 ring carbon atoms, a substituted or unsubstituted aromatic hydrocarbon group having 6 to 18 ring carbon atoms, a substituted or unsubstituted aryloxy group having 6 to 18 ring carbon atoms, a substituted or unsubstituted pyrrolyl group, a substituted or unsubstituted pyrazinyl group, a substituted or unsubstituted pyridinyl group, a substituted or unsubstituted pyrimidinyl group, a substituted or unsubstituted triazinyl group, a substituted or unsubstituted indolyl group, a substituted or unsubstituted isoindolyl group, a substituted or unsubstituted imidazolyl group, a substituted or unsubstituted furyl group, a substituted or unsubstituted benzofuranyl group, an substituted or unsubstituted isobenzofuranyl group, a substituted or unsubstituted dibenzofuranyl group, a substituted or unsubstituted quinolyl group, a substituted or unsubstituted isoquinolyl group, a substituted or unsubstituted quinoxalinyl group, a substituted or unsubstituted carbazolyl group, a substituted or unsubstituted phenanthridinyl group, a substituted or unsubstituted acridinyl group, a substituted or unsubstituted phenanthrolinyl group, a substituted or unsubstituted phenazinyl group, a substituted or unsubstituted phenothiazinyl group, a substituted or unsubstituted phenoxadinyl group, a substituted or unsubstituted oxazolyl group, a substituted or unsubstituted oxadiazolyl group, a substituted or unsubstituted furazanyl group, a substituted or unsubstituted thienyl group, a substituted or unsubstituted benzothiophenyl group, a substituted or unsubstituted dihydroacridinyl group, a substituted or unsubstituted azacarbazolyl group, a substituted or unsubstituted quinazolinyl group, a substituted or unsubstituted amino group, a substituted or unsubstituted silyl group, a fluorine atom, a substituted or unsubstituted fluoroalkyl group, or a cyano group;

Y is an oxygen atom;

$Ar_1$ is a substituted or unsubstituted carbazolyl group or a substituted or unsubstituted azacarbazolyl group;

$L_1$ is a single bond, a substituted or unsubstituted aromatic hydrocarbon group having 6 to 18 ring carbon atoms, or a divalent group derived from a substituted or unsubstituted pyrrolyl group, a substituted or unsubstituted pyrazinyl group, a substituted or unsubstituted pyridinyl group, a substituted or unsubstituted pyrimidinyl group, a substituted or unsubstituted triazinyl group, a substituted or unsubstituted indolyl group, a substituted or unsubstituted isoindolyl group, a substituted or unsubstituted imidazolyl group, a substituted or unsubstituted furyl group, a substituted or unsubstituted benzofuranyl group, an substituted or unsubstituted isobenzofuranyl group, a substituted or unsubstituted dibenzofuranyl group, a substituted or unsubstituted quinolyl group, a substituted or unsubstituted isoquinolyl group, a substituted or unsubstituted quinoxalinyl group, a substituted or unsubstituted carbazolyl group a substituted or unsubstituted phenanthridinyl group, a substituted or unsubstituted acridinyl group, a substituted or unsubstituted phenanthrolinyl group, a substituted or unsubstituted phenazinyl group, a substituted or unsubstituted phenothiazinyl group, a substituted or unsubstituted phenoxadinyl group, a substituted or unsubstituted oxazolyl group, a substituted or unsubstituted oxadiazolyl group, a substituted or unsubstituted furazanyl group, a substituted or unsubstituted thienyl group, a substituted or unsubstituted benzothiophenyl group, a substituted or unsubstituted dihydroacridinyl group, a substituted or unsubstituted azacarbazolyl group, or a substituted or unsubstituted quinazolinyl group, and $L_1$ is bonded to one of $A_1$ to $A_3$;

M is a substituted or unsubstituted monocyclic nitrogen-containing heteroaromatic group, and M s bonded to one of $A_6$ to $A_8$;

$Ar_2$ is a substituted or unsubstituted monocyclic heteroaromatic group having 5 or 6 ring atoms or a nitrogen-containing polycyclic group selected from the group consisting of nitrogen-containing polycyclic groups represented by formulas (1) to (5),

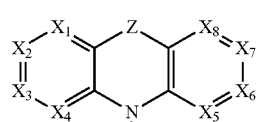

(1)

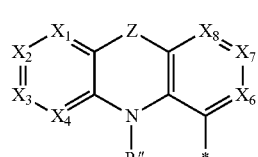

(2)

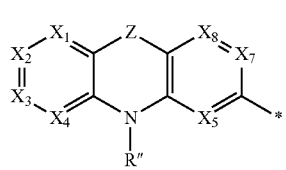

(3)

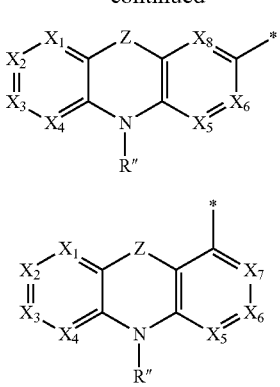

wherein:
each of $X_1$ to $X_8$ is independently CR' or a nitrogen atom;
Z is a single bond, an oxygen atom, a sulfur atom, =S(=O), =S(=O)$_2$, =SiR$^2$R$^3$, =CR$^4$R$^5$, or =NR$^6$;

each R' is independently a hydrogen atom, a substituted or unsubstituted alkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted cycloalkoxy group having 3 to 20 ring carbon atoms, a substituted or unsubstituted aryloxy group having 6 to 18 ring carbon atoms, a substituted or unsubstituted pyrrolyl group, a substituted or unsubstituted pyrazinyl group, a substituted or unsubstituted pyridinyl group, a substituted or unsubstituted pyrimidinyl group, a substituted or unsubstituted triazinyl group, a substituted or unsubstituted indolyl group, a substituted or unsubstituted isoindolyl group, a substituted or unsubstituted imidazolyl group, a substituted or unsubstituted furyl group, a substituted or unsubstituted benzofuranyl group, an substituted or unsubstituted isobenzofuranyl group, a substituted or unsubstituted dibenzofuranyl group, a substituted or unsubstituted quinolyl group, a substituted or unsubstituted isoquinolyl group, a substituted or unsubstituted quinoxalinyl group, a substituted or unsubstituted carbazolyl group, a substituted or unsubstituted phenanthridinyl group, a substituted or unsubstituted acridinyl group, a substituted or unsubstituted phenanthrolinyl group, a substituted or unsubstituted phenazinyl group, a substituted or unsubstituted phenothiazinyl group, a substituted or unsubstituted phenoxadinyl group, a substituted or unsubstituted oxazolyl group, a substituted or unsubstituted oxadiazolyl group, a substituted or unsubstituted furazanyl group, a substituted or unsubstituted thienyl group, a substituted or unsubstituted benzothiophenyl group, a substituted or unsubstituted dihydroacridinyl group, a substituted or unsubstituted azacarbazolyl group, a substituted or unsubstituted quinazolinyl group, a substituted or unsubstituted amino group, a substituted or unsubstituted silyl group, a fluorine atom, a substituted or unsubstituted fluoroalkyl group, or a cyano group;

each of R" and R$^2$ to R$^6$ is independently an atom or a group among the atoms and the groups defined by R$^1$; and

* is a position bonded to M; and when R$^1$, Ar$_1$, L$_1$, M, Ar$_2$, R', R", R$^2$, R$^3$, R$^4$, R$^5$, or R$^6$ has a substituent, the substituent is an alkyl group, an amino group, a silyl group, an aromatic hydrocarbon group, a cycloalkyl group, an alkoxy group, a fluoroalkyl group, a halogen atom, a hydroxyl group, a nitro group, a cyano group, a carboxyl group, an aryloxy group, a diarylphosphino group, a diarylphosphine oxide group, or a diarylphosphinoaryl group.

19. The nitrogen-containing heteroaromatic compound according to claim 18, wherein Ar$_1$ is a substituted or unsubstituted carbazolyl group that is bonded to L$_1$ at position 9.

* * * * *

UNITED STATES PATENT AND TRADEMARK OFFICE
CERTIFICATE OF CORRECTION

PATENT NO. : 9,604,972 B2
APPLICATION NO. : 13/606379
DATED : March 28, 2017
INVENTOR(S) : Kei Yoshida et al.

It is certified that error appears in the above-identified patent and that said Letters Patent is hereby corrected as shown below:

Claim 1, Column 73, Lines 7-8:
"phenanthrolnyl group, a substituted or unsubstituted phenazinyl" should read --phenanthrolinyl group, a substituted or unsubstituted phenazinyl--;

Claim 1, Column 73, Line 10:
"group, a substituted or unsubstituted phenothiazinyl group, a substituted or unsubstituted phenoxadinyi group, a substituted or unsubstituted oxazolyl group, a" should read --group, a substituted or unsubstituted phenothiazinyl group, a substituted or unsubstituted phenoxadinyl group, a substituted or unsubstituted oxazolyl group, a--;

Claim 1, Column 73, Line 21:
"unsubstituted fluoroalkyl group, or a cyan group;" should read --unsubstituted fluoroalkyl group, or a cyano group;--;

Claim 1, Column 75, Line 43:
"when $R^1$, $Ar_1$, $L_1$, M, $Ar_2$, R', R", $R^2$, $R^3R^4$, $R^5$, or $R^6$ as" should read --when $R^1$, $Ar_1$, $L_1$, M, $Ar_2$, R', R", $R^2$, $R^3$, $R^4$, $R^5$, or $R^6$ has--;

Claim 3, Column 75, Line 55:
"a cathode:" should read --a cathode;--;

Claim 12, Column 77, Line 45:
"group, a substituted or unsubstituted phenoxadinyi" should read --group, a substituted or unsubstituted phenoxadinyl--;

Claim 12, Column 77, Line 58; and Line 67 to Column 78, Line 1:
"aromatic hydrocarbon group having 6 to 18carbon" should read --aromatic hydrocarbon group having 6 to 18 ring carbon--;

Signed and Sealed this
Twenty-eighth Day of November, 2017

Joseph Matal
*Performing the Functions and Duties of the
Under Secretary of Commerce for Intellectual Property and
Director of the United States Patent and Trademark Office*

Claim 12, Column 77, Line 67 to Column 78, Line 1:
"a substituted or unsubstituted benzofuranyl group, substituted" should read --a substituted or unsubstituted benzofuranyl group, a substituted--;

Claim 12, Column 79, Line 53:
"unsubstitutedquinolyl group, a substituted or unsubstituted" should read --unsubstituted quinolyl group, a substituted or unsubstituted--;

Claim 17, Column 81, Line 15:
"tuted silyl group, a fluorine atom a substituted or" should read --tuted silyl group, a fluorine atom, a substituted or--;

Claim 18, Column 84, Line 25:
"carbazolyl group a substituted or unsubstituted phenan" should read --carbazolyl group, a substituted or unsubstituted phenan--;

Claim 18, Column 84, Line 39:
"containing heteroaromatic group, and M s bonded to" should read --containing heteroaromatic group, and M is bonded to--;

Claim 18, Column 85, Line 19:
"each of X, to $X_8$ is independently CR' or a nitrogen atom;" should read --each of $X_1$ to $X_8$ is independently CR' or a nitrogen atom;--.